(12) United States Patent
Federowicz et al.

(10) Patent No.: US 10,676,842 B2
(45) Date of Patent: **\*Jun. 9, 2020**

(54) AUTOMATED INSTRUMENTATION FOR PRODUCTION OF T-CELL RECEPTOR PEPTIDE LIBRARIES

(71) Applicant: Inscripta, Inc., Boulder, CO (US)

(72) Inventors: Stephen Federowicz, Boulder, CO (US); Deanna Church, Boulder, CO (US); Michael Graige, Boulder, CO (US)

(73) Assignee: Inscripta, Inc., Boulder, CO (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/670,340

(22) Filed: Oct. 31, 2019

(65) Prior Publication Data

US 2020/0063288 A1    Feb. 27, 2020

Related U.S. Application Data

(63) Continuation of application No. 16/392,605, filed on Apr. 23, 2019, now Pat. No. 10,557,216.

(60) Provisional application No. 62/671,266, filed on May 14, 2018, provisional application No. 62/662,126, filed on Apr. 24, 2018.

(51) Int. Cl.
| | |
|---|---|
| *C12N 15/10* | (2006.01) |
| *C40B 50/06* | (2006.01) |
| *C40B 70/00* | (2006.01) |
| *C40B 40/02* | (2006.01) |
| *C40B 20/04* | (2006.01) |
| *C12N 15/90* | (2006.01) |
| *C12N 15/85* | (2006.01) |
| *C12N 9/22* | (2006.01) |
| *C07K 14/74* | (2006.01) |
| *C07K 16/28* | (2006.01) |
| *C40B 40/10* | (2006.01) |
| *C40B 30/04* | (2006.01) |
| *C12N 15/81* | (2006.01) |

(52) U.S. Cl.
CPC ........ *C40B 50/06* (2013.01); *C07K 14/70539* (2013.01); *C07K 16/2809* (2013.01); *C12N 9/22* (2013.01); *C12N 15/1037* (2013.01); *C12N 15/81* (2013.01); *C12N 15/85* (2013.01); *C12N 15/907* (2013.01); *C40B 20/04* (2013.01); *C40B 30/04* (2013.01); *C40B 40/02* (2013.01); *C40B 40/10* (2013.01); *C40B 70/00* (2013.01)

(58) Field of Classification Search
None
See application file for complete search history.

(56) References Cited

U.S. PATENT DOCUMENTS

| | | | |
|---|---|---|---|
| 6,837,995 B1 | 1/2005 | Vassarotti et al. | |
| 7,166,443 B2 | 1/2007 | Walker et al. | |
| 8,332,160 B1 | 12/2012 | Platt et al. | |
| 8,697,359 B1 | 4/2014 | Zhang et al. | |
| 8,926,977 B2 | 1/2015 | Miller et al. | |
| 9,260,505 B2 | 2/2016 | Weir et al. | |
| 9,361,427 B2 | 6/2016 | Hillson | |
| 9,499,855 B2 | 11/2016 | Hyde et al. | |
| 9,776,138 B2 | 10/2017 | Innings et al. | |
| 9,790,490 B2 | 10/2017 | Zhang et al. | |
| 9,896,696 B2 | 2/2018 | Begemann et al. | |
| 9,982,279 B1 | 5/2018 | Gill et al. | |
| 9,988,624 B2 | 6/2018 | Serber et al. | |
| 10,017,760 B2 | 7/2018 | Gill et al. | |
| 10,266,851 B2 | 4/2019 | Chen | |
| 2002/0139741 A1 | 10/2002 | Kopf | |
| 2004/0110253 A1 | 6/2004 | Kappler et al. | |
| 2010/0076057 A1 | 3/2010 | Sontheimer et al. | |
| 2014/0068797 A1 | 3/2014 | Doudna et al. | |
| 2014/0199767 A1 | 7/2014 | Barrangou et al. | |
| 2014/0273226 A1 | 9/2014 | Wu et al. | |
| 2015/0098954 A1 | 4/2015 | Hyde et al. | |
| 2015/0159174 A1 | 6/2015 | Frendewey et al. | |
| 2015/0176013 A1 | 6/2015 | Musunuru et al. | |
| 2015/0191719 A1 | 7/2015 | Hudson et al. | |
| 2016/0024529 A1 | 1/2016 | Carstens et al. | |
| 2016/0053272 A1 | 2/2016 | Wurtzel et al. | |
| 2016/0053304 A1 | 2/2016 | Wurtzel et al. | |
| 2016/0076093 A1 | 3/2016 | Shendure et al. | |
| 2016/0102322 A1 | 4/2016 | Ravinder et al. | |
| 2016/0168592 A1 | 6/2016 | Church et al. | |
| 2016/0289673 A1 | 10/2016 | Huang et al. | |
| 2016/0298134 A1 | 10/2016 | Chen et al. | |
| 2017/0002339 A1 | 1/2017 | Barrangou et al. | |
| 2017/0051310 A1 | 2/2017 | Doudna et al. | |
| 2017/0073705 A1 | 3/2017 | Chen et al. | |
| 2017/0191123 A1 | 7/2017 | Kim et al. | |
| 2017/0240922 A1 | 8/2017 | Gill et al. | |
| 2018/0028567 A1 | 2/2018 | Li et al. | |
| 2018/0052176 A1 | 2/2018 | Holt et al. | |
| 2018/0073013 A1 | 3/2018 | Lorenz et al. | |
| 2018/0112235 A1 | 4/2018 | Li et al. | |
| 2019/0017072 A1 | 1/2019 | Ditommaso et al. | |
| 2019/0169605 A1 | 6/2019 | Masquelier et al. | |

FOREIGN PATENT DOCUMENTS

| | | |
|---|---|---|
| EP | 2395087 | 12/2011 |
| WO | WO 2003/087341 | 10/2003 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

(Continued)

*Primary Examiner* — Christopher M Gross
(74) *Attorney, Agent, or Firm* — Sarah Brashears; Dianna L. DeVore

(57) ABSTRACT

The present disclosure provides instrumentation and automated methods for creating cell surface display libraries, where the cells of the library display engineered peptides on their cell surfaces for identification of antigens that bind to T-cell receptors. The engineered peptides may be putative antigens or binding regions of the T-cell receptors.

17 Claims, 39 Drawing Sheets

(56) References Cited

FOREIGN PATENT DOCUMENTS

| WO | WO 2010/079430 | 7/2010 |
|---|---|---|
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO 2017/053902 | 3/2017 |
| WO | WO 2017/078631 | 5/2017 |
| WO | WO 2017/174329 | 10/2017 |
| WO | WO 2018/031950 | 2/2018 |
| WO | WO 2018/083339 | 5/2018 |
| WO | WO 2018/191715 | 10/2018 |

OTHER PUBLICATIONS

Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x | www.nature.com/naturecommunications pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "Tales of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US2018/053671, dated Nov. 23, 2018, p. 1-12.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.

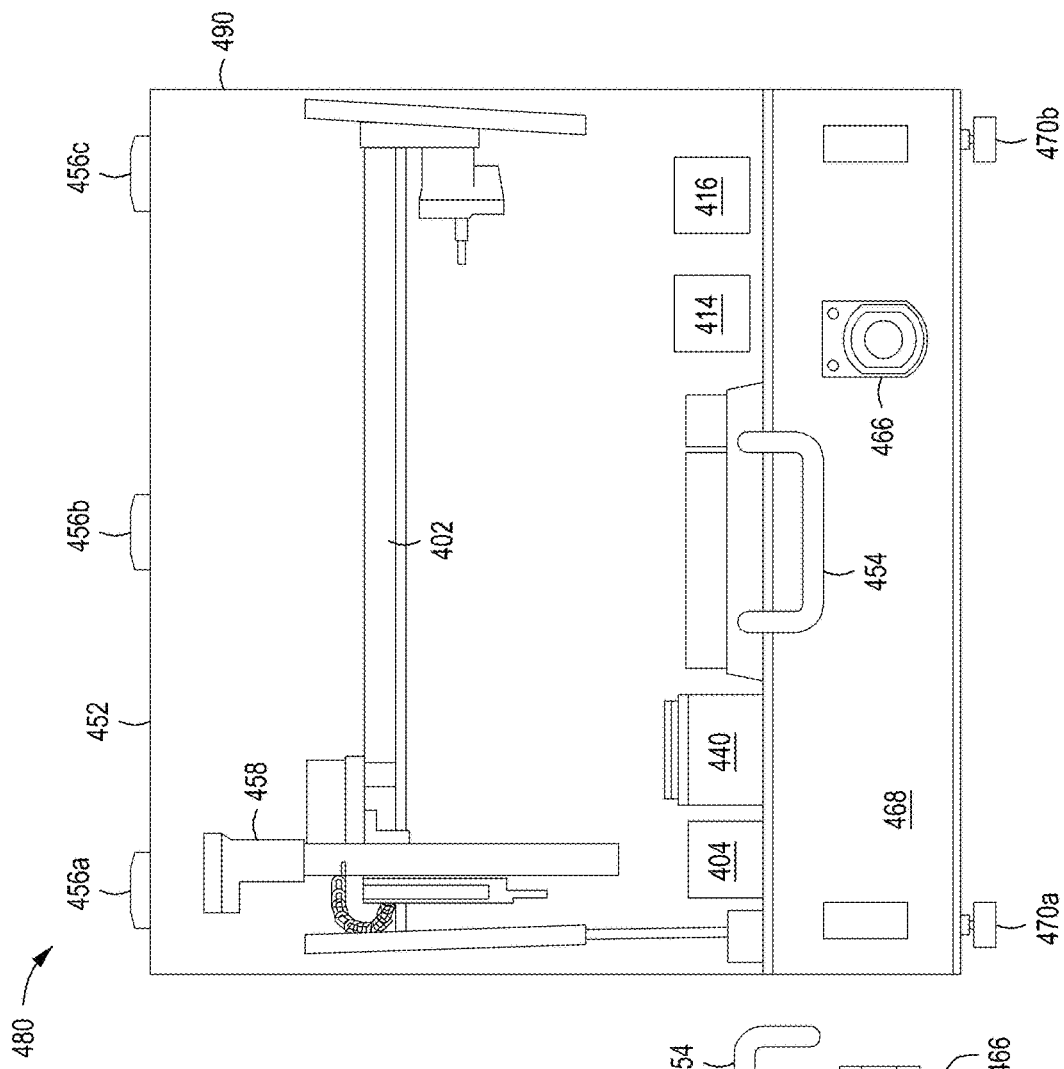
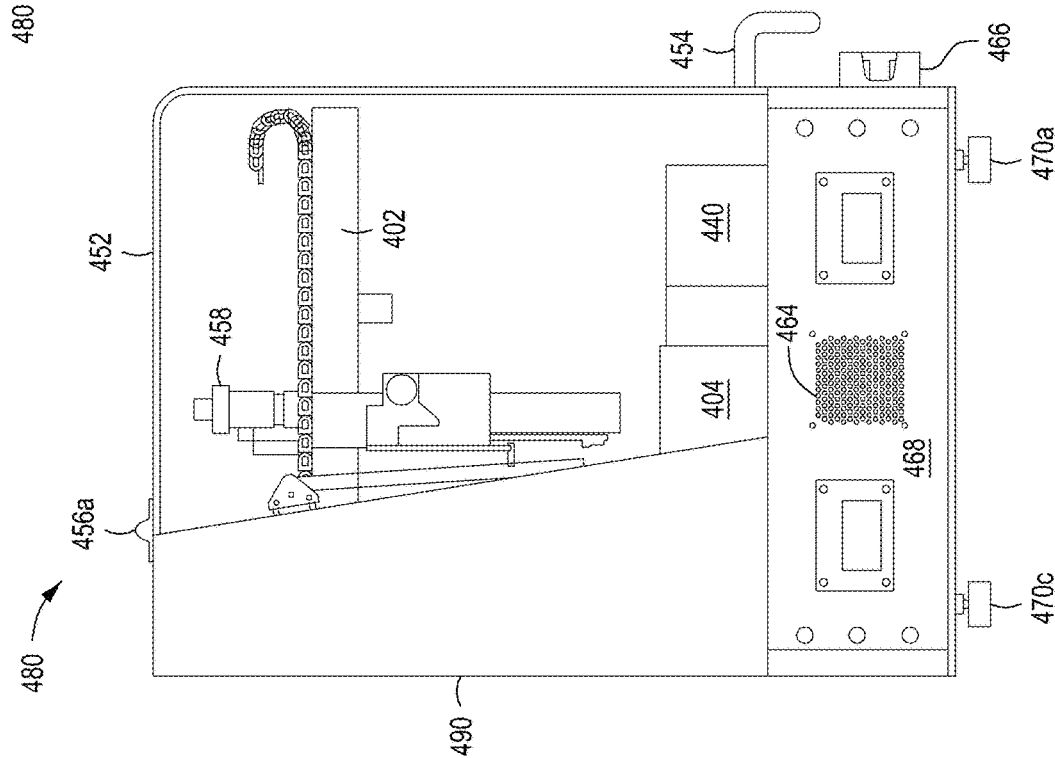

Top view of microwells
Medium magnification

Darker microwells = growth

Microwells with membrane removed
High magnification

AUTOMATED INSTRUMENTATION FOR PRODUCTION OF T-CELL RECEPTOR PEPTIDE LIBRARIES

RELATED APPLICATIONS

This application is a continuation of U.S. Ser. No. 16/392,605, filed Apr. 23, 2019, which claims priority to U.S. Provisional Patent Application Ser. No. 62/671,266, entitled "MULTIPLEXED METHODS FOR PRODUCTION AND USE OF CELL SURFACE DISPLAY LIBRARIES," filed May 14, 2018; and U.S. Patent Application Ser. No. 62/662,126, entitled "MULTIPLEXED METHODS FOR PRODUCTION AND USE OF CELL SURFACE DISPLAY LIBRARIES," filed Apr. 24, 2018, both of which are hereby incorporated by reference in their entireties for all purposes.

FIELD OF THE INVENTION

The present disclosure relates to automated multi-module instruments and multiplexed methods of making cell surface display libraries using genomic editing technologies.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The binding and activation of a T-cell receptor (TCR) to its specific antigen has been difficult to identify in high throughput systems due to the diversity of major histocompatibility complexes, the variety of potential antigens, and the diversity of T-cells in humans and animals. Conventional techniques such as HPLC require a priori information about the TCR target, and the identification process can be both lengthy and cumbersome.

There is thus a need in the art for better and more robust means for identifying specific antigens for TCRs in a high throughput, multiplexed manner. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides compositions, instruments and automated methods for providing multiplexed displays of engineered peptides on the surface of a population of cells. The engineered peptides are preferably expressed in the cells under conditions that provide both secretion and display of the engineered peptides on the cell surfaces, thus providing access of the engineered peptides to potential binding targets. The cell populations can be engineered using an automated editing system that provides for one or more targeted edits per cell, allowing for the rational design of a library of cells having engineered peptides displayed on their respective surfaces. Accordingly, this disclosure describes various automated methods for expressing and displaying engineered peptides on cells.

In some embodiments, the disclosure provides a method of producing a cell library expressing engineered peptides for identification of T-cell receptor (TCR)-antigen binding, the method comprising providing a population of cells, processing the population of cells using an instrument for multiplexed nuclease-directed genome editing using introduced nucleic acids and a nucleic acid-directed nuclease to create cells comprising nucleic acids that encode engineered peptides configured to be displayed on a surface of the cells, incubating the processed cells to facilitate nucleic acid editing in the cells, wherein the editing provides nucleic acids that encode engineered peptide antigens in the cells, and allowing the cells to express and display the engineered peptides on the surface of the cells.

In some aspects, the engineered peptides are putative TCR binding antigens. In other aspects, the engineered peptides comprise predicted TCR binding regions. In some aspects the engineered peptides derive from a target genomic sequence and contain an inserted N-terminus or C-terminus cell surface display conferring tag.

In other embodiments, the disclosure provides methods of producing a cell library expressing engineered putative T-cell receptor (TCR) antigens on the surface of the cells, the method comprising providing a population of cells, processing the population of cells using an instrument for multiplexed nuclease-directed genome editing using introduced nucleic acids and a nuclease to create cells comprising nucleic acids that encode engineered peptide antigens configured to be displayed on a surface of the cells, incubating the processed cells to facilitate nucleic acid editing in the cells, wherein the editing provides nucleic acids that encode engineered peptide antigens in the cells, and allowing the cells to express and display the engineered peptide antigens that are putative TCR antigens on the surface of the cells.

The engineered peptide antigens in the population of edited cells preferably comprise rationally designed peptides that can be displayed on a cell surface in a manner by which the antigen is available for binding to a TCR target, either known TCRs and/or orphan TCRs. In some aspects, the engineered peptide antigens are known antigens of one or more TCRs.

In specific embodiments the antigen is displayed on the cell surface as part of an MHC (e.g. HLA) which includes the peptide antigen thereby forming a TCR ligand. Accordingly, in some aspects, the cells display the engineered peptide antigens as part of a ligand. In some aspects, the cells co-express putative TCR antigens and MHC molecules.

Peptide antigens for use with the systems and methods of the disclosure include known antigens of one or more TCRs, predicted antigens for one or more TCRs, or random peptides created using nucleases in the automated cell editing instruments of the present disclosure. In embodiments, the peptides that are displayed are created using forward engineering to create peptide sequences based on predictions of what antigens may be useful for specific TCRs.

In some embodiments, the disclosure provides methods of producing a cell library expressing engineered peptides derived from the cells' genome(s) on the surface of cells, the method comprising providing a population of cells, processing the population of cells using an instrument for multiplexed nuclease-directed genome editing using introduced nucleic acids and a nuclease to create cells comprising nucleic acids that encode engineered proteins configured with an N-terminus or C-terminus cell surface display conferring tag to be displayed on a surface of the cells, incubating the processed cells to facilitate nucleic acid editing in the cells, wherein the editing provides nucleic acids that encode cell surface display conferring tags at the N-terminus or C-terminus of engineered proteins in the cells, and allowing the cells to express and display the engineered proteins on the surface of the cell.

In some embodiments, the disclosure provides multiplexed method for identifying peptides that selectively bind one or more TCRs, the method comprising providing a population of cells, processing the population of cells using an automated system for multiplexed nuclease-directed genome editing, wherein the system comprises the steps of introducing nucleic acids that encode engineered peptide antigens and a nuclease to a population of cells, incubating the cells to facilitate nucleic acid editing in the cells, allowing the edited cells to express and display the engineered peptide antigens on the surface of the edited cells, screening the edited cells displaying the engineered peptide antigens against one or more TCRs, and identifying the edited cells expressing engineered peptide antigens that selectively bind to one or more TCRs.

In some aspects, the disclosure further provides isolating the nucleic acids encoding the engineered peptide antigens that selectively bind to one or more TCRs from the cells. In some aspects, the disclosure further provides isolating the nucleic acids encoding the engineered peptides that selectively bind to one or more putative TCR antigens from the cells.

In some aspects, the cells encoding specific peptides are identified by detection of a barcode associated with the engineered peptides. In some aspects, the cells encoding specific are identified by detection of a barcode associated with the engineered peptide antigens that selectively bind to one or more TCRs. In some embodiments, the barcode is used to isolate and/or further identify or process the cells and nucleic acids encoding the peptides for further analysis. In such embodiments, the barcode can be used as a "handle" to pull out the cells of interest for further analysis.

In specific aspects, the disclosure provides a method of producing a cell library expressing engineered peptide antigens on the surface of cells by providing a population of cells, editing the population of cells using one or more introduced nucleic acids comprising a guide RNA covalently linked to a donor DNA (e.g., homology arm) that selectively binds to a genomic region of interest and a nuclease, incubating the cells to facilitate nucleic acid editing in the cells, wherein the editing provides nucleic acids that encode engineered peptide antigens in the cells, and allowing the cells to express and display the engineered peptide antigens on the surface of the edited cells.

In other specific aspects, the disclosure provides a method of producing a cell library expressing engineered peptide antigens on the surface of cells by providing a population of cells, editing the population of cells employing an automated instrument for multiplexed nuclease-directed genome editing using introduced nucleic acids comprising the edits and a nuclease, incubating the cells to facilitate nucleic acid editing in the cells, wherein the editing provides nucleic acids that encode engineered peptide antigens in the cells, and allowing the cells to express and display the engineered peptide antigens on the surface of the edited cells.

The engineered peptide antigens in the population of edited cells preferably comprise rationally designed peptides that can be displayed on a cell surface in a manner by which the antigen is available for binding to a T-cell receptor ("TCR") target. In some aspects of the disclosure, the engineered peptides are derived from target genomic sequences.

Various nucleases may be used with the editing methods of the present disclosure, including zinc finger nucleases, meganucleases, TALENS, and nucleic acid-directed nucleases (e.g., RNA-directed nucleases). Preferably, the editing methods are carried out using nucleic acid-directed nucleases, and more preferably RNA-directed nucleases.

In specific embodiments, the disclosure provides multiplexed methods for identifying cells expressing engineered putative TCR antigens on their surface comprising providing a population of cells, editing the population of cells using an automated instrument for multiplexed nuclease-directed genome editing and introduced nucleic acids and a nuclease to create nucleic acids that encode putative TCR antigens in the cells, incubating the cells to facilitate nucleic acid editing in the cells, allowing the cells to express and display the engineered putative TCR antigens on their surface, screening the cells displaying the engineered putative TCR antigens against a target, and identifying the cells expressing engineered putative TCR antigens that selectively bind to the target.

In one embodiment, the disclosure provides multiplexed methods for identifying cells expressing engineered putative TCR antigens on their surface comprising providing a population of cells; editing the population of cells using an automated instrument for multiplexed nuclease-directed genome editing and introduced nucleic acids and a nucleic acid-directed nuclease thereby creating cells comprising nucleic acids that encode engineered putative TCR antigens, incubating the cells to facilitate nucleic acid editing in the cells, allowing the edited cells to express and display the engineered putative TCR antigens on their surface, screening the cells displaying the engineered putative TCR antigens against a target, selecting the cells expressing engineered putative TCR antigens that selectively bind to one or more TCR targets, and detecting or isolating the nucleic acid encoding the antigens. Alternatively, the conditions can be varied to determine the selectivity under different conditions.

Detection of a specific peptide in a cell of interest can be accomplished using various methods known in the art, e.g., sequencing, hybridization, identification of a barcode indicative of an antigen sequence, and the like. Barcodes and other features can also be used for further analysis, e.g., by providing a basis for identifying and/or isolating cells of interest encoding peptides identified for elucidation of TCR binding.

In one aspect, the disclosure provides methods for the immobilization of one or more engineered peptide antigens on a cell surface by providing fusion proteins for display of one or more engineered peptide antigens on a yeast cell surface. In one embodiment, the disclosure provides for methods for displaying an engineered peptide antigen as part of an MHC antigen (e.g., HLA) on the cell surface. In certain embodiments, the cells display multiple copies of a single engineered antigen.

In specific embodiments, the disclosure provides methods for providing receptors or binding regions thereof on the cell In specific embodiments, the disclosure provides multiplexed methods for identifying cells expressing engineered predicted TCR binding regions (e.g., predicted binding regions of orphan TCRs) on their surface comprising providing a population of cells, editing the population of cells using an automated instrument for multiplexed nuclease-directed genome editing and introduced nucleic acids and a nuclease to create nucleic acids that encode TCR binding regions in the cells, incubating the cells to facilitate nucleic acid editing in the cells, allowing the cells to express and display the engineered TCR binding regions on their surface, screening the cells displaying the engineered TCR binding regions against a target, and identifying the cells expressing engineered TCR binding regions that selectively bind to putative antigens.

In one embodiment, the disclosure provides multiplexed methods for identifying cells expressing engineered predicted binding regions from TCRs (e.g., orphan TCRs) on their surface comprising: providing a population of cells, editing the population of cells using an automated instrument for multiplexed nuclease-directed genome editing and introduced nucleic acids and a nucleic acid-directed nuclease thereby creating cells comprising nucleic acids that encode engineered TCR binding regions, incubating the cells to facilitate nucleic acid editing in the cells, allowing the edited cells to express and display the engineered TCR binding regions on their surface, screening the cells displaying the engineered TCR binding regions against a target, and identifying the cells expressing engineered TCR binding regions that selectively bind to one or more putative TCR binding antigens. Alternatively, the conditions can be varied to determine the selectivity under different conditions.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 4A-4D depict an automated multi-module instrument and components thereof with which to generate the cell surface libraries of the disclosure.

It should be understood that the drawings are not necessarily to scale, and that like reference numbers refer to like features.

DETAILED DESCRIPTION

Figure 1:
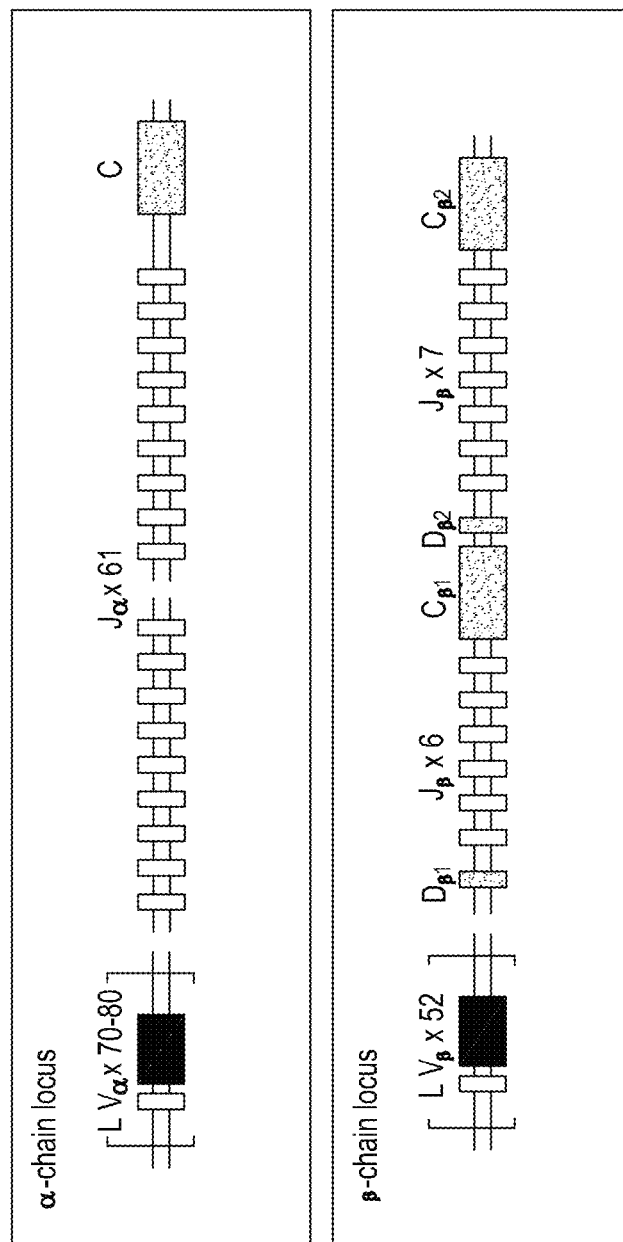
FIG. 1 is a schematic showing the structure of the TCRα and TCRβ loci.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual*. 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The term "engineered peptide antigen" encompasses naturally occurring and synthetic polypeptides and protein constructs that comprise a synthetic polypeptide or naturally occurring peptide associated with different elements, like, for instance, peptides for MHC display of the peptide, an immobilization peptide, reporter peptide or secretion peptide. engineered peptide antigens are encoded and/or expressed from a recombinant nucleic acid that may be engineered to include sequence variants, recombinant promoters, transcriptional control elements, fusion peptides, other modifications, or any combination of two or more thereof. The peptide presentation may include presentation of all or a portion of a protein of interest. In some embodiments, engineered peptide antigens comprise a binding motif that is modified by a coupling enzyme, resulting in the coupling of a second binding target to the binding motif. In some embodiments, the second binding target is coupled to the engineered peptide antigen intracellularly.

As used herein, "enrichment" refers to enriching for edited cells by singulation, optionally inducing editing, and growth of singulated cells into terminal-sized colonies (e.g., saturation or normalization of colony growth).

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, the terms "leader peptide", "secretion peptide" or secretion leader peptide refers to any signaling sequence that directs a synthesized fusion protein away from the translation site, including signaling sequences that will result in the fusion peptide crossing the cell membrane and being secreted.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible, and in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rifampicin, puromycin, hygromycin, blasticidin, and G418 may be employed. In other embodiments, selectable markers include, but are not limited to sugars such as rhamnose. human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The term "specifically binds" as used herein includes an interaction between two molecules, e.g., an engineered peptide antigen and a binding target, with a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

The term "variant" may refer to a polypeptide or polynucleotide that differs from a reference polypeptide or polynucleotide, but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, all editing and selection components may be found on a single vector. Further, the engine and editing vectors comprise control sequences operably linked to, e.g., the nuclease coding sequence, recombineering system coding sequences (if present), donor nucleic acid, guide nucleic acid, and selectable marker(s).

Cell Libraries, Screening and Editing Methods

The present disclosure provides multiplexed methods and automated instruments for creating cell populations with cell surface displays where the methods employ editing technologies. The cell populations edited using the multiplexed and automated instrumentation of the disclosure comprise one or more putative receptor antigens displayed on a cell's surface and available for binding to a binding target. The cells that may be edited and used according to the disclosure include, but are not limited to, bacterial cells, yeast cells and mammalian cells. In addition, the cells that are edited may include sequences that are heterologous to the host (e.g., editing of mammalian sequences inserted into a yeast or bacterial genome).

In particular the methods and automated instruments used to create the cells are useful in identifying antigens that specifically bind to T-cell receptors (TCRs). The ability to quickly and easily identify antigens, e.g. putative antigen targets of orphan TCRs, can be extremely useful in immunology, e.g., immunotherapy research and development.

The disclosure also provides methods for multiplexed display and screening of antigens (e.g., as components of ligands) that bind to a TCR target. In some embodiments, the antigens are displayed on a cell surface using any of the cell display methods described herein. In some embodiments the antigens are complexed in an MHC complex and displayed on the cell population surfaces.

Antigens that specifically bind to T-cell receptors (TCRs) can be identified using various detection methods, including isolation of the cells and sequencing of the introduced antigen sequences or identification by hybridization, e.g., on an array. In other aspects, the barcodes associated with a specific displayed antigen may be identified and used to identify the antigens that selectively bind to a TCR. The barcodes may be identified, e.g., using sequencing and/or array hybridization.

In some embodiments, the cells that encode engineered peptide antigens that selectively bind to one or more targets of interest from the cells are identified and/or isolated using a barcode associated with the peptide. In specific embodiments, the barcode is used to further isolate and/or analyze the cells expressing the peptides identified as potentially elucidating the binding of an antigen to a TCR. In such embodiments, the barcode can be used as a "handle" to pull out the cells of interest for further analysis.

In some embodiments, the method comprises producing via genome editing a population or library of edited cells each displaying a single engineered peptide antigen on its surface, wherein the different engineered peptide antigens are created using nuclease editing and are subsequently displayed on the surface of different cells. In other embodiments, the editing method results in a population or library of edited cells, where each edited cell displays a plurality of different engineered peptide antigens on its surface. The cells thus can express one or more engineered peptide antigens that are displayed on the cell surface of a single cell of the population, optionally in one or more MHCs (e.g., HLAs)

In some embodiments, the disclosure provides a method for displaying an engineered peptide antigen on a cell surface, the method comprising editing a cell using a nucleic acid-directed nuclease to create a nucleic acid encoding an engineered putative HLA and incubating an edited cell under conditions sufficient for expressing the engineered HLA.

In some embodiments, the cells of the library display at least $10^2$ engineered peptide antigens. In some embodiments, the cell displays at least $10^3$ engineered peptide antigens. In some embodiments, the cell displays at least $10^4$ engineered peptide antigens. In some embodiments, the cell displays at least $10^5$ engineered peptide antigens, at least $10^6$ engineered peptide antigens or more. In some embodiments, the disclosure provides a library of any of the cells described herein. In some embodiments, the library has at least $10^8$ different members. In some embodiments, the library has at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ cells.

In some embodiments, the disclosure provides populations or libraries of edited cells, wherein the cells encode different engineered peptide antigens and variants thereof, and wherein the variants also comprise a binding motif capable of coupling a binding target. In some embodiments, the binding motif is a biotinylation motif. In some embodiments, the library has at least $10^8$ different members. In some embodiments, the library has at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members.

Methods of editing that may be used to generate the libraries or populations of cells are described in detail below, as are the cell processing modules and instruments used to perform the nuclease-directed genome editing.

The antigens displayed on the edited cells in the libraries can be any length between 3-50 amino acids and are preferably between 5-20 amino acids. In specific aspects, the amino acid peptides are displayed in a manner that allows the appropriate presentation of the antigenic region of a peptide, e.g., 8-11 amino acids that are known to be available in an MHC on the cell surface.

T-Cell Receptors

T-cell receptors (TCRs) are structurally similar to immunoglobulins, are encoded by homologous genes, and are assembled by somatic recombination from sets of gene segments similar to recombination of immunoglobulin genes. TCR loci have roughly the same number of V gene segments but more J gene segments, and there is greater diversification of the junctions between gene segments during gene rearrangement. Moreover, functional TCRs are not known to diversify their V genes after rearrangement through somatic hypermutation. This leads to a TCR in which the highest diversity is in the central part of the receptor, which contacts the bound antigen of the ligand.

TCR α and β chains each consist of a variable (V) amino-terminal region and a constant (C) region. The organization of the TCRα and TCRβ loci is shown in FIG. 1. The TCRα locus, like those for the immunoglobulin light chains, contains V and J gene segments ($V_\alpha$ and $J_\alpha$). The TCRβ locus, like that for the immunoglobulin heavy-chain, contains D gene segments in addition to $V_\beta$ and $J_\beta$ gene segments.

Figure 2:
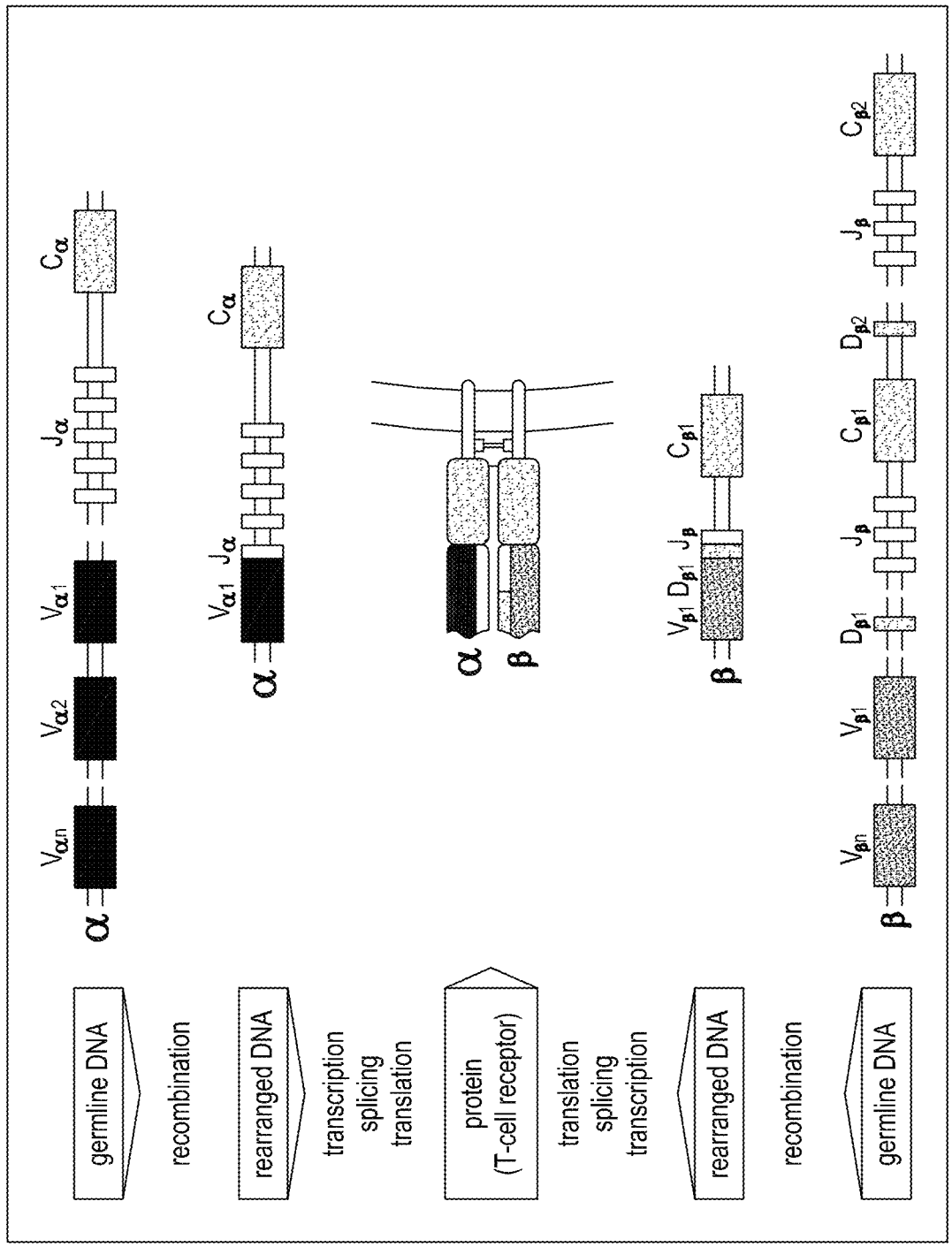
FIG. 2 is a schematic showing how TCR gene segments rearrange during T-cell development to form complete V-domain exons.

The TCR gene segments rearrange during T-cell development to form complete V-domain exons (FIG. 2). The TCR gene segments are flanked by heptamer and nonamer recombination signal sequences (RSSs) that are homologous to those flanking immunoglobulin gene A further shared feature of immunoglobulin and TCR gene rearrangement is the presence of P- and N-nucleotides in the junctions between the V, D, and J gene segments of the rearranged TCRβ gene. In T cells, P- and N-nucleotides are also added between the V and J gene segments of all rearranged TCRα genes, whereas only about half the V-J joints in immunoglobulin light-chain genes are modified by N-nucleotide addition and these are often left without any P-nucleotides as well.

The ligand for the TCR is usually a peptide bound to an MHC molecule. Most of the variability of the TCR ligand is thus in the bound antigenic peptide occupying the center of the surface in contact with the receptor. In fact, the three-dimensional structure of the antigen-recognition site of a TCR looks much like that of an antibody molecule.

The structural diversity of TCRs is mainly attributable to combinatorial and junctional diversity generated during the process of gene rearrangement. The variability in TCR chains is focused on the junctional region encoded by V, D, and J gene segments and modified by P- and N-nucleotides. The TCRα locus contains many more J gene segments than either of the immunoglobulin light-chain loci: in humans, 61 $J_\alpha$ gene segments are distributed over about 80 kb of DNA, whereas immunoglobulin light-chain loci have only five J gene segments at most. Because the TCRα locus has so many J gene segments, the variability generated in this region is even greater for TCRs than for immunoglobulins. This region encodes the CDR3 loops in immunoglobulins and TCRs that form the center of the antigen-binding site. Thus, the center of the TCR will be highly variable, whereas the periphery will be subject to relatively little variation.

Figure 3:
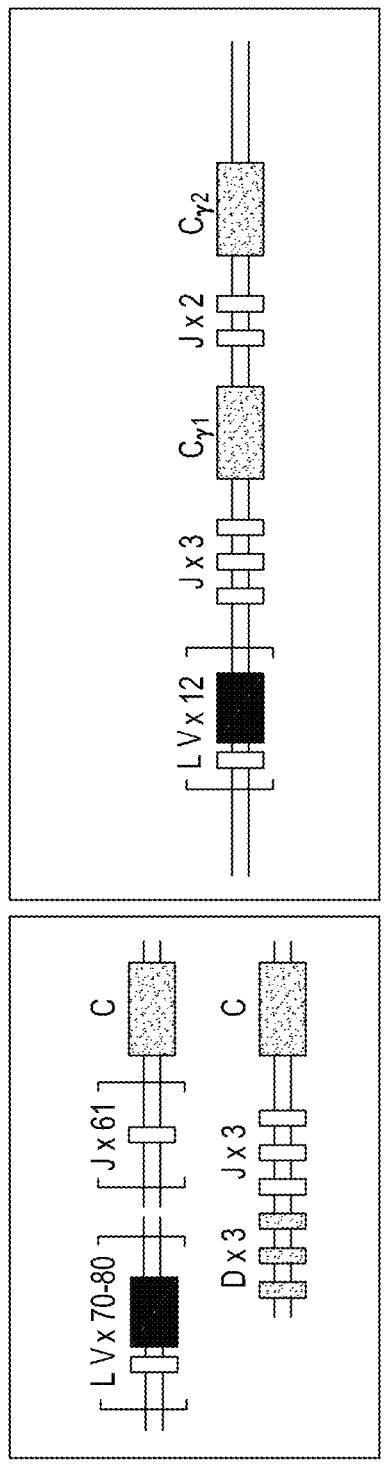
FIG. 3 is a schematic showing the cluster of gene segments encoding the δ chain within the TCRα locus.

A minority of T cells bear TCRs composed of γ and δ chains. The cluster of gene segments encoding the δ chain is found entirely within the TCRα locus, between the $V_\alpha$ and the $J_\alpha$ gene segments. See FIG. 3. Because all $V_\alpha$ gene segments are oriented such that rearrangement will delete the intervening DNA, any rearrangement at the α locus results in the loss of the δ locus. There are substantially fewer V gene segments at the TCRγ and TCRδ loci than at either the TCRα or TCRβ loci or at any of the immunoglobulin loci. Increased junctional variability in the δ chains may compensate for the small number of V gene segments and has the effect of focusing almost all of the variability in the γ:δ receptor in the junctional region. As we have seen, the amino acids encoded by the junctional regions lie at the center of the TCR binding site. In humans, the TCRγ and TCRδ loci, like the TCRα and TCRβ loci, have discrete V, D, and J gene segments, and C genes.

T cells bearing γ:δ receptors are a distinct lineage of T cells whose functions are at present unknown. The ligands for these receptors are also largely unknown. Some γ:δ TCRs appear to be able to recognize antigen directly, much as antibodies do, without the requirement for presentation by an MHC molecule or processing of the antigen. Accordingly, the co-expression of an MHC molecule with a putative antigen is optional.

Cell Surface Display

Various display technologies can be used with the cell libraries and populations generated by the methods and instrumentation described herein, including yeast surface display technologies, mammalian cell surface display technologies, and bacterial surface display technologies. Cell surface display technologies include, but are not limited to, those disclosed in U.S. Pat. Nos. 8,883,692; 8,685,893; and 6,699,658; U.S. Pat. Pub. Nos. 20170218382; 20170088611; 20150307560; 20150203834; 20140221621; 20140031292; 20140235476, 20140221621; 20130184177; 20110008883; No. 20100233195; 20100210473; 20100216659; 20090280560; 20090111126; and 20040146976. Bacterial cells, yeast cells and mammalian cells can all be used for cell surface display.

In certain embodiments, immobilization of an engineered peptide antigen to a cell surface may involve specific interactions between the engineered peptide antigen and a binding motif on the engineered peptide antigen.

The engineered peptide antigens of the invention can be expressed in any cell amenable to editing and surface display, and the invention embraces any prokaryotic or eukaryotic cell, including bacterial cells, yeast cells (e.g., *Saccharomyces* and/or *Picchia* species), insect cells, *Xenopus* cells, and mammalian cells. Cells that are particularly suited for expression of the fusion proteins of the invention are *E. coli., S. cerevisiae*, CHO and 293T cells. The cells may be 'wild type' cells or the cells may be optimized for a particular characteristic or for a particular enzyme function that may aid in protein expression. Optimized or engineered cells include cells that have an optimized capability to take up and maintain nucleic acids, cells that have increased protein synthesis capability, and/or cells that have increased protein secretion capability. Cells that maintain the integrity of the edited nucleic acid and the synthesized proteins are particularly useful.

In specific aspects, the edited cells comprise a binding target on their surface, and the cells are incubated under conditions resulting in secretion of the engineered peptide antigen, wherein the engineered peptide antigen binds to a binding target, thereby displaying the engineered peptide antigen on the cell surface.

A commonly used organism for protein display is yeast. Yeast display offers the advantage over bacteria-based technologies in that yeast can process proteins that require endoplasmic reticulum (ER)-specific post-translational processing for efficient folding and activity. While mammalian cell display also facilitates post-translational processing, yeast offers the advantage of ease of generation of nucleic acid libraries as the vectors can be simpler, and yeast allow for an easier introduction of editing machinery (e.g., editing vectors) into the cells. Most yeast expression fusion proteins are based on GPI (Glycosyl-Phosphatidyl-Inositol) anchor proteins which play important roles in the surface expression of cell-surface proteins and are essential for the viability of the yeast. One such anchor protein—alpha-agglutinin— consists of a core subunit encoded by AGA1 and is linked through disulfide bridges to a small binding subunit encoded by AGA2. Proteins encoded by the nucleic acid libraries described herein can be introduced on the N-terminal region of AGA1 or on the C terminal or N-terminal region of AGA2. These fusion patterns will result in the display of the polypeptide on the yeast cell surface.

In some embodiments, fusion proteins for yeast display include an engineered peptide antigen fused to the N-terminal or C-terminal part of a protein capable of anchoring in a eukaryotic cell wall (e.g., a-agglutinin, AGA1, Flo1 or major cell wall protein of lower eukaryotes; see U.S. Pat. Nos. 6,027,910 and 6,114,147 which are hereby incorporated by reference), for example, proteins fused with the GPI fragment of Flo1 or to the Flo1 functional domain (Kondo et al., Appl. MicroBiol. Biotech., 64: 28-40 (2004)).

In addition to surface display methods based on established fusion proteins comprising a GPI anchor motif, the invention also embraces display methods based on novel fusion proteins comprising a modified GPI anchor motif. Fusion proteins of the invention may comprise a protein to be displayed (e.g., one or more engineered peptide antigens, binding targets, molecular targets, substrates, etc., or any combination thereof), a GPI anchor and appropriate signaling sequences, which may be post-translationally modified when the fusion protein is expressed in yeast. As a protein containing the GPI anchor and C-terminal signaling sequence is trafficked through the ER, a hydrophobic region on the C-terminal signal sequence adjacent to the GPI anchor becomes embedded in the ER membrane, where it is cleaved by an ER protease. As the ER protease cleaves this C-terminal signal sequence, it simultaneously attaches a preformed GPI anchor to the new C-terminus of the engineered peptide antigen (e.g., binding target, molecular target, substrate, etc., or any combination thereof) ultimately resulting in the display of the protein (e.g., binding target, molecular target, substrate, etc., or any combination thereof) on the cell surface (See, e.g., Kondo et al., cited above). The invention embraces C-terminal sequences with improved processing properties resulting in the improved display of fusion proteins comprising the GPI-anchor proteins. Improved display comprises an increase in the number of displayed proteins and/or an increase in the number of correctly expressed proteins. In some embodiments, C-terminal sequences with improved processing properties are evolved by screening libraries containing variant C-terminal sequences according to techniques known in the art.

In some embodiments, the disclosure provides a method for displaying an engineered peptide antigen on a cell, the method comprising incubating an edited cell comprising a first nucleic acid under conditions sufficient for expressing an engineered peptide antigen encoded by the first nucleic acid, wherein the cell displays a first binding target, wherein the engineered peptide antigen comprises a binding motif and a second binding target is coupled to the binding motif when the engineered peptide antigen is expressed, and, wherein the expressed engineered peptide antigen is secreted from the cell and displayed on the cell surface via binding of the second binding target to the first binding target. In some embodiments, the first binding target is an avidin-like protein. In some embodiments, the second binding target is biotin. In some embodiments the binding motif is a biotinylation peptide. In some embodiments, coupling of the second binding target is done by a coupling enzyme. In some embodiments, the coupling enzyme is a biotin ligase.

In some embodiments, the disclosure provides a method for generating a library of edited cells comprising engineered (edited) peptide antigens displayed on the cell surfaces of the cells, the method comprising introducing a plurality of editing vectors into a population of cells, creating conditions to allow the editing vectors to edit nucleic acids in the cells; and creating conditions where the edited cells express the engineered peptide antigens and display the engineered peptide antigens on the cell surfaces, wherein the vectors comprise a nuclease, and a donor nucleic acid sequence comprising an edit in the coding region of the antigen to be engineered. In specific aspects, the encoded engineered peptide antigens comprise a unique polypeptide linked to an immobilization peptide, wherein the immobilization peptide comprises a first binding motif that selectively binds to a second binding motif present on the cell surface of the edited cells, and the engineered peptide antigens are expressed under conditions sufficient for binding of the first binding motif to the second binding motif on the cell surface. The immobilization peptide may also or alternatively comprise, for example, a transmembrane polypeptide, a polypeptide membrane anchor, a GPI-linked polypeptide or a natural surface polypeptide.

In some embodiments, the disclosure provides a method for generating a library of edited cells expressing engineered peptide antigens displayed on a cell surface, the method comprising introducing a plurality of vectors into a population of cells, wherein the vectors comprise a nucleic acid-guided nuclease, a guide RNA, and a donor nucleic acid comprising an edit in the coding region of the protein to be engineered. In specific aspects, the antigens to be edited are encoded engineered peptide antigens that comprise a unique polypeptide linked to an immobilization peptide, wherein the immobilization peptide comprises a first binding motif that selectively binds to a second binding motif present on the cell surface of the edited cells, and the engineered peptide antigens are expressed under conditions sufficient for binding of the first binding motif to the second binding motif on the cell surface.

In the aspects that comprise the use of an immobilization peptide or other moiety comprising a binding motif, the peptide or motif can be linked to the C-terminus or the N-terminus of the engineered peptide antigen.

In some embodiments, the engineered peptide antigen further comprises a leader peptide. The leader peptide or secretion peptide may be proteolytically removed from the mature protein concomitant or immediately following export of the protein into the lumen of intracellular compartment along the secretory pathway. The leader peptide may be a naturally occurring sequence or a synthetic sequence.

The edited cell library can have at least 2, at least 5, at least 10, at least 50, at least 100, at least 1000, at least 10,000, at least 100,000, at least 1,000,000, at least at least $10^7$, at least $10^8$, at least $10^9$, at least $10^{10}$ or at least $10^{11}$ cells comprising one or more engineered peptide antigens.

In some embodiments the expression of the engineered peptide antigens in the cells is inducible or transient. In some embodiments, no induction step is necessary and incubating the cell results in the expression of the engineered peptide antigen. In some embodiments, engineered peptide antigens comprising a first binding motif are secreted and bind to a second binding motif present on the cell surface, thereby displaying the engineered peptide antigen on the cell surface. In some embodiments, the first binding motif is avidin, streptavidin or neutravidin and the second binding motif is biotin. In some embodiments, avidin is covalently conjugated to the cell surface (e.g., directly or indirectly). Yet in some embodiments, the first binding target is expressed by the cell and displayed at the cell surface. For example, one of the binding targets may be expressed by the cell as a fusion protein such as a cell wall or a membrane fusion protein and displayed at the surface of the cell.

Screening Methods

The methods of the disclosure may be useful to identify one or more peptides that selectively bind to a TCR. By providing a system that creates a cell library with engineered peptide antigens displayed on the surface of the cells in which they are expressed, cells that express engineered peptide antigens can be identified using any assay that can be performed on a cell surface (e.g., performed on a cellular preparation to detect one or more molecules that are displayed on the cell surface). The methods of the disclosure can be used to screen libraries expressing engineered peptide antigen variants to identify one or more TCRs that selectively bind to the antigen(s).

An embodiment of the disclosure provides a method for selecting cells displaying engineered peptide antigens with desirable affinity or specificity for a target TCR, e.g., a known TCR or an orphan TCR. Some aspects of the invention relate to methods to screen for cells expressing an antigen that can interact with a specific target molecule (e.g., a known TCR or orphan TCR) with a desired specificity.

In some embodiments, the disclosure provides an antigen screening method comprising expressing an engineered peptide antigen in a cell edited using a nuclease, wherein the expressed engineered peptide antigen is secreted and displayed on the cell surface as a component of a ligand specific for a TCR and evaluating the binding of the ligand to one or more TCRs. Upon identification of a particular TCR and/or peptide, the sequences can be sequenced, e.g., using next-generation sequencing such as Illumina HiSeq or MiSeq. In other aspects, the specific TCR and/or peptide can be identified through the detection of a barcode that is associated with a particular TCR and/or peptide.

In some embodiments, the disclosure provides an antigen screening method comprising expressing an engineered peptide antigen in a cell edited using a nucleic-acid directed nuclease (e.g., an RNA-directed nuclease such as a CRISPR nuclease). The expressed engineered peptide antigens are secreted and displayed on the cell surface as a component of a ligand specific for a TCR and evaluating the binding of the ligand to the one or more TCRs.

Expression of Edited Proteins

The engineered peptide antigens in the edited cells of the invention can be expressed from the edited nucleic acids using methods known in the art. In some embodiments, protein expression is constitutive. Constitutive expression covers both expression from nucleic acids that have been integrated into the genome and expression from nucleic acids that are located on episomal vectors. In some embodiments, expression is initiated by an inducible event. In some embodiments, edited nucleic acids that encode the engineered peptide antigens are operably connected to an initiator sequence that regulates expression of the engineered peptide antigen. Initiator sequences that can induce expression are known in the art and include inducible promoters. In some embodiments protein expression is induced. In some embodiments, protein expression occurs when the cell comprising a nucleic acid encoding the protein is incubated and no separate induction step is required.

Cell Libraries

Libraries of the invention include libraries of edited cells expressing unique engineered peptide antigens. The cells of the libraries are preferably edited using a nuclease, and more preferably using one or more nucleases (e.g., a nucleic acid-directed nuclease) in an automated multi-module cell editing instrument as described in more detail herein.

In some embodiments, the library provides edited cells with a high density of engineered peptide antigens immobilized on the cell surface. In some embodiments, the high density is accomplished by binding multiple engineered polypeptides expressed in a cell to a cell-surface binding target. In some embodiments, the number of engineered peptide antigens that are displayed per cell is greater than $10^3$, greater than $10^4$, greater than $10^5$, greater than $10^6$, greater than $10^7$, or greater than $10^8$ engineered peptide antigens per cell. In some embodiments, the immobilization peptide is a biotinylation peptide. The antigens displayed may be a single peptide antigen or two or more peptide antigens depending on the display strategy for the cells. In some embodiments, the immobilization peptide is a transmembrane protein. In some embodiments, the immobilization peptide comprises a GPI anchor. In some embodiments, the immobilization peptide is a peptide that is naturally present on the cell surface. In some embodiments, the immobilization peptide is a peptide that binds one or more molecules naturally present on the cell surface (e.g., surface carbohydrates or proteins on the cell surface).

In some embodiments, libraries of binding proteins may be evaluated or screened to identify and/or isolate variants that bind to one or more TCR targets. Methods of the invention may be designed to identify engineered peptide antigens that have affinities for a particular TCR greater than a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M. In some embodiments, methods of the invention may be designed to identify target peptide sequences that have affinities for a TCR greater than a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

Nuclease-Directed Genome Editing

In embodiments, the automated instrument described herein utilizes a nuclease-directed genome editing system for introducing edits to a population of cells allowing the engineering of proteins for cell surface display. Multiple different nuclease-based systems exist for providing edits into an organism's genome, and each can be used in either single editing systems, sequential editing systems (e.g., using different nuclease-directed systems sequentially to provide two or more genome edits in a cell) and/or recursive editing systems, (e.g., utilizing a single nuclease-directed system to introduce two or more genome edits in a cell). Exemplary nuclease-directed genome editing systems are described herein, although a person of skill in the art would recognize upon reading the present disclosure that other such editing instruments are also useful in the creation of populations of cells for cell surface display of engineered peptide antigens.

It should be noted that the automated editing instruments as set forth herein can use the nucleases for cleaving the genome, introduction of an edit into a target region, or both.

In particular aspects of the invention, the nuclease editing system is an inducible system that allows control of the timing of the editing. The ability to modulate nuclease activity can reduce off-target cleavage and facilitate precise genome engineering. Numerous different inducible systems can be used with the instrument and systems of the disclosure, as will be apparent to one skilled in the art upon reading the present disclosure.

In certain aspects, cleavage by a nuclease can be used with the instruments and systems of the invention to select cells with a genomic edit at a target region. For example, cells that have been subjected to a genomic edit that removes a particular nuclease recognition site (e.g., via homologous recombination) can be selected using the instruments described herein by exposing the cells to the nuclease following the edit. The DNA in the cells without the genome edit will be cleaved and subsequently will have limited growth and/or perish, whereas the cells that received the genome edit removing the nuclease recognition site will not be affected by the subsequent exposure to the nuclease.

In other aspects, cells for editing may be treated in some fashion to cleave the genome prior to introduction of the cells to the instrument, and the instrument used for automated introduction of desired genome edits in such cells. The initial cleavage can be performed by the same or a different enzyme than the one used for the initial cleavage event.

When the cell or population of cells comprising nucleic acid-guided nuclease encoding DNA is in the presence of the inducer molecule, expression of the nuclease can occur. For example, CRISPR-nuclease expression can be repressed in the presence of a repressor molecule. When the cell or population of cells comprising nucleic acid-guided nuclease encoding DNA is in the absence of a molecule that represses expression of the CRISPR-nuclease, expression of the CRISPR-nuclease can occur.

For example, inducible systems for editing using RNA-guided nuclease have been described, which use chemical induction to limit the temporal exposure of the cells to the RNA-guided nuclease. Dow, et al., Nature Biotechnology, 33:390-394 (2015); see also inducible lentiviral expression vectors available at Dharnmacon, GE Life Sciences, Lafayette, Colo. For additional techniques, see e.g., Campbell, Biochem J., 473(17): 2573-89 (2010).

In other examples, a virus-inducible nuclease can be used to induce gene editing in cells. See, e.g., Don, Antiviral Res., 130:50-57 (2016). In another example, for inducible expression of nucleic acid directed nucleases, variants can be switched on and off in human cells with 4-hydroxytamoxifen (4-HT) by fusing the nuclease with the hormone-binding domain of the estrogen receptor (ERT2). Liu, et al., Nature Chemical Biology, 12:980-87 (2016).

Zinc-finger nucleases (ZFNs) are artificial restriction enzymes generated by fusing a zinc finger DNA-binding domain to a DNA-cleavage domain. Zinc finger domains can be engineered to target specific target regions in an organism's genome. See, e.g., Urnov, et al., Nature Reviews Genetics 11, 636-646 (2010). Using the endogenous DNA repair machinery of an organism, ZFNs can be used to precisely alter a target region of the genome. ZFNs can be used to disable dominant mutations in heterozygous individuals by producing double-strand breaks ("DSBs") in the DNA in the mutant allele, which will, in the absence of a homologous template, be repaired by non-homologous end-joining (NHEJ). NHEJ repairs DSBs by joining the two ends together and usually produces no mutations, provided that the cut is clean and uncomplicated. Durai, et al., Nucleic Acids Res. 33 (18): 5978-90 (2005). This repair mechanism can be used to induce errors in the genome via indels or chromosomal rearrangement, often rendering the gene products coded at that location non-functional.

Alternatively, DNA can be introduced into a genome in the presence of exogenous double-stranded DNA fragments using homology dependent repair (HDR). The dependency of HDR on a homologous sequence to repair DSBs can be exploited by inserting a desired sequence within a sequence that is homologous to the flanking sequences of a DSB which, when used as a template by HDR system, would lead to the creation of the desired change within the genomic region of interest.

Multiple pairs of ZFNs can also be used to completely remove entire large segments of genomic sequence (Lee. et al., Genome Res. 20(1): 81-89 (2009). Expanded CAG/CTG repeat tracts are the genetic basis for more than a dozen inherited neurological disorders including Huntington's disease, myotonic dystrophy, and several spinocerebellar ataxias. It has been demonstrated in human cells that ZFNs can direct DSBs to CAG repeats and shrink the repeat from long pathological lengths to short, less toxic lengths (Mittelman, et al., PNAS USA, 106(24): 9607-12 (2009)).

Meganucleases were identified in the 1990s, and subsequent work has shown that they are particularly promising tools for genome editing, as they are able to efficiently induce homologous recombination, generate mutations in coding or non-coding regions of the genome, and alter reading frames of the coding regions of genomes. See, e.g., Epinat, et al., Nucleic Acids Research, 31(11):2952-62 (2003). The high specificity of meganucleases gives them a high degree of precision and much lower cell toxicity than other naturally occurring restriction enzymes.

Transcription activator-like effector nucleases (TALENs) are restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind to practically any desired DNA sequence, so when combined with a nuclease, DNA can be cut at specific locations. (See, e.g., Miller, et al., Nature Biotechnology, 29(2): 143-48 (2011); Boch, Nature Biotechnology, 29(2): 135-36 (2011)).

Like ZFNs, TALEN can edit genomes by inducing DSBs. The TALEN-created site-specific DSBs at target regions are repaired through NHEJ or HDR, resulting in targeted genome edits. TALENs can be used to introduce indels, rearrangements, or to introduce DNA into a genome through NHEJ in the presence of exogenous double-stranded DNA fragments.

A recent discovery for editing live cells involves nucleic acid-guided nuclease (e.g., RNA-guided nuclease) editing.

A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may reside within an editing cassette and is under the control of a constitutive promoter, or, in some embodiments and preferably, an inducible promoter as described below.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a protos-spacer mutation (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the methods disclosed herein allow for identification of edited cells in a background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the nucleic acid-guided nuclease editing system, a polynucleotide sequence encoding the nucleic acid-guided nuclease can be codon optimized for expression in particular cell types, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7 or other MADzymes. As with the guide nucleic acid, the nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as the inducible promoter controlling transcription of the guide nucleic acid; that is, a separate inducible promoter drives the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments the promoter driving transcription of the gRNA and the donor nucleic acid (or driving more than one gRNA/donor nucleic acid pair) is an inducible promoter and the promoter driving transcription of the nuclease is an inducible promoter as well. For additional information regarding editing cassettes, see U.S. Pat. No. 9,982,278, and U.S. Ser. Nos. 15/948,789; 15/116,616; 15/948,785; 16/056, 310; 16/275,439; and Ser. No. 16/275,465.

Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as possibly a lag in growth for the edited cells that do survive but must repair and recover following editing. However, once the edited cells have a chance to recover, the size of the colonies of the edited cells will eventually catch up to the size of the colonies of unedited cells. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may comprise—in addition to the at least one mutation relative to a target sequence—one or more PAM sequence alterations that mutate, delete or render inactive the PAM site in the target sequence. The PAM sequence alteration in the target sequence renders the PAM site "immune" to the nucleic acid-guided nuclease and protects the target sequence from further editing in subsequent rounds of editing if the same nuclease is used.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the nucleic acid-guided nuclease editing system may be inducible. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others. In the present methods used in the modules and instruments described herein, it is preferred that at least one of the nucleic acid-guided nuclease editing components (e.g., the nuclease and/or the gRNA) is under the control of a promoter that is activated by a rise in temperature, as such a promoter allows for the promoter to be activated by an increase in temperature, and de-activated by a decrease in temperature, thereby "turning off" the editing process. Thus, in the scenario of a promoter that is de-activated by a decrease in temperature, editing in the cell can be turned off without having to change media; to remove, e.g., an inducible biochemical in the medium that is used to induce editing.

Figure 4A:
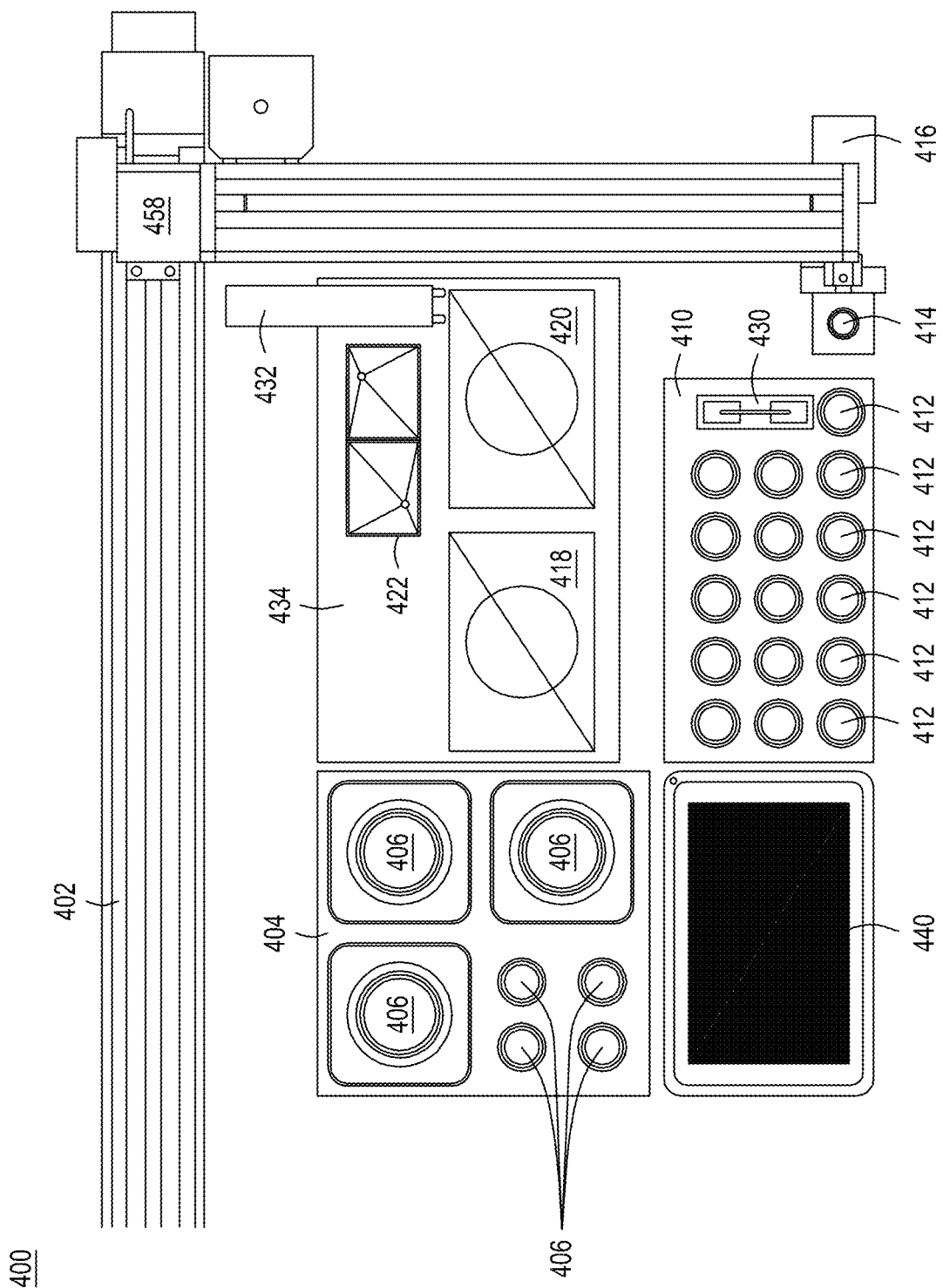

Automated Cell Editing Instruments and Modules to Create Cell Surface Display Libraries Automated Cell Editing Instruments FIG. 4A depicts an exemplary automated multi-module cell processing instrument 400 to, e.g., perform one of the exemplary workflows described above, as well as additional exemplary modules. The instrument 400, for example, may be and preferably is designed as a desktop instrument for use within a laboratory environment. The instrument 400 may incorporate a mixture of reusable and disposable elements for performing various staged processes in conducting automated genome cleavage and/or editing in cells. Illustrated is a gantry 402, providing an automated mechanical motion system (actuator) (not shown) that supplies XYZ axis motion control to, e.g., an automated liquid handling system 458 including, e.g., an air displacement pipette as well as modules of the automated multi-module cell processing instrument 400. In some automated multi-module cell processing instruments, the air displacement pipettor 432 is moved by gantry 402 and the various modules and reagent cartridges remain stationary; however, in other embodiments, the liquid handling system may stay stationary while the various modules are moved. Also included in the automated multi-module cell processing instrument 400 is reagent cartridge 410 comprising reservoirs 412 and transformation module 430, as well as a wash cartridge 404 comprising reservoirs 406. The wash cartridge 404 may be configured to accommodate large tubes, for example, wash solutions, or solutions that are used often throughout an iterative process. In one example, wash cartridge 404 may be configured to remain in place when two or more reagent cartridges 410 are sequentially used and replaced. Although reagent cartridge 410 and wash cartridge 404 are shown in FIG. 4A as separate cartridges, the contents of wash cartridge 404 may be incorporated into reagent cartridge 410. Note in this embodiment transformation module 430 is contained within reagent cartridge 410; however, in alternative embodiments transformation module 430 is contained within its own module or may be part of another module, such as a growth module.

The wash and reagent cartridges 404 and 410 in some implementations, are disposable kits provided for use in the automated multi-module cell editing instrument 400. For example, a user may open and position each of the reagent cartridge 410 and the wash cartridge 404 within a chassis of the automated multi-module cell editing instrument prior to activating cell processing.

Also illustrated is the robotic handling system 458 including the gantry 402 and air displacement pipettor 432. In some examples, the robotic handling system 458 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 432.

Components of the cartridges 404, 410, in some implementations, are marked with machine-readable indicia (not shown), such as bar codes, for recognition by the robotic handling system 458. For example, the robotic handling system 458 may scan containers within each of the cartridges 404, 410 to confirm contents. In other implementations, machine-readable indicia may be marked upon each cartridge 404, 410, and the processing system 426 (shown in FIG. 4D) of the automated multi-module cell editing instrument 400 may identify a stored materials map based upon the machine-readable indicia. The exemplary automated multi-module cell processing instrument 400 of FIG. 4A further comprises a cell growth module 434. (Note, all modules recited briefly here are described in detail below.) In the embodiment illustrated in FIG. 4A, the cell growth module 434 comprises two cell growth vials 418, 420 (described in greater detail below in relation to FIGS. 5A-5D) as well as a cell concentration module 422 (described in detail in relation to FIGS. 6A-6F). In alternative embodiments, the cell concentration module 422 may be separate from cell growth module 434, e.g., in a separate, dedicated module. Also illustrated as part of the automated multi-module cell processing instrument 400 of FIG. 4A is an optional enrichment module 440, served by, e.g., robotic handing system 458 and air displacement pipettor 432. Also seen are an optional nucleic acid assembly/desalting module 414 comprising a reaction chamber or tube receptacle (not shown) and a magnet 416 to allow for purification of nucleic acids using, e.g., magnetic solid phase reversible immobilization (SPRI) beads (Applied Biological Materials Inc., Richmond, BC). The cell growth module, cell concentration module, transformation module, enrichment module, reagent cartridge, and nucleic acid assembly module are described in greater detail below.

Figure 4B:
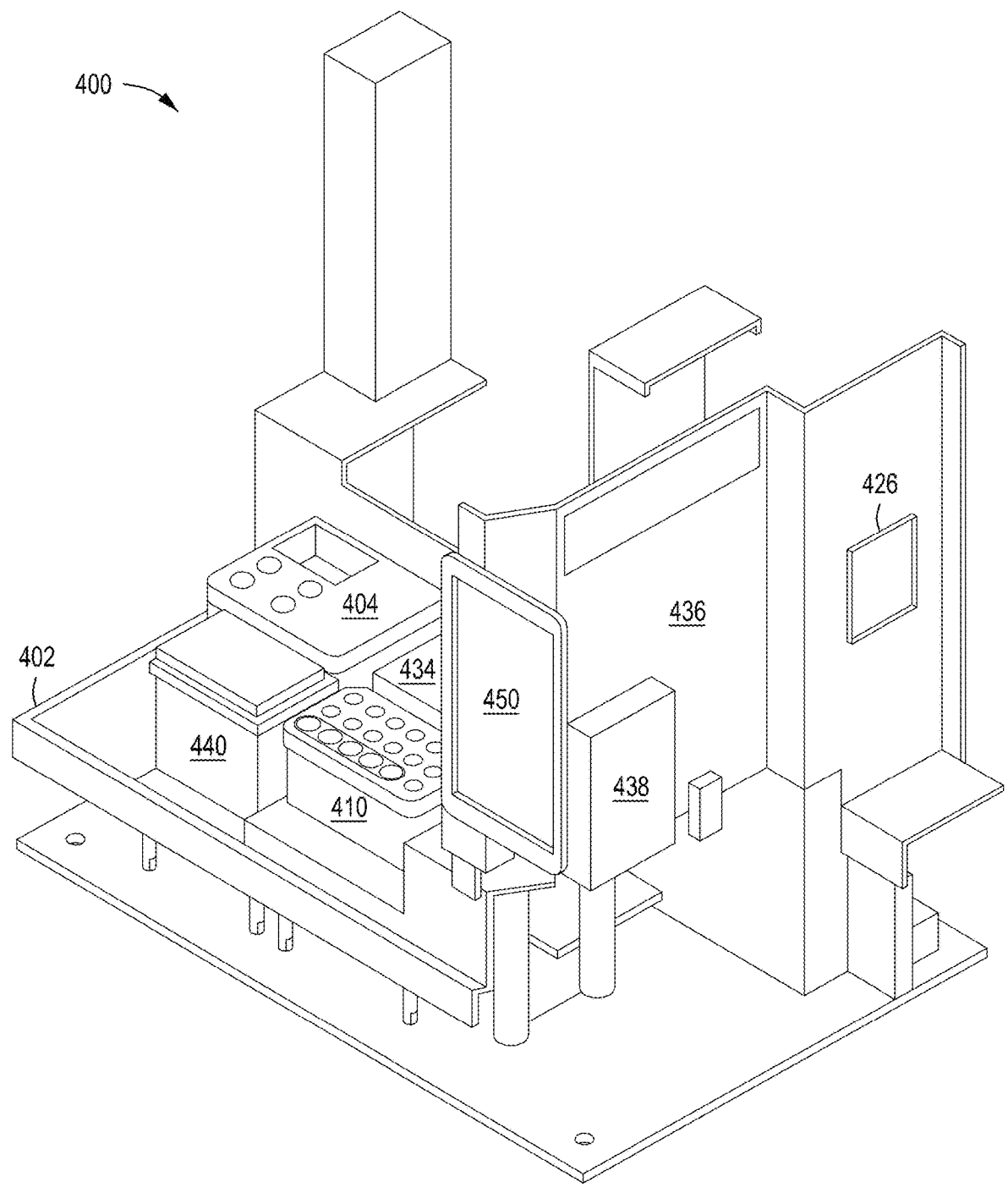

FIG. 4B is a plan view of the front of the exemplary multi-module cell processing instrument 400 depicted in FIG. 4A. Cartridge-based source materials (such as in reagent cartridge 410), for example, may be positioned in designated areas on a deck 402 of the instrument 400 for access by a robotic handling instrument (not shown in this figure). As illustrated in FIG. 4B, the deck 402 may include a protection sink such that contaminants spilling, dripping, or overflowing from any of the modules of the instrument 400 are contained within a lip of the protection sink. In addition to reagent cartridge 410, also seen in FIG. 4B is wash cartridge 404, optional enrichment module 440, and a portion of growth module 434. Also seen in this view is touch screen display 450, transformation module controls 438, electronics rack 436, and processing system 426.

FIGS. 4C through 4D illustrate multi-module cell processing instruments 480 comprising chassis 490 for use in desktop versions the cell editing instrument 480. For example, the chassis 490 may have a width of about 24-48 inches, a height of about 24-48 inches and a depth of about 24-48 inches. Chassis 490 may be and preferably is designed to hold multiple modules and disposable supplies used in automated cell processing. Further, chassis 490 may mount a robotic handling system 458 for moving materials between modules.

As illustrated, the chassis 490 includes a cover having a handle 454 and hinges 456a-456c for lifting the cover and accessing the interior of the chassis 490. A cooling grate 464 allows for air flow via an internal fan (not shown). Further, the chassis 490 is lifted by adjustable feet 470 (feet 470a-c are shown). The feet 470a-470c, for example, may provide additional air flow beneath the chassis 490. A control button 466, in some embodiments, allows for single-button automated start and/or stop of cell processing within the chassis 490.

Inside the chassis 490, in some implementations, a robotic handling system 458 is disposed along a gantry 402 above materials cartridges 404 and 410. Control circuitry, liquid handling tubes, air pump controls, valves, thermal units (e.g., heating and cooling units) and other control mechanisms, in some embodiments, are disposed below a deck of the chassis 490, in a control box region 468. Also seen in FIG. 4D is enrichment module 440 and nucleic acid assembly module 414 comprising a magnet 416

Although not illustrated, in some embodiments a display screen may be positioned on the front face of the chassis 490, for example covering a portion of the cover (e.g., see FIG. 4B). The display screen may provide information to the user regarding the processing status of the automated multi-module cell editing instrument. In another example, the display screen may accept inputs from the user for conducting the cell processing.

The Rotating Cell Growth Module

Figure 5A:
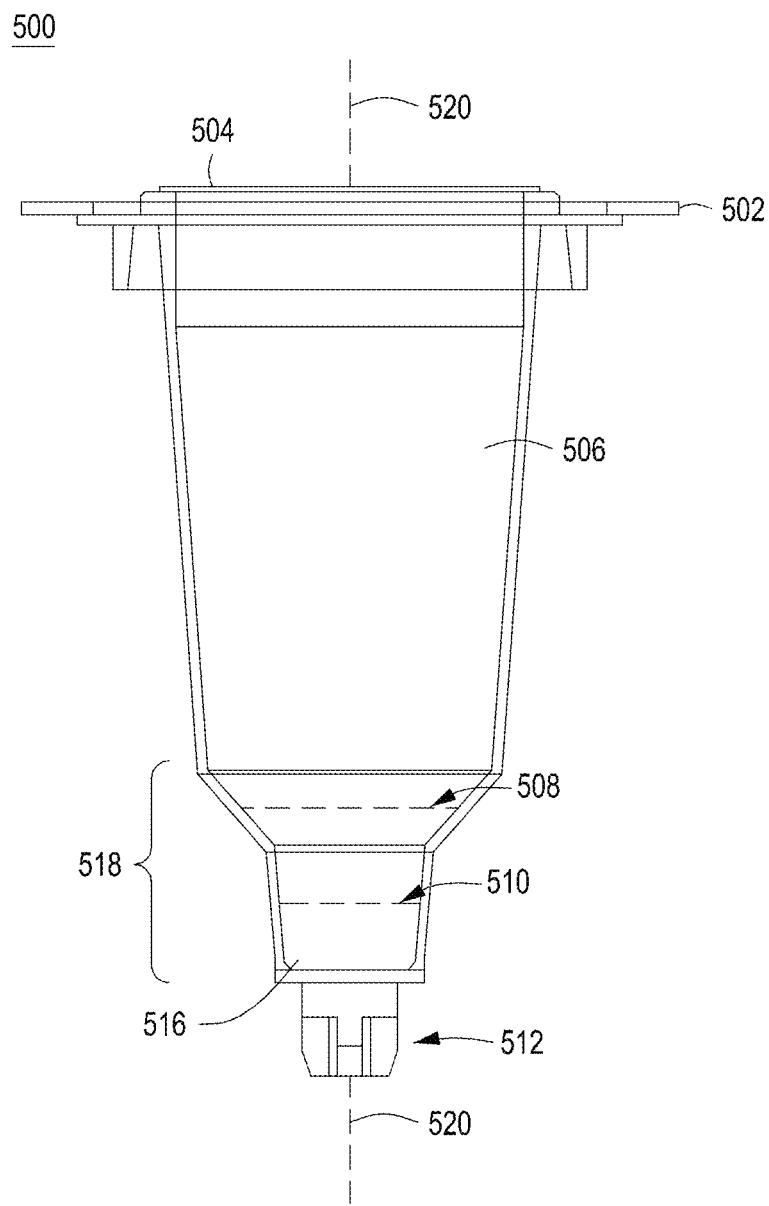
FIG. 5A depicts one embodiment of a rotating growth vial for use with the cell growth module described herein.

FIG. 5A shows one embodiment of a rotating growth vial 500 for use with the cell growth device described herein. The rotating growth vial is an optically-transparent container having an open end 504 for receiving liquid media and cells, a central vial region 506 that defines the primary container for growing cells, a tapered-to-constricted region 518 defining at least one light path 510, a closed end 516, and a drive engagement mechanism 512. The rotating growth vial has a central longitudinal axis 520 around which the vial rotates, and the light path 510 is generally perpendicular to the longitudinal axis of the vial. The first light path 510 is positioned in the lower constricted portion of the tapered-to-constricted region 518. Optionally, some embodiments of the rotating growth vial 500 have a second light path 508 in the tapered region of the tapered-to-constricted region 518. Both light paths in this embodiment are positioned in a region of the rotating growth vial that is constantly filled with the cell culture (cells+growth media) and is not affected by the rotational speed of the growth vial. The first light path 510 is shorter than the second light path 508 allowing for sensitive measurement of OD values when the OD values of the cell culture in the vial are at a high level (e.g., later in the cell growth process), whereas the second light path 508 allows for sensitive measurement of OD values when the OD values of the cell culture in the vial are at a lower level (e.g., earlier in the cell growth process). Also shown is lip 502, which allows the rotating growth vial to be seated in a growth module (not shown) and further allows for easy handling for the user.

In some configurations of the rotating growth vial, the rotating growth vial has two or more "paddles" or interior features disposed within the rotating growth vial, extending from the inner wall of the rotating growth vial toward the center of the central vial region. In some aspects, the width of the paddles or features varies with the size or volume of the rotating growth vial, and may range from $\frac{1}{20}$ to just over $\frac{1}{3}$ the diameter of the rotating growth vial, or from $\frac{1}{15}$ to $\frac{1}{4}$ the diameter of the rotating growth vial, or from $\frac{1}{10}$ to $\frac{1}{5}$ the diameter of the rotating growth vial. In some aspects, the length of the paddles varies with the size or volume of the rotating growth vial, and may range from $\frac{4}{5}$ to $\frac{1}{4}$ the length of the main body of the rotating growth vial, or from $\frac{3}{4}$ to $\frac{1}{3}$ the length of the main body of the rotating growth vial, or from $\frac{1}{2}$ to $\frac{1}{3}$ the length of the main body of the rotating growth vial. In other aspects, there may be concentric rows of raised features disposed on the inner surface of the main body of the rotating growth vial arranged horizontally or vertically; and in other aspects, there may be a spiral configuration of raised features disposed on the inner surface of the main body of the rotating growth vial. In alternative aspects, the concentric rows of raised features or spiral configuration may be disposed upon a post or center structure of the rotating growth vial. Though described above as having two paddles, the rotating growth vial may comprise 3, 4, 5, 6 or more paddles, and up to 20 paddles. The number of paddles will depend upon, e.g., the size or volume of the rotating growth vial. The paddles may be arranged symmetrically as single paddles extending from the inner wall of the vial into the interior of the vial, or the paddles may be symmetrically arranged in groups of 2, 3, 4 or more paddles in a group (for example, a pair of paddles opposite another pair of paddles) extending from the inner wall of the vial into the interior of the vial. In another embodiment, the paddles may extend from the middle of the rotating growth vial out toward the wall of the rotating growth vial, from, e.g., a post or other support structure in the interior of the rotating growth vial.

The drive engagement mechanism 512 engages with a motor (not shown) to rotate the vial. In some embodiments, the motor drives the drive engagement mechanism 512 such that the rotating growth vial is rotated in one direction only, and in other embodiments, the rotating growth vial is rotated in a first direction for a first amount of time or periodicity, rotated in a second direction (i.e., the opposite direction) for a second amount of time or periodicity, and this process may be repeated so that the rotating growth vial (and the cell culture contents) are subjected to an oscillating motion. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial may be oscillated at a first periodicity (e.g., every 60 seconds), and then a later stage of cell growth the rotating growth vial may be oscillated at a second periodicity (e.g., every one second) different from the first periodicity.

The rotating growth vial 500 may be reusable or, preferably, the rotating growth vial is consumable. In some embodiments, the rotating growth vial is consumable and is presented to the user pre-filled with growth medium, where the vial is hermetically sealed at the open end 504 with a foil seal. A medium-filled rotating growth vial packaged in such a manner may be part of a kit for use with a stand-alone cell growth device or with a cell growth module that is part of an automated multi-module cell processing instrument. To introduce cells into the vial, a user need only pipette up a desired volume of cells and use the pipette tip to punch through the foil seal of the vial. Open end 504 may optionally include an extended lip 502 to overlap and engage with the cell growth device (not shown). In automated systems, the rotating growth vial 500 may be tagged with a barcode or other identifying means that can be read by a scanner or camera that is part of the automated system (not shown).

The volume of the rotating growth vial 500 and the volume of the cell culture (including growth medium) may vary greatly, but the volume of the rotating growth vial 500 must be large enough for the cell culture in the growth vial to get proper aeration while the vial is rotating. In practice, the volume of the rotating growth vial 500 may range from 1-250 ml, 2-100 ml, from 5-80 ml, 10-50 ml, or from 12-35 ml. Likewise, the volume of the cell culture (cells+growth media) should be appropriate to allow proper aeration in the rotating growth vial. Thus, the volume of the cell culture should be approximately 10-85% of the volume of the growth vial or from 20-60% of the volume of the growth vial. For example, for a 35 ml growth vial, the volume of the cell culture would be from about 4 ml to about 27 ml, or from 7 ml to about 21 ml.

The rotating growth vial 500 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include glass, polyvinyl chloride, polyethylene, polyamide, polyethylene, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 5B:
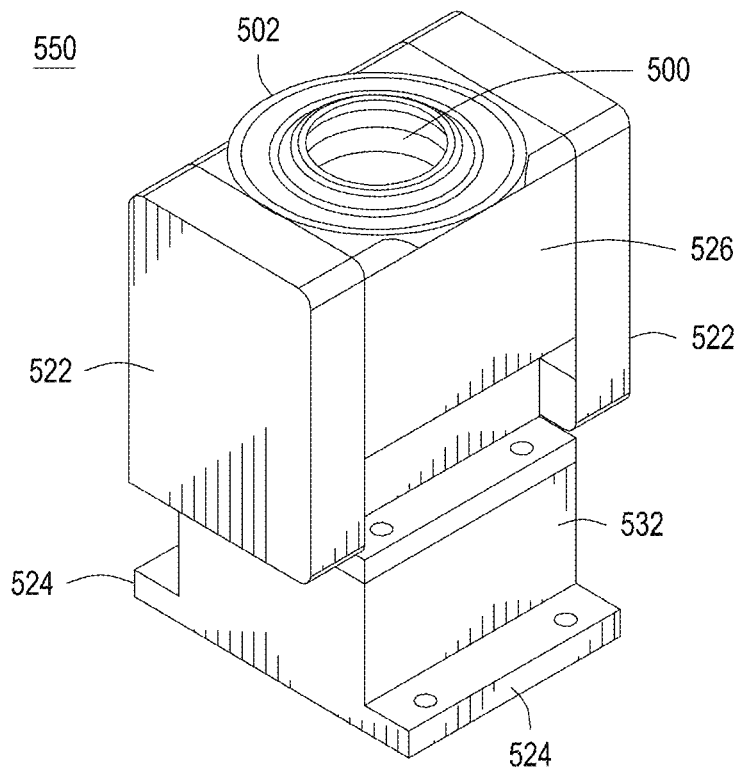
FIG. 5B illustrates a perspective view of one embodiment of a rotating growth vial in a cell growth module.
Figure 5C:
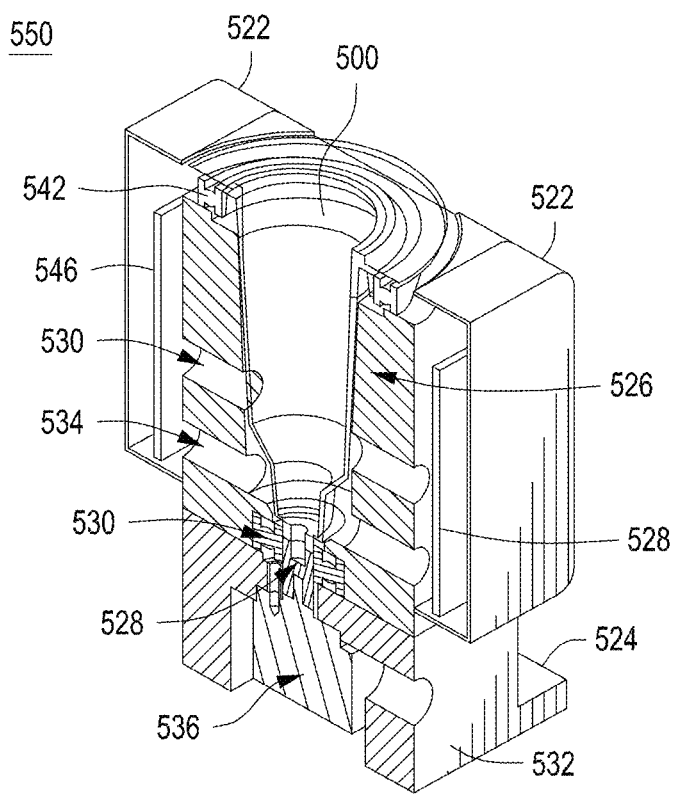
FIG. 5C depicts a cut-away view of the cell growth module from FIG. 5B.
Figure 5D:
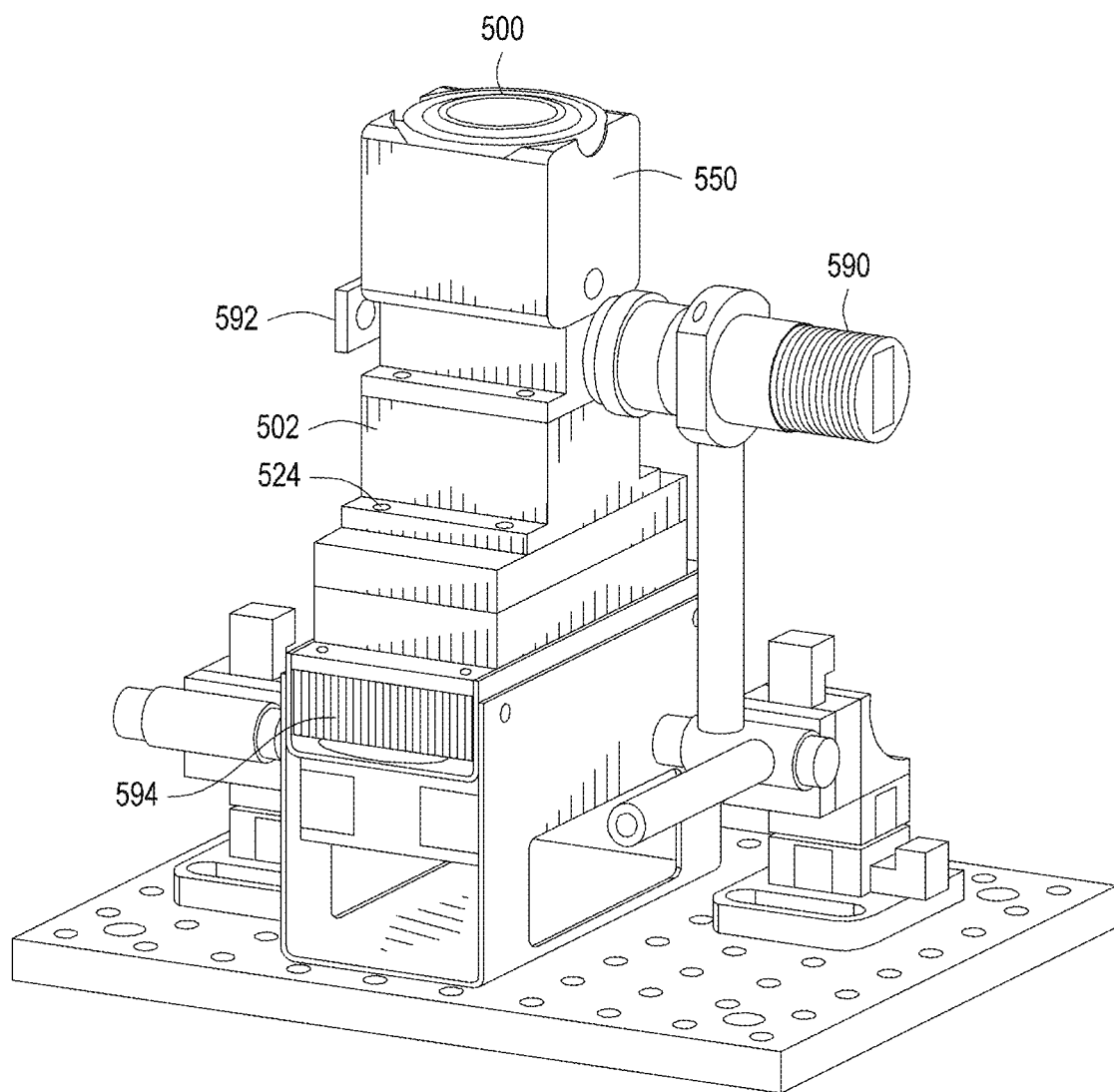
FIG. 5D illustrates the cell growth module of FIG. 5B coupled to LED, detector, and temperature regulating components.

FIGS. 5B-5D show an embodiment of a cell growth module 550 comprising a rotating growth vial 500. FIG. 5B is a perspective view of one embodiment of a cell growth device 550. FIG. 5C depicts a cut-away view of the cell growth device 550 from FIG. 5B. In both figures, the rotating growth vial 500 is seen positioned inside a main housing 526 with the extended lip 502 of the rotating growth vial 500 extending above the main housing 526. Additionally, end housings 522, a lower housing 532, and flanges 524 are indicated in both figures. Flanges 524 are used to attach the cell growth device to heating/cooling means or other structure (not shown). FIG. 5C depicts additional detail. In FIG. 5C, upper bearing 542 and lower bearing 530 are shown positioned in main housing 526. Upper bearing 542 and lower bearing 530 support the vertical load of rotating growth vial 500. Lower housing 532 contains the drive motor 536. The cell growth device of FIG. 5C comprises two light paths: a primary light path 534, and a secondary light path 530. Light path 534 corresponds to light path 510 positioned in the constricted portion of the tapered-to-constricted portion of the rotating growth vial, and light path 530 corresponds to light path 508 in the tapered portion of the tapered-to-constricted portion of the rotating growth vial. Light paths 510 and 508 are not shown in FIG. 5C but may be seen in, e.g., FIG. 5A. In addition to light paths 534 and 530, there is an emission board 528 to illuminate the light path(s), and detector board 546 to detect the light after the light travels through the cell culture liquid in the rotating growth vial.

The motor 536 used to rotate the rotating growth vial 500 in some embodiments is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 506 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 526, end housings 522 and lower housing 532 of the cell growth device 550 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial is envisioned in some embodiments to be reusable but preferably is consumable, the other components of the cell growth device 550 are preferably reusable and can function as a stand-alone benchtop device or, as here, as a module in a multi-module cell processing system.

The processor (not shown) of the cell growth system may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor of the cell growth system may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth system, where the second spectrophotometer is used to read a blank at designated intervals.

FIG. 5D illustrates a cell growth device as part of an assembly comprising the cell growth device of FIG. 5B coupled to light source 590, detector 592, and thermal components 594. The rotating growth vial 500 is inserted into the cell growth device. Components of the light source 590 and detector 592 (e.g., such as a photodiode with gain control to cover 5-log) are coupled to the main housing of the cell growth device. The lower housing 532 that houses the motor that rotates the rotating growth vial is illustrated, as is one of the flanges 524 that secures the cell growth device to the assembly. Also illustrated is a Peltier device or thermoelectric cooler 594. In this embodiment, thermal control is accomplished by attachment and electrical integration of the cell growth device 500 to the thermal device 594 via the flange 504 on the base of the lower housing 532. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 500 is controlled to approximately +/−0.5° C.

In certain embodiments, a rear-mounted power entry module contains the safety fuses and the on-off switch, which when switched on powers the internal AC and DC power supplies (not shown) activating the processor. Measurements of optical densities (OD) at programmed time intervals are accomplished using a 600 nm Light Emitting Diode (LED) (not shown) that has been columnated through an optic into the lower constricted portion of the rotating growth vial which contains the cells of interest. The light continues through a collection optic to the detection system which consists of a (digital) gain-controlled silicone photodiode. Generally, optical density is normally shown as the absolute value of the logarithm with base 10 of the power transmission factors of an optical attenuator: OD=−log 10(Power out/Power in). Since OD is the measure of optical attenuation—that is, the sum of absorption, scattering, and reflection—the cell growth device OD measurement records the overall power transmission, so as the cells grow and become denser in population the OD (the loss of signal) increases. The OD system is pre-calibrated against OD standards with these values stored in an on-board memory accessible by the measurement program.

In use, cells are inoculated (cells can be pipetted, e.g., from an automated liquid handling system or by a user) into pre-filled growth media of a rotating growth vial by piercing though the foil seal. The programmed software of the cell growth device sets the control temperature for growth, typically 30° C., then slowly starts the rotation of the rotating growth vial. The cell/growth media mixture slowly moves vertically up the wall due to centrifugal force allowing the rotating growth vial to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 550 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 on minutes. While the cell growth device has been described in the context of measuring the optical density (OD) of a growing cell culture, it should, however, be understood by a skilled artisan given the teachings of the present specification that other cell growth parameters can be measured in addition to or instead of cell culture OD. For example, spectroscopy using visible, UV, or near infrared (NIR) light allows monitoring the concentration of nutrients and/or wastes in the cell culture. Additionally, spectroscopic measurements may be used to quantify multiple chemical species simultaneously. Nonsymmetric chemical species may be quantified by identification of characteristic absorbance features in the NIR. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and can be used for thicker sample. FT-mid-IR (MIR) provides information that is more easily discernible as being specific for certain analytes as these wavelengths are closer to the fundamental IR absorptions. FT-Raman is advantageous when interference due to water is to be minimized. Other spectral properties can be measured via, e.g., dielectric impedance spectroscopy, visible fluorescence, fluorescence polarization, or luminescence. Additionally, the cell growth device may include additional sensors for measuring, e.g., dissolved oxygen, carbon dioxide, pH, conductivity, and the like.

The Cell Concentration Module

FIGS. 6A-6I depict variations on one embodiment of a cell concentration/buffer exchange cassette and module that utilizes tangential flow filtration. One embodiment of a cell concentration device described herein operates using tangential flow filtration (TFF), also known as crossflow filtration, in which the majority of the feed flows tangentially over the surface of the filter thereby reducing cake (retentate) formation as compared to dead-end filtration, in which the feed flows into the filter. Secondary flows relative to the main feed are also exploited to generate shear forces that prevent filter cake formation and membrane fouling thus maximizing particle recovery, as described below.

Figure 6A:
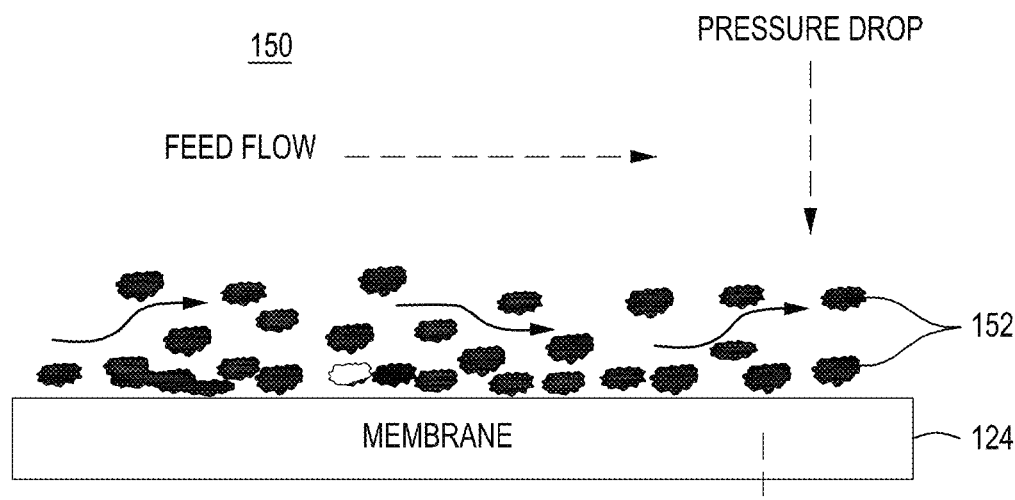
FIG. 6A is a model of tangential flow filtration used in the TFF device presented herein.

The TFF device described herein was designed to take into account two primary design considerations. First, the geometry of the TFF device leads to filtering the cell culture over a large surface area so as to minimize processing time. Second, the design of the TFF device is configured to minimize filter fouling. FIG. 6A is a general model 150 of tangential flow filtration. The TFF device operates using tangential flow filtration, also known as cross-flow filtration. FIG. 6A shows cells flowing over a membrane 124, where the feed flow of the cells 152 in medium or buffer is parallel to the membrane 124. TFF is different from dead-end filtration where both the feed flow and the pressure drop are perpendicular to a membrane or filter.

Figure 6B:
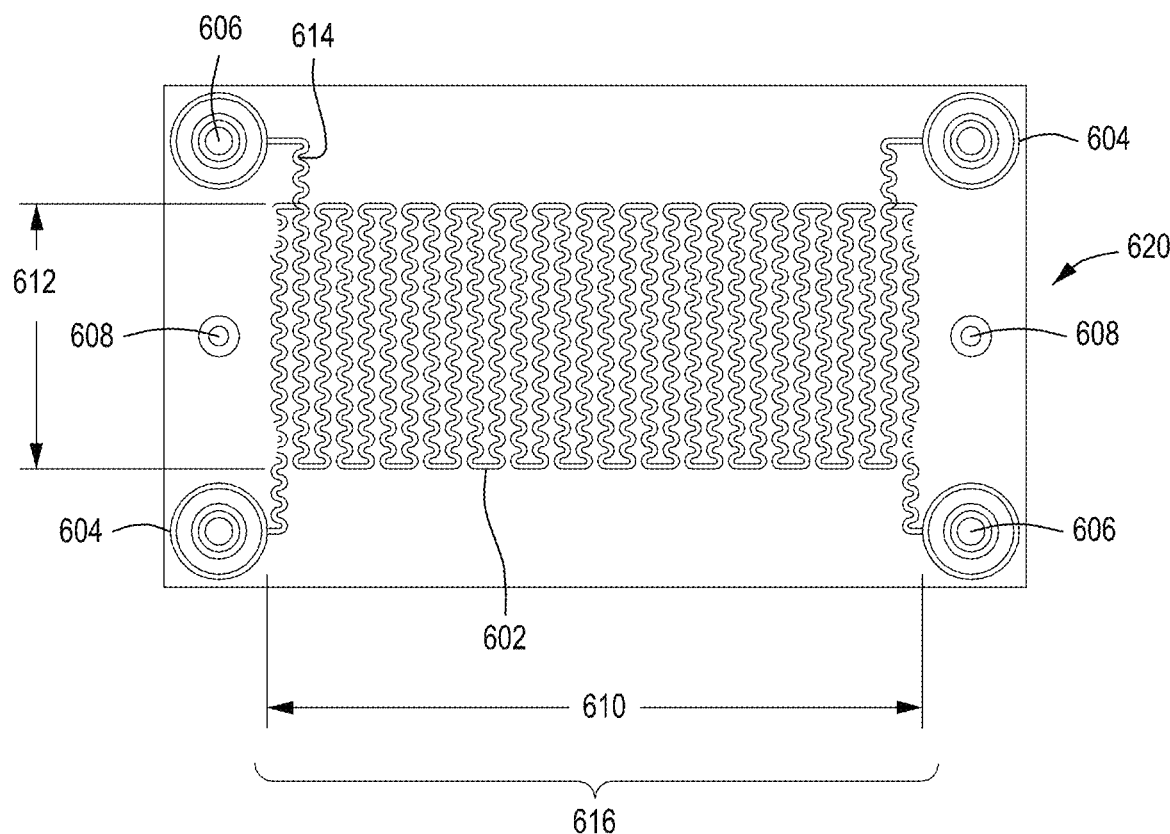
FIG. 6B depicts a top view of a lower member of one embodiment of an exemplary TFF device.

FIG. 6B depicts a top view of the lower member of one embodiment of a TFF device/module providing tangential flow filtration. As can be seen in the embodiment of the TFF device of FIG. 6B, TFF device 600 comprises a channel structure 616 comprising a flow channel 602*b* through which a cell culture is flowed. The channel structure 616 comprises a single flow channel 602*b* that is horizontally bifurcated by a membrane (not shown) through which buffer or medium may flow, but cells cannot. This particular embodiment comprises an undulating serpentine geometry 614 (i.e., the small "wiggles" in the flow channel 602) and a serpentine "zig-zag" pattern where the flow channel 602 crisscrosses the device from one end at the left of the device to the other end at the right of the device. The serpentine pattern allows for filtration over a high surface area relative to the device size and total channel volume, while the undulating contribution creates a secondary inertial flow to enable effective membrane regeneration preventing membrane fouling. Although an undulating geometry and serpentine pattern are exemplified here, other channel configurations may be used as long as the channel can be bifurcated by a membrane, and as long as the channel configuration provides for flow through the TFF module in alternating directions. In addition to the flow channel 602b, portals 604 and 606 as part of the channel structure 616 can be seen, as well as recesses 608. Portals 604 collect cells passing through the channel on one side of a membrane (not shown) (the "retentate"), and portals 606 collect the medium ("filtrate" or "permeate") passing through the channel on the opposite side of the membrane (not shown). In this embodiment, recesses 608 accommodate screws or other fasteners (not shown) that allow the components of the TFF device to be secured to one another.

The length 610 and width 612 of the channel structure 616 may vary depending on the volume of the cell culture to be grown and the optical density of the cell culture to be concentrated. The length 610 of the channel structure 616 typically is from 1 mm to 300 mm, or from 50 mm to 250 mm, or from 60 mm to 200 mm, or from 70 mm to 150 mm, or from 80 mm to 100 mm. The width of the channel structure 616 typically is from 1 mm to 120 mm, or from 20 mm to 100 mm, or from 30 mm to 80 mm, or from 40 mm to 70 mm, or from 50 mm to 60 mm. The cross-section configuration of the flow channel 102 may be round, elliptical, oval, square, rectangular, trapezoidal, or irregular. If square, rectangular, or another shape with generally straight sides, the cross section may be from about 10 μm to 1000 μm wide, or from 200 μm to 800 μm wide, or from 300 μm to 700 μm wide, or from 400 μm to 600 μm wide; and from about 10 μm to 1000 μm high, or from 200 μm to 800 μm high, or from 300 μm to 700 μm high, or from 400 μm to 600 μm high. If the cross section of the flow channel 602 is generally round, oval or elliptical, the radius of the channel may be from about 50 μm to 1000 μm in hydraulic radius, or from 5 μm to 800 μm in hydraulic radius, or from 200 μm to 700 μm in hydraulic radius, or from 300 μm to 600 μm wide in hydraulic radius, or from about 200 to 500 μm in hydraulic radius.

When looking at the top view of the TFF device/module of FIG. 6B, note that there are two retentate portals 604 and two filtrate portals 606, where there is one of each type portal at both ends (e.g., the narrow edge) of the device 600. In other embodiments, retentate and filtrate portals can on the same surface of the same member (e.g., upper or lower member), or they can be arranged on the side surfaces of the assembly. Unlike other TFF devices that operate continuously, the TFF device/module described herein uses an alternating method for concentrating cells. The overall work flow for cell concentration using the TFF device/module involves flowing a cell culture or cell sample tangentially through the channel structure. The membrane bifurcating the flow channels retains the cells on one side of the membrane and allows unwanted medium or buffer to flow across the membrane into a filtrate side (e.g, lower member 620) of the device. In this process, a fixed volume of cells in medium or buffer is driven through the device until the cell sample is collected into one of the retentate portals 604, and the medium/buffer that has passed through the membrane is collected through one or both of the filtrate portals 606. All types of prokaryotic and eukaryotic cells—both adherent and non-adherent cells—can be grown in the TFF device. Adherent cells may be grown on beads or other cell scaffolds suspended in medium that flow through the TFF device.

In the cell concentration process, passing the cell sample through the TFF device and collecting the cells in one of the retentate portals 604 while collecting the medium in one of the filtrate portals 606 is considered "one pass" of the cell sample. The transfer between retentate reservoirs "flips" the culture, The retentate and filtrate portals collecting the cells and medium, respectively, for a given pass reside on the same end of TFF device/module 600 with fluidic connections arranged so that there are two distinct flow layers for the retentate and filtrate sides, but if the retentate portal 604 resides on the upper member of device/module 600 (that is, the cells are driven through the channel above the membrane and the filtrate (medium) passes to the portion of the channel below the membrane), the filtrate portal 606 will reside on the lower member of device/module 100 and vice versa (that is, if the cell sample is driven through the channel below the membrane, the filtrate (medium) passes to the portion of the channel above the membrane). This configuration can be seen more clearly in FIGS. 6C-6D, where the retentate flows 660 from the retentate portals 604 and the filtrate flows 670 from the filtrate portals 606.

At the conclusion of a "pass" in the growth concentration process, the cell sample is collected by passing through the retentate portal 604 and into the retentate reservoir (not shown). To initiate another "pass", the cell sample is passed again through the TFF device, this time in a flow direction that is reversed from the first pass. The cell sample is collected by passing through the retentate portal 604 and into retentate reservoir (not shown) on the opposite end of the device/module from the retentate portal 604 that was used to collect cells during the first pass. Likewise, the medium/buffer that passes through the membrane on the second pass is collected through the filtrate portal 606 on the opposite end of the device/module from the filtrate portal 606 that was used to collect the filtrate during the first pass, or through both portals. This alternating process of passing the retentate (the concentrated cell sample) through the device/module is repeated until the cells have been concentrated to a desired volume, and both filtrate portals can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell concentration may (and typically do) take place simultaneously.

Figure 6C:
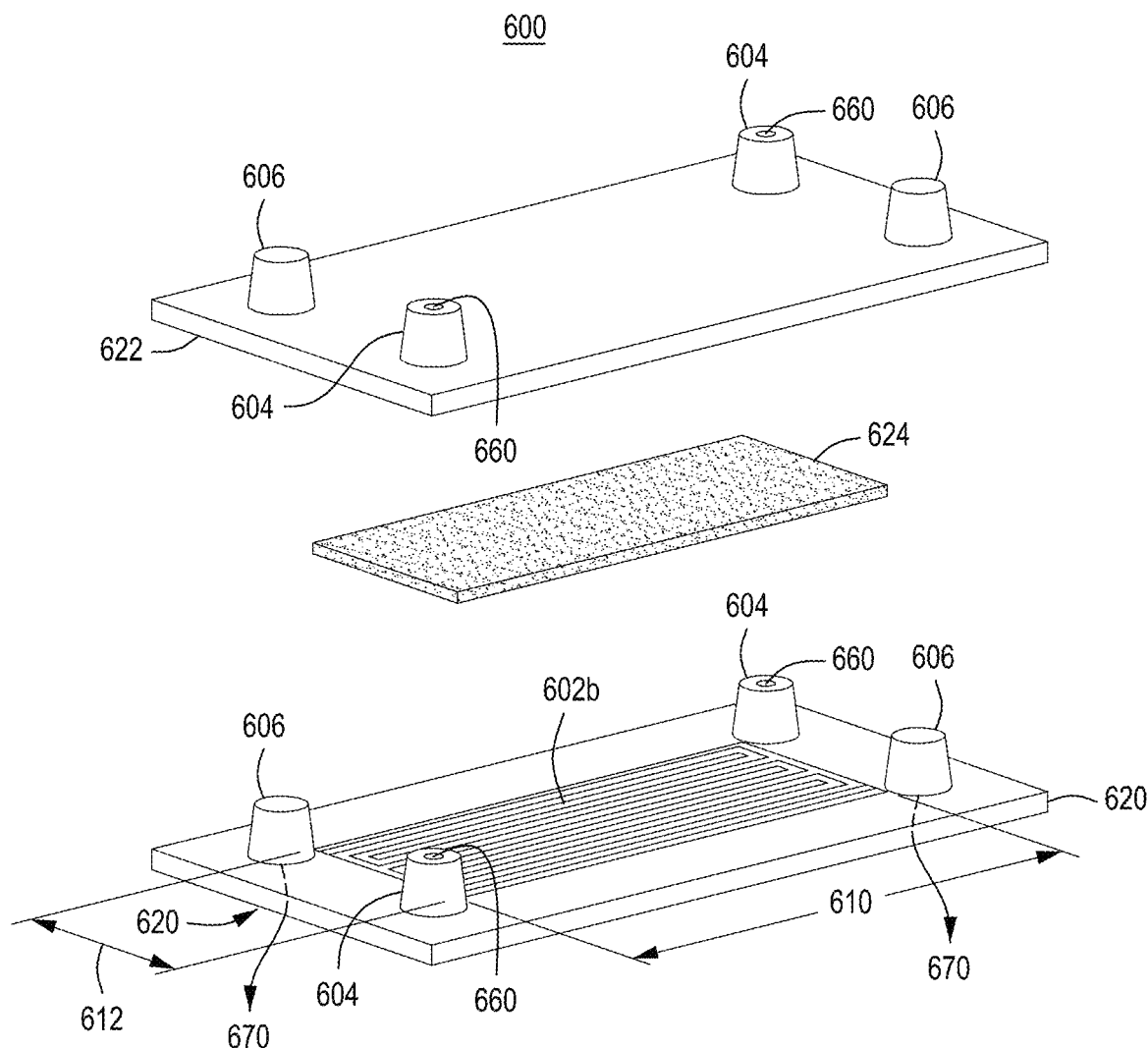
FIG. 6C depicts a top view of upper and lower members and a membrane of an exemplary TFF device.

FIG. 6C depicts a top view of upper (622) and lower (620) members of an exemplary TFF module. Again, portals 604 and 606 are seen. As noted above, recesses—such as the recesses 608 seen in FIG. 6B—provide a means to secure the components (upper member 622, lower member 620, and membrane 624) of the TFF device/membrane to one another during operation via, e.g., screws or other like fasteners. However, in alternative embodiments an adhesive, such as a pressure sensitive adhesive, or ultrasonic welding, or solvent bonding, may be used to couple the upper member 622, lower member 620, and membrane 624 together. Indeed, one of ordinary skill in the art given the guidance of the present disclosure can find yet other configurations for coupling the components of the TFF device, such as e.g., clamps; mated fittings disposed on the upper and lower members; combination of adhesives, welding, solvent bonding, and mated fittings; and other such fasteners and couplings.

Note that there is one retentate portal and one filtrate portal on each "end" (e.g., the narrow edges) of the TFF device/module. The retentate and filtrate portals on the left side of the device/module will collect cells (flow path at 660) and medium (flow path at 670), respectively, for the same pass. Likewise, the retentate and filtrate portals on the right side of the device/module will collect cells (flow path at 660) and medium (flow path at 670), respectively, for the same pass. In this embodiment, the retentate is collected from portals 604 on the top surface of the TFF device, and filtrate is collected from portals 606 on the bottom surface of the device. The cells are maintained in the TFF flow channel above the membrane 624, while the filtrate (medium) flows through membrane 624 and then through portals 606; thus, the top/retentate portals and bottom/filtrate portals configuration is practical. It should be recognized, however, that other configurations of retentate and filtrate portals may be implemented such as positioning both the retentate and filtrate portals on the side (as opposed to the top and bottom surfaces) of the TFF device. In FIG. 6C, the channel structure 602b can be seen on the bottom member 620 of the TFF device 600. However, in other embodiments, retentate and filtrate portals can reside on the same of the TFF device.

Also seen in FIG. 6C is membrane or filter 624. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 5 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching. The TFF device shown in FIGS. 6C and 6D do not show a seat in the upper 612 and lower 620 members where the filter 624 can be seated or secured (for example, a seat half the thickness of the filter in each of upper 612 and lower 620 members); however, such a seat is contemplated in some embodiments.

Figure 6D:
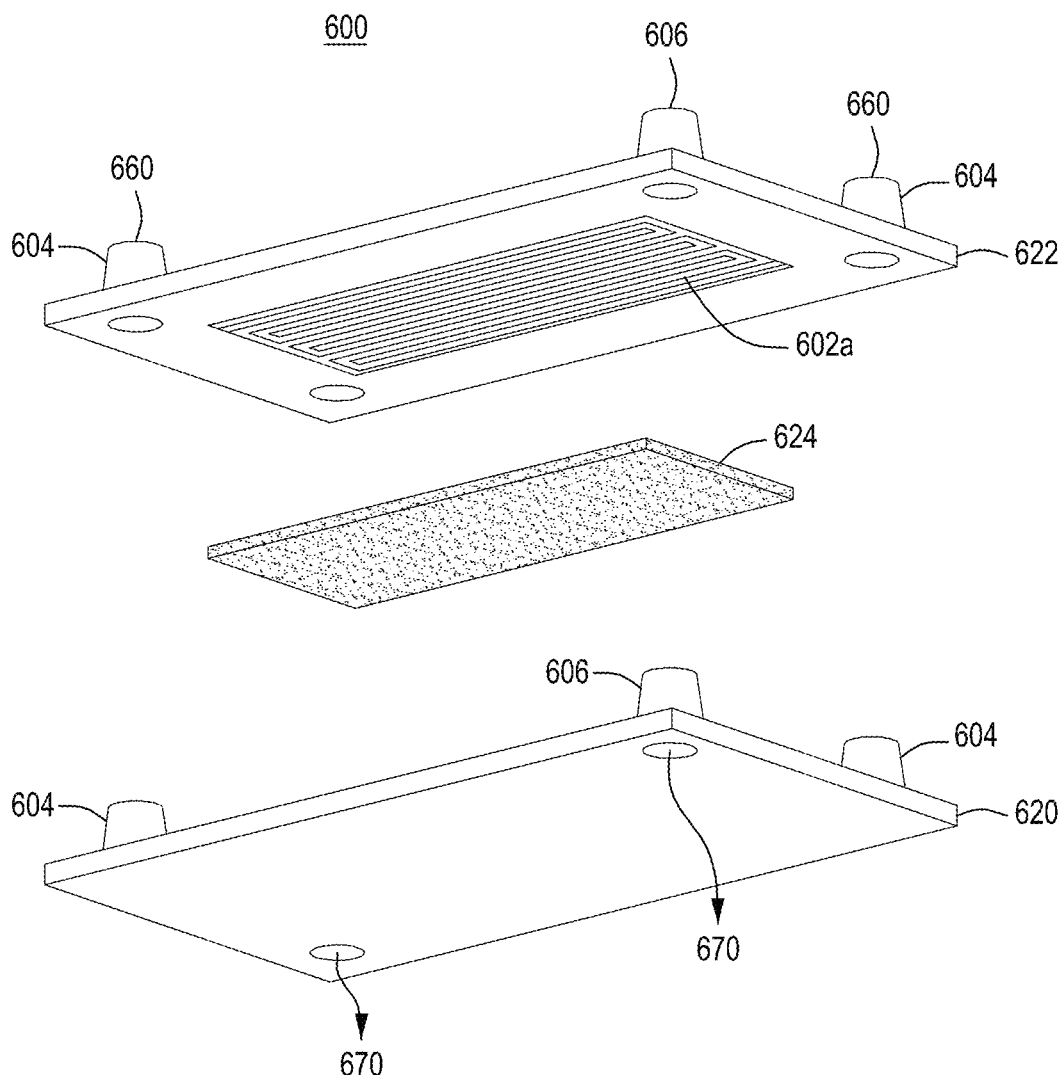
FIG. 6D depicts a bottom view of upper and lower members and a membrane of an exemplary TFF device.

FIG. 6D depicts a bottom view of upper and lower components of the exemplary TFF module shown in FIG. 6C. FIG. 6D depicts a bottom view of upper (622) and lower (620) components of an exemplary TFF module. Again portals 604 and 606 are seen. Note again that there is one retentate portal and one filtrate portal on each end of the device/module. The retentate and filtrate portals on the left side of the device/module will collect cells (flow path at 660) and medium (flow path at 670), respectively, for the same pass. Likewise, the retentate and filtrate portals on the right side of the device/module will collect cells (flow path at 660) and medium (flow path at 670), respectively, for the same pass. In FIG. 6D, the channel structure 602a can be seen on the upper member 622 of the TFF device 600. Thus, looking at FIGS. 6C and 6D, note that there is a channel structure 602 (602a and 602b) in both the upper and lower members, with a membrane 624 between the upper and lower portions of the channel structure. The channel structure 602 of the upper 622 and lower 620 members (602a and 602b, respectively) mate to create the flow channel with the membrane 624 positioned horizontally between the upper and lower members of the flow channel thereby bifurcating the flow channel.

Medium exchange (during cell growth) or buffer exchange (during cell concentration or rendering the cells competent) is performed on the TFF device/module by adding fresh medium to growing cells or a desired buffer to the cells concentrated to a desired volume; for example, after the cells have been concentrated at least 20-fold, 30-fold, 40-fold, 50-fold, 60-fold, 70-fold, 80-fold, 90-fold, 100-fold, 150-fold, 200-fold or more. A desired exchange medium or exchange buffer is added to the cells either by addition to the retentate reservoir or thorough the membrane from the filtrate side and the process of passing the cells through the TFF device 600 is repeated until the cells have been grown to a desired optical density or concentrated to a desired volume in the exchange medium or buffer. This process can be repeated any number of desired times so as to achieve a desired level of exchange of the buffer and a desired volume of cells. The exchange buffer may comprise, e.g., glycerol or sorbitol thereby rendering the cells competent for transformation in addition to decreasing the overall volume of the cell sample.

The TFF device 600 may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 6E:
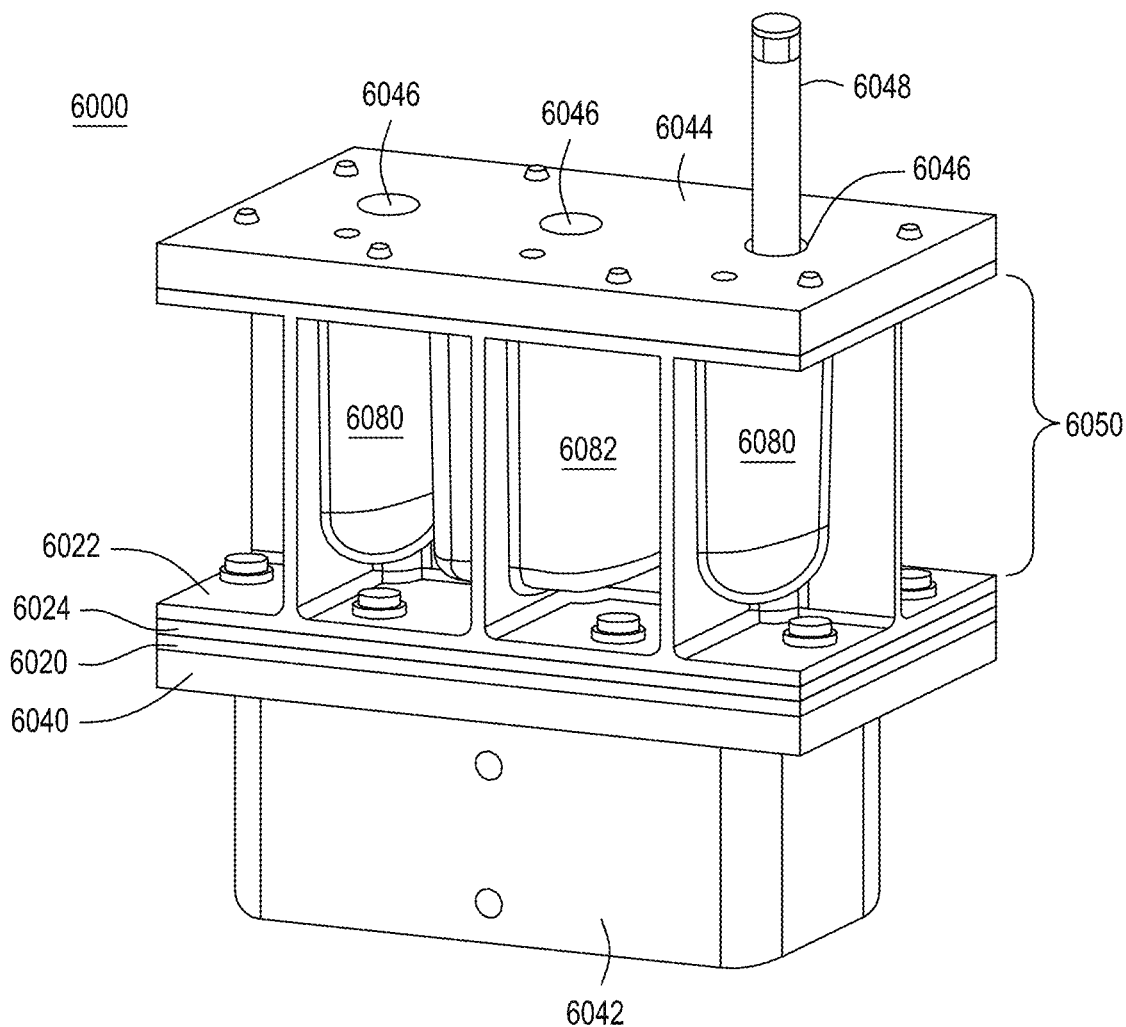
FIGS. 6E-6I depict various views of an embodiment of a TFF module comprising a TFF device and having fluidically coupled reservoirs for retentate, filtrate, and exchange buffer.

FIG. 6E depicts an exemplary configuration of an assembled TFF device, where, like the other configurations, the upper member and lower member in combination form a channel structure with a membrane disposed between the upper and lower members; however, in this configuration in addition to the retentate reservoirs, there is in addition an optional buffer or medium reservoir positioned between the retentate reservoirs, and a lower filtrate or permeate reservoir. In the TFF device 6000 configuration shown in FIG. 6E, 6044 is the top or cover of the TFF device 6000, having three ports 6046, where there is a pipette tip 6048 disposed in the right-most port 6046. The top 6044 of the TFF device 6000 is adjacent to and in operation is coupled with a combined reservoir and upper member structure 6050. Combined reservoir and upper member structure 6050 comprises a top surface that is adjacent the top or cover 6044 of the TFF device, a bottom surface which comprises the upper member 6022 of the TFF device, where the upper member 6022 of the TFF device defines the upper portion of the flow channel (not shown) disposed on the bottom surface of the upper member 6022 of the combined reservoir and upper member structure 6050. Additionally, combined reservoir and upper member structure 6050 comprises two retentate reservoirs 6080 and an optional buffer or medium reservoir 6082. The retentate reservoirs are fluidically coupled to the upper portion of the flow channel, and the buffer or medium reservoir is fluidically coupled to the retentate reservoirs. Also seen in this assembled view of TFF device 6000 is membrane 6024, lower member 6020 which, as described previously comprises on its top surface the lower portion of the tangential flow channel (not shown), where the channel structures of the upper member 6022 and lower member 6020 (neither shown in this view) mate to form a single flow channel. Beneath and adjacent to lower member 6020 is a gasket 6040, which is interposed between lower member 6020 and an optional filtrate (or permeate) reservoir 6042. The filtrate reservoir 6042 is in fluid connection with the lower portion of the flow channel, as a receptacle for the filtrate or permeate that is removed from the cell culture. In operation, top 6044, combined reservoir and upper member structure 6050, membrane 6024, lower member 6020, gasket 6040, and filtrate reservoir 6042 are coupled and secured together to be fluid- and air-tight. The assembled TFF device 1100 typically is from 4 to 25 cm in height, or from 5 to 20 cm in height, or from 7 to 15 cm in height; from 5 to 30 cm in length, or from 8 to 25 cm in length, or from 10 to 20 cm in length; and is from 3 to 15 cm in depth, or from 5 to 10 cm in depth. An exemplary TFF device is 11 cm in height, 12 cm in length, and 8 cm in depth. The retentate reservoirs, buffer or medium reservoir, and tangential flow channel-forming structures may be configured to be cooled to 4° C. for cell maintenance. The dimensions for the serpentine channel recited above, as well as the specifications and materials for the filter and the TFF device apply to the embodiment of the device shown in FIGS. 6E-6I. In embodiments including the present embodiment, up to 120 mL of cell culture can be grown and/or filtered, or up to 100 mL, 90 mL, 80 mL, 70 mL, 60 mL, 50 mL, 40 mL, 30 mL or 20 mL of cell culture can be grown and/or filtered.

Figure 6F:
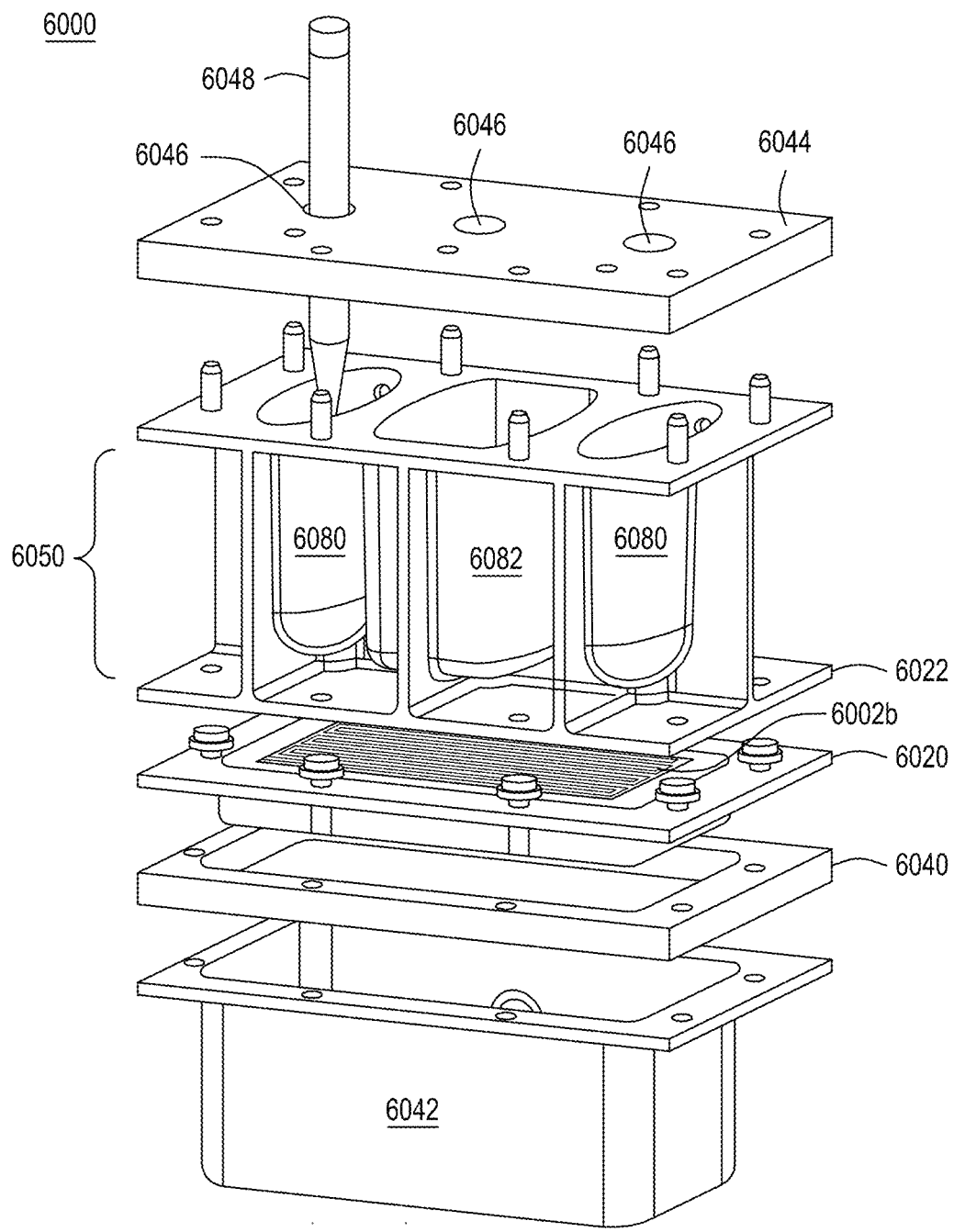

FIG. 6F depicts an exploded perspective view of TFF device 6000. In this configuration, 6044 is the top or cover of the TFF device 6000, having three ports 6046, where there is a pipette tip 6048 disposed in the left-most port 6046. The top 6044 of the TFF device 6000 is, in operation, coupled with a combined reservoir and upper member structure 6050. Combined reservoir and upper member structure 6050 comprises a top surface that, in operation, is adjacent the top or cover 6044 of the TFF device, a bottom surface which comprises the upper member 6022 of the TFF device, where the upper member 6022 of the TFF device defines the upper portion of the tangential flow channel (not shown). Combined reservoir and upper member structure 6050 comprises two retentate reservoirs 6080 and an optional buffer or medium reservoir 6082. The retentate reservoirs are fluidically coupled to the upper portion of the flow channel, and the optional buffer or medium reservoir is fluidically coupled to the retentate reservoirs. Also seen in this exploded view of TFF device 6000 is lower member 6020 which, as described previously comprises on its top surface the lower portion of the tangential flow channel 6002b (seen on the top surface of lower member 6020), where the upper and lower portions of the channel structures of the upper member 6022 and lower member 6020, respectively, when coupled mate to form a single flow channel (the membrane that is interposed between the upper member 6022 and lower member 6020 in operation is not shown). Beneath lower member 6020 is gasket 6040, which in operation is interposed between lower member 6020 and a filtrate (or permeate) reservoir 6042. In operation, top 6044, combined reservoir and upper member structure 6050, membrane (not shown), lower member 6020, gasket 6040, and filtrate reservoir 6042 are coupled and secured together to be fluid- and air-tight. In FIG. 6F, fasteners are shown that can be used to couple the various structures (top 6044, combined reservoir and upper member structure 6050, membrane (not shown), lower member 6020, gasket 6040, and filtrate reservoir 6042) together. However, as an alternative to screws or other like fasteners, the various structures of TFF device 6000 can be coupled using an adhesive, such as a pressure sensitive adhesive; ultrasonic welding; or solvent bonding. Further, a combination of fasteners, adhesives, and/or welding types may be employed to couple the various structures of the TFF device. One of ordinary skill in the art given the guidance of the present disclosure could find yet other configurations for coupling the components of TFF device 6000, such as e.g., clamps, mated fittings, and other such fasteners.

Figure 6G:
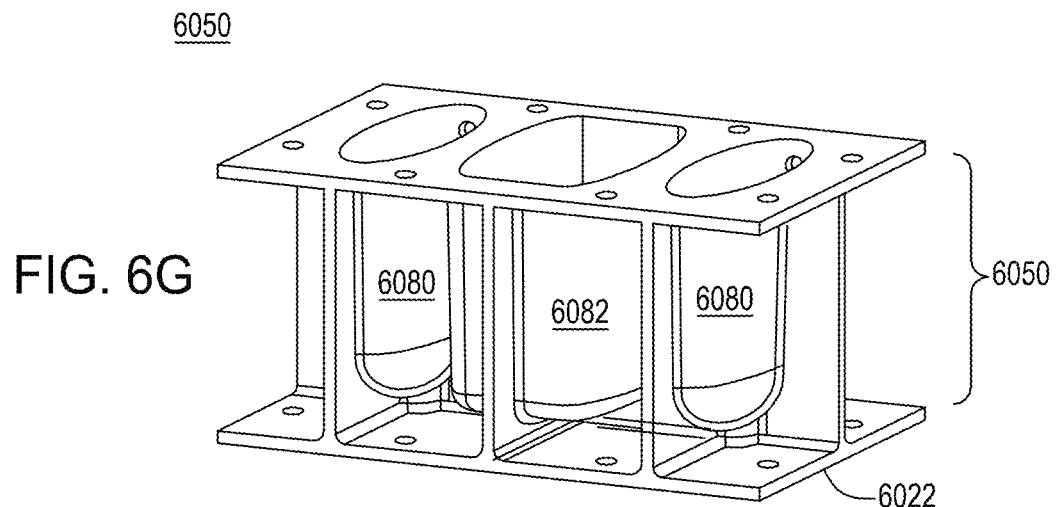
Figure 6H:
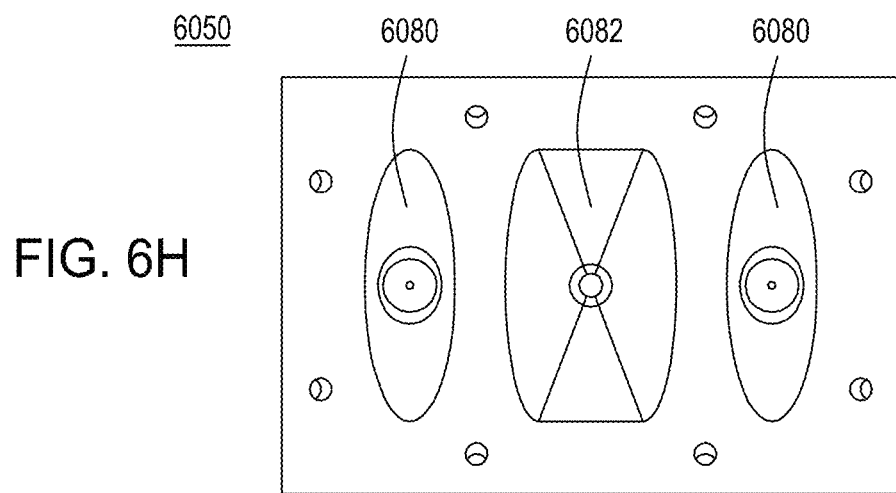
Figure 6I:
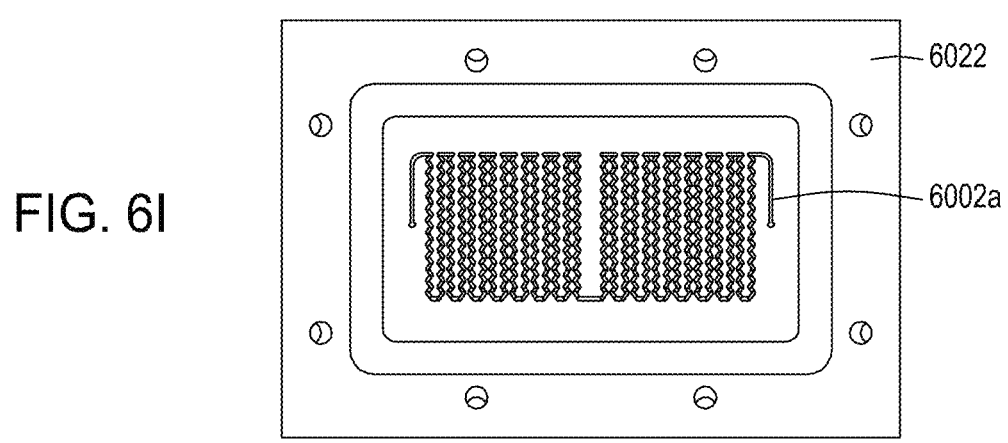

FIG. 6G depicts combined reservoir and upper member structure 6050, comprising two retentate reservoirs 6080 and an optional buffer or medium reservoir 6082, as well as upper member 6020, which is disposed on the bottom of combined reservoir and upper member structure 6050. Upper member 6022 of the TFF device defines the upper portion of the tangential flow channel (not shown) disposed on the bottom surface of the combined reservoir and upper member structure 6050. FIG. 6H is a top-down view of the upper surface of combined reservoir and upper member structure 6050, depicting the top of retentate reservoirs 6080 and buffer or medium reservoir 6082, as well as fluid or vacuum ports 6046. The retentate reservoirs are fluidically coupled to the upper portion of the flow channel, and the buffer or medium reservoir is fluidically coupled to the retentate reservoirs. FIG. 6I is a bottom-up view of the lower surface of combined reservoir and upper member structure 6050, showing the upper member 6020 with the upper portion of the tangential flow channel 6002a disposed on the bottom surface of upper member 6020. The flow channel 6002a disposed on the bottom surface of upper member 6020 in operation is mated to the bottom portion of the tangential flow channel disposed on the top surface of the lower member (not shown in this view, but see FIG. 6F), where the upper and lower portions of the flow channel structure mate to form a single flow channel.

As an alternative to the TFF module described above, a cell concentration module comprising a hollow filter may be employed. Examples of filters suitable for use in the present invention include membrane filters, ceramic filters and metal filters. The filter may be used in any shape; the filter may for example be cylindrical or essentially flat. Preferably, the filter used is a membrane filter, preferably a hollow fiber filter. The term "hollow fiber" is meant a tubular membrane. The internal diameter of the tube is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules comprising hollow fibers are commercially available from various companies, including G.E. Life Sciences (Marlborough, Mass.) and InnovaPrep (Drexel, Mo.). Specific examples of hollow fiber filter systems that can be used, modified or adapted for use in the present methods and systems include, but are not limited to, U.S. Pat. Nos. 9,738,918; 9,593,359; 9,574,977; 9,534,989;

9,446,354; 9,295,824; 8,956,880; 8,758,623; 8,726,744; 8,677,839; 8,677,840; 8,584,536; 8,584,535; and 8,110,112.

Nucleic Acid Assembly Module

Certain embodiments of the automated multi-module cell editing instruments of the present disclosure optionally include a nucleic acid assembly module. The nucleic acid assembly module is configured to accept and assemble the nucleic acids necessary to facilitate the desired genome editing events. In general, the term "vector" refers to a nucleic acid molecule capable of transporting a desired nucleic acid to which it has been linked into a cell. Vectors include, but are not limited to, nucleic acid molecules that are single-stranded, double-stranded, or partially double-stranded; nucleic acid molecules that include one or more free ends, no free ends (e.g., circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors" or "editing vectors." Common expression vectors of utility in recombinant DNA techniques are often in the form of plasmids. Additional vectors include fosmids, phagemids, and synthetic chromosomes.

Recombinant expression vectors can include a nucleic acid in a form suitable for transcription, and for some nucleic acid sequences, translation and expression of the nucleic acid in a host cell, which means that the recombinant expression vectors include one or more regulatory elements—which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g. in an in vitro transcription/translation system or in a host cell when the vector is introduced into the host cell). Appropriate recombination and cloning methods are disclosed in US Pub. No. 2004/0171156, the contents of which are herein incorporated by reference in their entirety for all purposes.

In some embodiments, a regulatory element is operably linked to one or more elements of a targetable nuclease system so as to drive transcription, and for some nucleic acid sequences, translation and expression of the one or more components of the targetable nuclease system.

In addition, the polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably liked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated multi-module cell editing instruments include, but are not limited to, those assembly methods that use restriction endonucleases, including PCR, BioBrick assembly (U.S. Pat. No. 9,361,427), Type IIS cloning (e.g., GoldenGate assembly, European Patent Application Publication EP 2 395 087 A1), and Ligase Cycling Reaction (de Kok, ACS Synth Biol., 3(2): 97-106 (2014); Engler, et al., PLoS One, 3(11):e3647 (2008); and U.S. Pat. No. 6,143,527). In other embodiments, the nucleic acid assembly techniques performed by the disclosed automated multi-module cell editing instruments are based on overlaps between adjacent parts of the nucleic acids, such as Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244-51 (2009)); U.S. Pat. Nos. 5,888,732; and 6,277,608), and topoisomerase-mediated cloning (Udo, PLoS One, 10(9): e0139349 (2015); and U.S. Pat. No. 6,916,632). These and other nucleic acid assembly techniques are described, e.g., in Sands and Brent, Curr Protoc Mol Biol., 113:3.26.1-3.26.20 (2016).

The nucleic acid assembly module is temperature controlled depending upon the type of nucleic acid assembly used in the automated multi-module cell editing instrument. For example, when PCR is utilized in the nucleic acid assembly module, the module includes a thermocycling capability allowing the temperatures to cycle between denaturation, annealing and extension steps. When single temperature assembly methods (e.g., isothermal assembly methods) are utilized in the nucleic acid assembly module, the module provides the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated multi-module cell editing instrument.

In one embodiment, the nucleic acid assembly module is a module to perform assembly using a single, isothermal reaction. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes—an exonuclease, a polymerase, and a ligase-along with buffer components. Because the process is isothermal and can be performed in a 1-step or 2-step method using a single reaction vessel, isothermal assembly reactions are ideal for use in an automated multi-module cell editing instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

The Cell Transformation Module

Figure 7A:
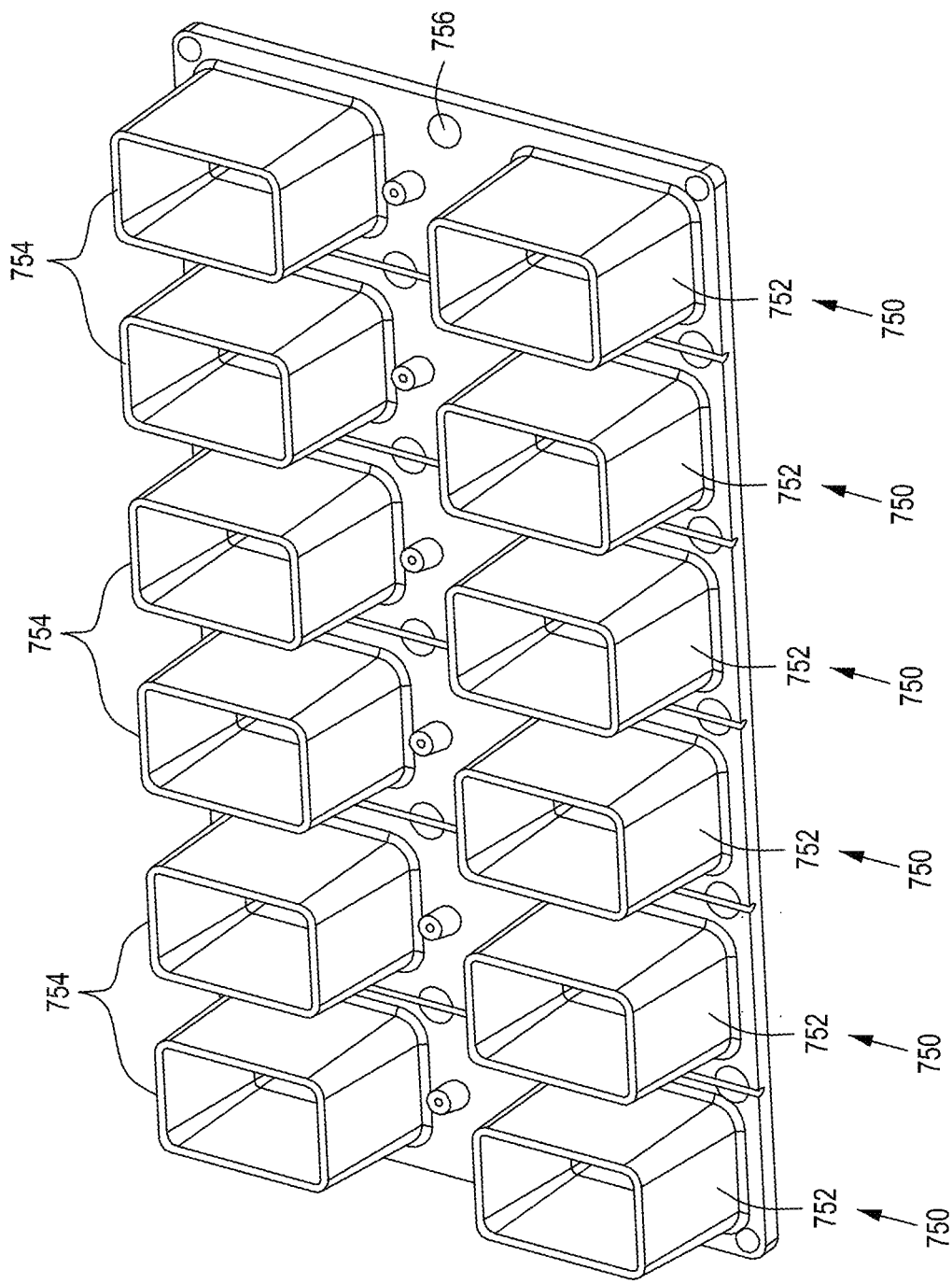
FIGS. 7A and 7B are top perspective and bottom perspective views, respectively, of flow-through electroporation devices (here, there are six such devices co-joined).
Figure 7B:
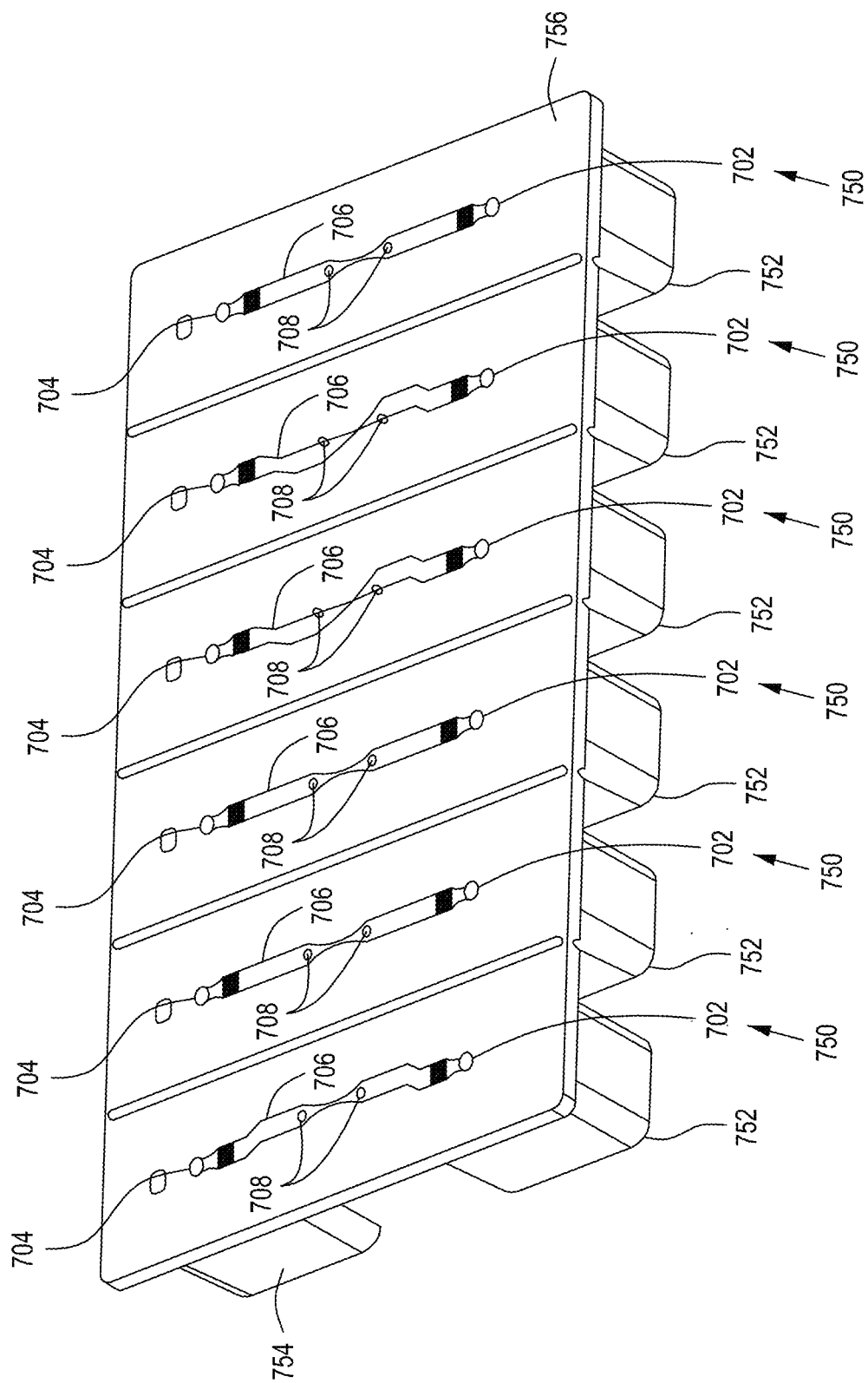

In addition to the modules for cell growth, cell concentration, and nucleic acid assembly, FIGS. 7A-7E depict variations on one embodiment of a cell transformation module (in this case, a flow through electroporation device) that may be included in a cell growth/concentration/transformation instrument. FIGS. 7A and 7B are top perspective and bottom perspective views, respectively, of six co-joined flow-through electroporation devices 750. FIG. 7A depicts six flow-through electroporation units 750 arranged on a single substrate 756. Each of the six flow-through electroporation units 750 have wells 752 that define cell sample inlets and wells 754 that define cell sample outlets. FIG. 7B is a bottom perspective view of the six co-joined flow-through electroporation devices of FIG. 7A also depicting six flow-through electroporation units 750 arranged on a single substrate 4156. Six inlet wells 4152 can be seen, one for each flow-through electroporation unit 750, and one outlet well 754 can be seen (the outlet well of the left-most flow-through electroporation unit 750). Additionally seen in FIG. 7B are an inlet 702, outlet 704, flow channel 706 and two electrodes 708 on either side of a constriction in flow channel 706 in each flow-through electroporation unit 750. Once the six flow-through electroporation units 750 are fabricated, they can be separated from one another (e.g., "snapped apart") and used one at a time, or alternatively in embodiments two or more flow-through electroporation units 750 can be used in parallel without separation.

The flow-through electroporation devices achieve high efficiency cell electroporation with low toxicity. The flow-through electroporation devices of the disclosure allow for particularly easy integration with robotic liquid handling instrumentation that is typically used in automated systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Generally speaking, microfluidic electroporation—using cell suspension volumes of less than approximately 10 ml and as low as 1 μl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit electroporation device configurations; and integrated, automatic, multi-module cell processing and analysis.

In specific embodiments of the flow-through electroporation devices of the disclosure the toxicity level of the transformation results in greater than 10% viable cells after electroporation, preferably greater than 15%, 20%, 25%, 30%, 35%, 40%, 45%, 50%, 55%, 60%, 70%, 75%, 80%, 85%, 90%, or even 95% viable cells following transformation, depending on the cell type and the nucleic acids being introduced into the cells.

The flow-through electroporation device described in relation to FIGS. 7A-7E comprises a housing with an electroporation chamber, a first electrode and a second electrode configured to engage with an electric pulse generator, by which electrical contacts engage with the electrodes of the electroporation device. In certain embodiments, the electroporation devices are autoclavable and/or disposable, and may be packaged with reagents in a reagent cartridge. The electroporation device may be configured to electroporate cell sample volumes between 1 μl to 2 ml, 10 μl to 1 ml, 25 μl to 750 μl, or 50 μl to 500 μl. The cells that may be electroporated with the disclosed electroporation devices include mammalian cells (including human cells), plant cells, yeasts, other eukaryotic cells, bacteria, archaea, and other cell types.

Figure 7C:
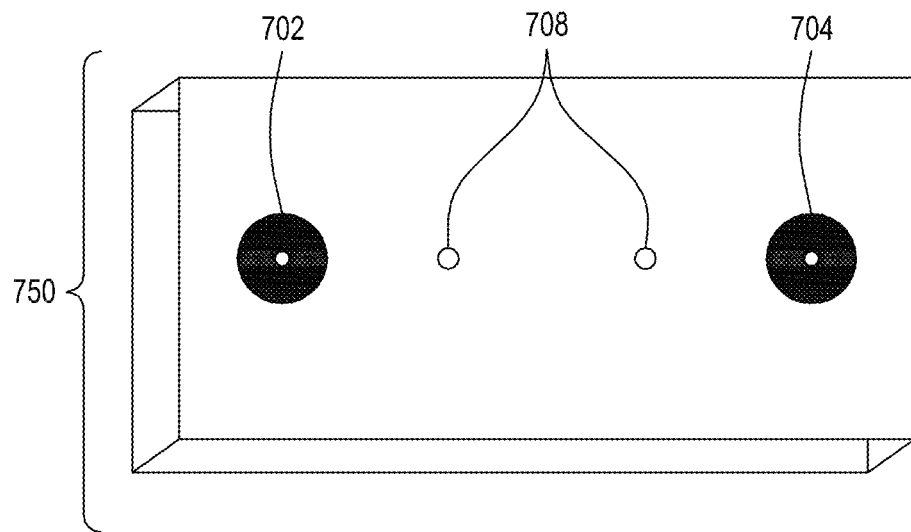
FIG. 7C is a top view of one embodiment of an exemplary flow-through electroporation device.
Figure 7D:
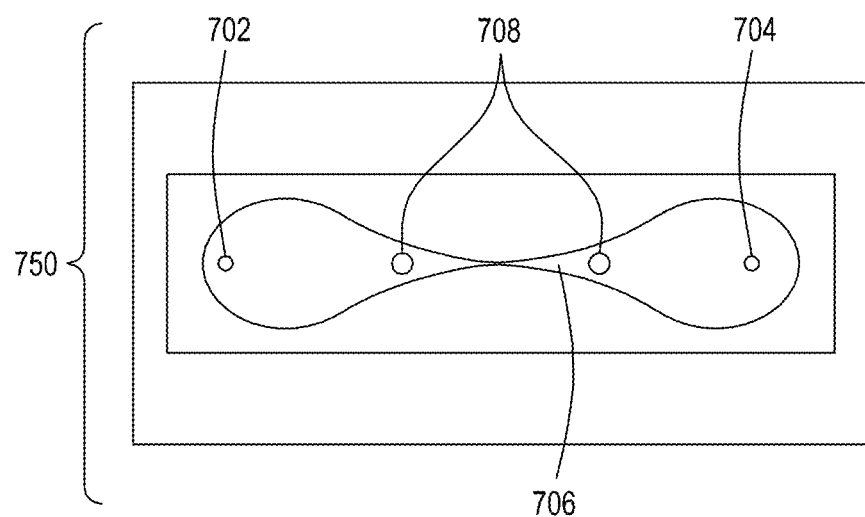
FIG. 7D depicts a top view of a cross section of the electroporation device of FIG. 7C.
Figure 7E:
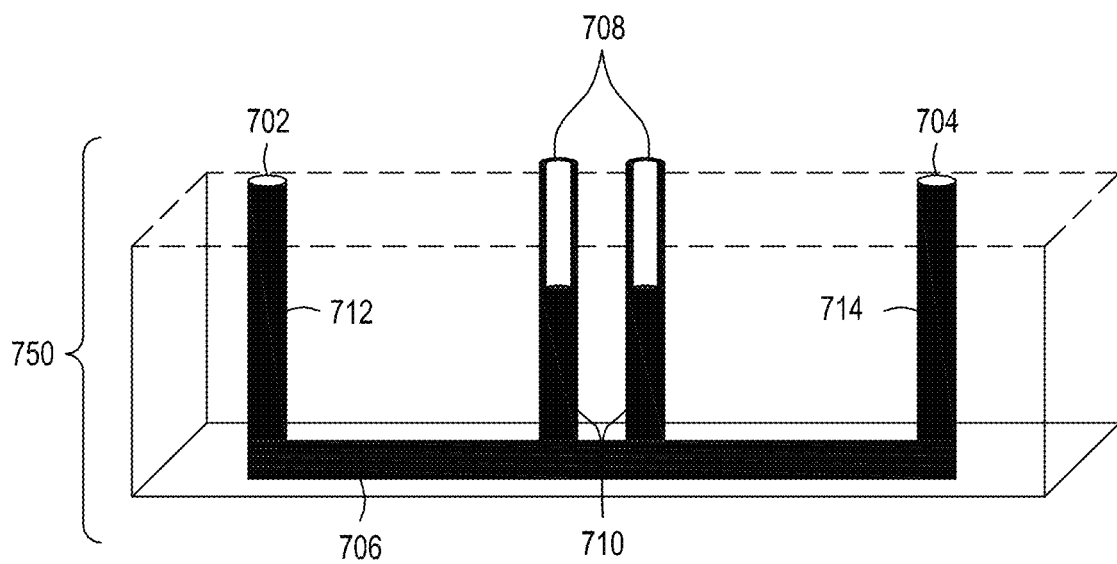
FIG. 7E is a side view cross section of a lower portion of the electroporation devices of FIGS. 7C and 7D.

In one exemplary embodiment, FIG. 7C depicts a top view of a flow-through electroporation device 750 having an inlet 702 for introduction of cells and an exogenous reagent to be electroporated into the cells ("cell sample") and an outlet 704 for the cell sample following electroporation. Electrodes 708 are introduced through electrode channels (not shown) in the device. FIG. 7D shows a cutaway view from the top of flow-through electroporation device 750, with the inlet 702, outlet 704, and electrodes 708 positioned with respect to a constriction in flow channel 706. A side cutaway view of the bottom portion of flow-through electroporation device 750 in FIG. 7E illustrates that electrodes 708 in this embodiment are positioned in electrode channels 710 and perpendicular to flow channel 706 such that the cell sample flows from the inlet channel 712 through the flow channel 706 to the outlet channel 714, and in the process the cell sample flows into the electrode channels 710 to be in contact with electrodes 708. In this aspect, the inlet channel, outlet channel and electrode channels all originate from the top planar side of the device; however, the flow-through electroporation architecture depicted in FIGS. 7C-7E is but one architecture useful with the reagent cartridges described herein. Additional electrode architectures are described, e.g., in U.S. Ser. No. 16/147,120, filed 24 Sep. 2018; Ser. No. 16/147,865, filed 30 Sep. 2018; and Ser. No. 16/147,871, filed 30 Sep. 2018.

The Cell Enrichment Module

One optional aspect provides automated modules and instruments for nucleic acid-guided nuclease genome editing that implement enrichment techniques for cells whose genomes have been properly edited. The enrichment modules perform methods that use cell singulation and normalization to reduce growth competition between edited and unedited cells. Singulation overcomes growth bias from unedited cells or cells containing edits conferring growth advantages or disadvantages. The methods, modules and instruments may be applied to all cell types including, archaeal, prokaryotic, and eukaryotic (e.g., yeast, fungal, plant and animal) cells.

Singulating, optional induction of editing, and normalization of cell colonies leads to 2-250×, 10-225×, 25-200×, 40-175×, 50-150×, 60-100×, or 5-100× gains in identifying edited cells over prior art methods and provides new approaches for generating arrayed or pooled edited cells comprising genome libraries. Additionally, the methods, modules, and instruments may be leveraged to create iterative editing systems to generate combinatorial libraries, identify rare cell edits, and enable high-throughput enrichment applications to identify editing activity.

Figure 8A:
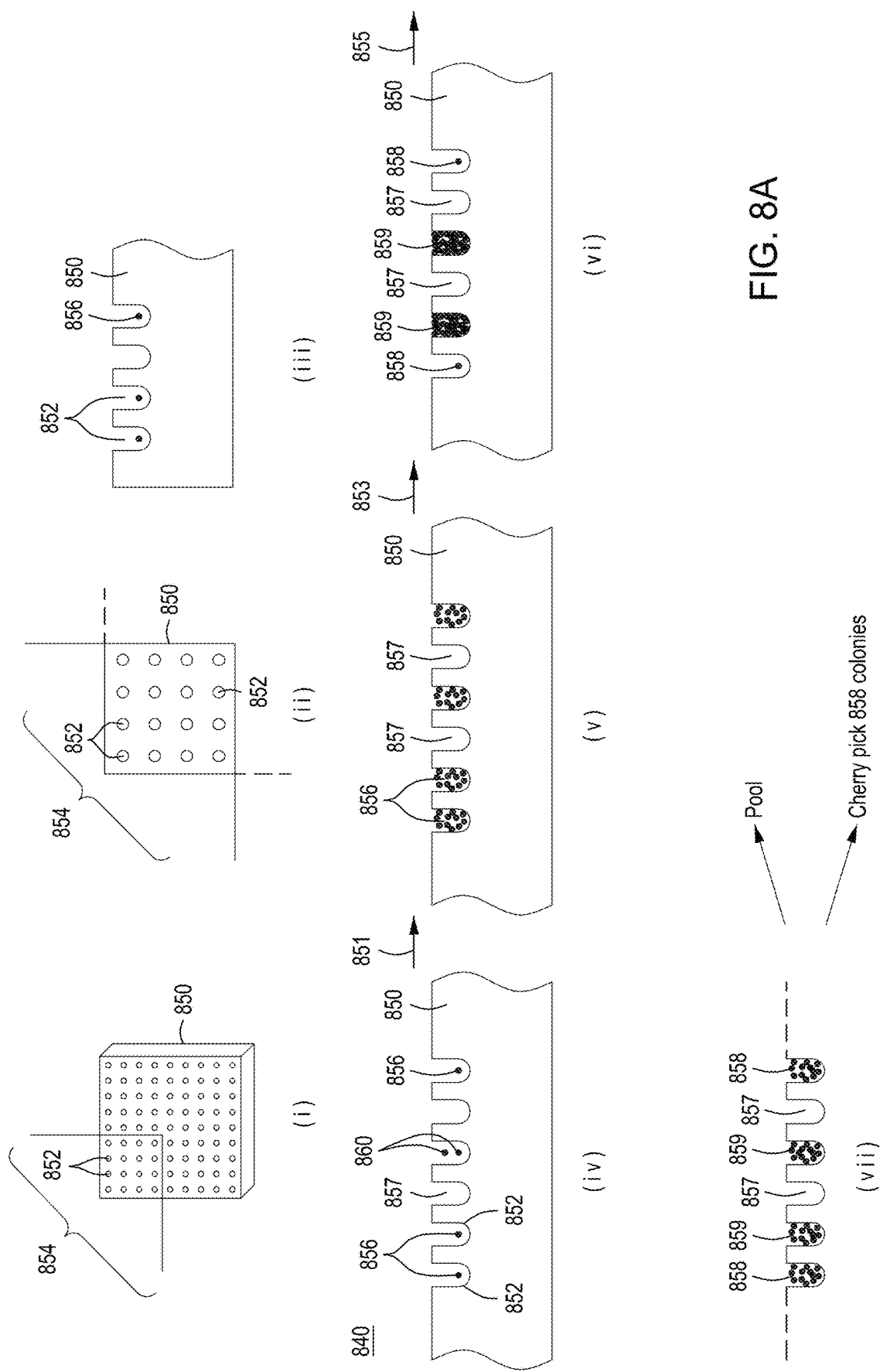
FIG. 8A depicts a simplified graphic of a workflow for singulating, editing and normalizing cells after nucleic acid-guided nuclease genome editing in a solid wall device.

The compositions and methods described herein improve nucleic acid-guided nuclease editing systems in which nucleic acid-guided nucleases (e.g., RNA-guided nucleases) are used to edit specific target regions in an organism's genome. FIG. 8A depicts a solid wall device 850 and a workflow for singulating cells in microwells in the solid wall device, where in this workflow one or both of the gRNA and nuclease are under the control of an inducible promoter. At the top left of the figure (i), there is depicted solid wall device 850 with microwells 852. A section 854 of substrate 850 is shown at (ii), also depicting microwells 852. At (iii), a side cross-section of solid wall device 850 is shown, and microwells 852 have been loaded, where, in this embodiment, Poisson loading has taken place; that is, each microwell has one or no cells, and the likelihood that any one microwell has more than one cell is low. At (iv), workflow 840 is illustrated where substrate 850 having microwells 852 shows microwells 856 with one cell per microwell, microwells 857 with no cells in the microwells, and one microwell 260 with two cells in the microwell. In step 851, and the cells in the microwells are allowed to double approximately 2-50 times to form clonal colonies (v), then editing is induced 853 by heating the substrate (e.g., for temperature-induced editing) or flowing chemicals under or over the substrate (e.g., sugars, antibiotics for chemical-induced editing) or by moving the solid wall device to a different medium; particularly facile if the solid wall device is placed on a fluid permeable membrane which forms the bottom of microwells 852. After induction of editing 853, many cells in the colonies of cells that have been edited die as a result of the double-strand cuts caused by active editing, and there is possibly a lag in growth for the edited cells that do survive but must repair and recover following editing (microwells 858), where cells that do not undergo editing thrive (microwells 859) (vi). All cells are allowed to grow to continue to establish colonies and normalize, where the colonies of edited cells in microwells 858 catch up in size and/or cell number with the cells in microwells 859 that do not undergo editing (vii) due to cell senescence as the unedited cells reach stationary phase. Once the cell colonies are normalized, either pooling of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 858) are identified and selected (e.g., "cherry picked") resulting in even greater enrichment of edited cells.

In growing the cells, the medium used will depend, of course, on the type of cells being edited—e.g., bacterial, yeast or mammalian. For example, medium for bacterial growth includes LB, SOC, M9 Minimal medium, and Magic medium; medium for yeast cell growth includes TPD, YPG, YPAD, and synthetic minimal medium; and medium for mammalian cell growth includes MEM, DMEM, IMDM, RPMI, and Hanks.

Figure 8B:
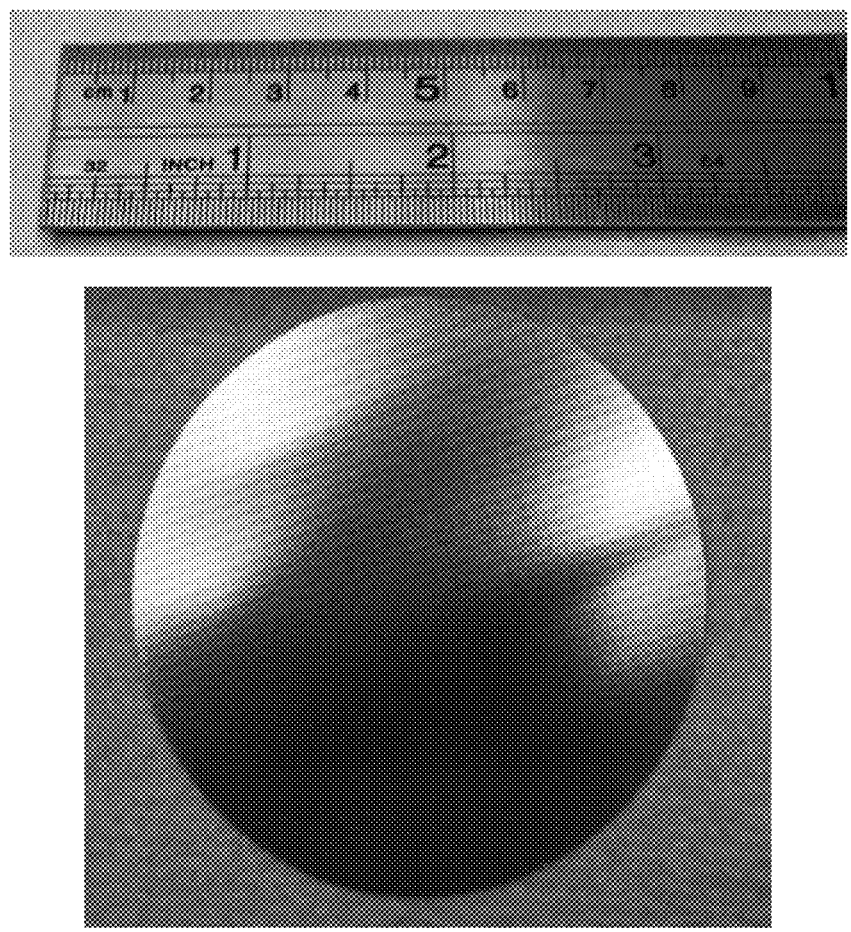
FIG. 8B is a photograph of one embodiment of a solid wall device.

FIG. 8B is a photograph of one embodiment of a solid wall device comprising microwells for singulating cells. As can be seen from the photo, the solid wall device is approximately 2 inches (~47 mm) in diameter. The solid device seen in this photograph is essentially a perforated disk of 816 stainless steel, where the perforations form the walls of the microwells, and a filter or membrane is used to form the bottom of the microwells. Use of a filter or membrane (such as a 0.22μ PVDF Duropore™ woven membrane filter) allows for medium and/or nutrients to enter the microwells but prevents the cells from flowing down and out of the microwells. Filter or membrane members that may be used in the solid wall singulation/growth/editing/normalization devices and modules are those that are solvent resistant, are contamination free during filtration, and are able to retain the types and sizes of cells of interest. For example, in order to retain small cell types such as bacterial cells, pore sizes can be as low as 0.2 μm, however for other cell types, the pore sizes can be as high as 0.5 μm. Indeed, the pore sizes useful in the cell concentration device/module include filters with sizes from 0.20 μm, 0.21 μm, 0.22 μm, 0.23 μm, 0.24 μm, 0.25 μm, 0.26 μm, 0.27 μm, 0.28 μm, 0.29 μm, 0.30 μm, 0.31 μm, 0.32 μm, 0.33 μm, 0.34 μm, 0.35 μm, 0.36 μm, 0.37 μm, 0.38 μm, 0.39 μm, 0.40 μm, 0.41 μm, 0.42 μm, 0.43 μm, 0.44 μm, 0.45 μm, 0.46 μm, 0.47 μm, 0.48 μm, 0.49 μm, 0.50 μm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

In the photograph shown in FIG. 8B, the perforations are approximately 152 nM in diameter, resulting in the microwells having a volume of approximately 2.5 nL, with a total of approximately 30,000 wells. The distance between the microwells is approximately 279 nM center-to-center. Though here the microwells have a volume of approximately 2.5 nL, the volume of the microwells may be from 1 to 25 nL, or preferably from 2 to 10 nL, and even more preferably from 2 to 4 nL. The preferred size/volume of the microwells will depend of cell type (e.g., bacterial, yeast, mammalian). The perforated disk shown here is made of 316 stainless steel; however other bio-compatible metals and materials may be used. The solid wall device may be disposable or it may be reusable. The solid wall device shown in FIG. 8B is round, but can be of any shape, for example, square, rectangular, oval, etc. Round solid wall devices are useful if petri dishes are used to supply the solid wall device with nutrients via solid medium. The filters used to form the bottom of the wells of the solid wall device include 0.22μ PVDF Duropore™ woven membrane filters. Further, though a 2-inch (~47 mm) diameter solid wall device is shown, the solid wall devices may be smaller or larger as desired and the configuration of the solid wall device will depend on how nutrients are supplied to the solid wall device, and how media exchange is performed. Although a round solid wall device is described here, the solid wall devices can be of any shape and size, including rectangular solid wall devices with 100K, 200K or more wells, in addition to configurations of solid wall devices and cassettes that are multiplexed, e.g., stacked.

Figure 8C:
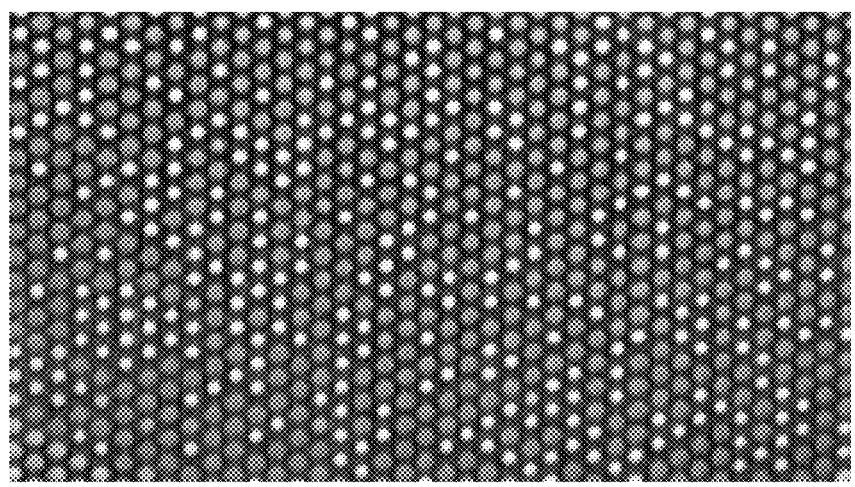
FIGS. 8C-8E are photographs of E. coli cells singulated (via Poisson distribution) and grown into colonies in microwells in a solid wall device with a permeable bottom at low, medium, and high magnification, respectively.
Figure 8D:
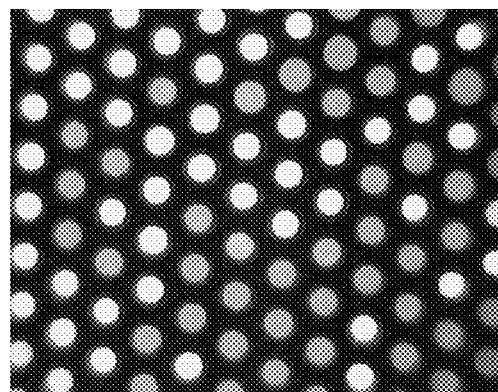
Figure 8E:
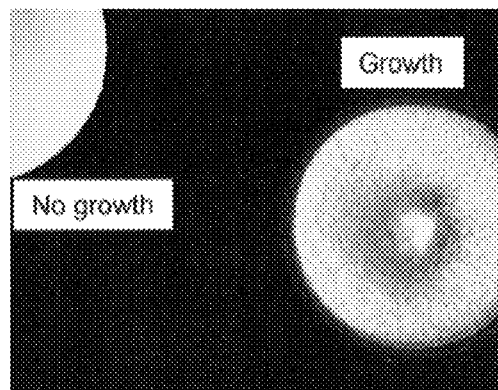
Figure 8E:
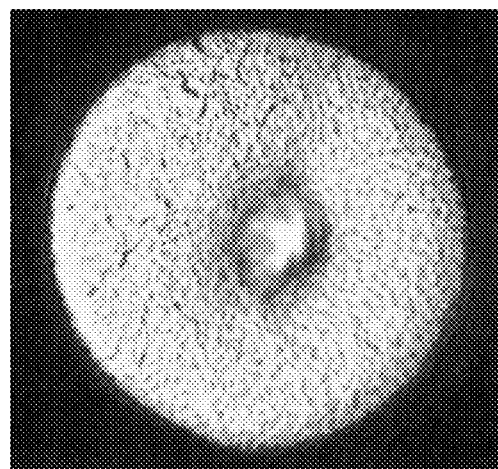

FIGS. 8C-8E are photographs of *E. coli* cells at low, medium and high magnification, respectively, singulated via Poisson distribution in microwells in a solid wall device with a membrane bottom. FIG. 8C shows digital growth at low magnification where the darker microwells are microwells where cells are growing. FIG. 8D is a top view of microwells in a solid wall device where the darker microwells are microwells where cells are growing. FIG. 8E is a photograph of microwells where the membrane (e.g., the permeable membrane that forms the bottom of the microwells) has been removed, where unpatterned (smooth) microwells are microwells where cells are not growing, and microwells with irregular pigment/patterned are microwells where cells are growing, and, in this photograph, have filled the microwells in which they are growing. In these photographs, a 0.2 μm filter (membrane) was pressed against the perforated metal sold wall device such as the round solid wall device depicted in FIG. 8B. The perforated metal solid wall device formed the walls of the microwells, and the 0.2 μm filter formed the bottom of the microwells. To load the solid wall device, the *E. coli* cells were pulled into the microwells using a vacuum. The solid wall device+filter was then placed on an LB agar plate membrane-side down, and the cells were grown overnight at 30° C., then two days at room temperature. The membrane was removed and the bottomless microwells were photographed by light microscopy. Note the ease with which different selective media can be used to select for certain cell phenotypes; that is, one need only transfer the solid wall device+filter to a different plate or petri dish comprising a desired selective medium or flow a desired selective medium into a substrate onto which the solid wall device and coupled membrane are positioned.

In addition to the solid wall cell singulation device described in relation to FIGS. 8A-8E, other cell singulation devices may be employed in the multi-module cell processing instrument, such as those described in U.S. Ser. No. 62/735,365, entitled "Detection of Nuclease Edited Sequences in Automated Modules and Systems", filed 24 Sep. 2018, and U.S. Ser. No. 62/781,112, entitled "Improved Detection of Nuclease Edited Sequences in Automated Modules and Systems", filed 18 Dec. 2018, including singulation by plating on agar, singulation by isolating cells on functionalized islands, singulation within aqueous droplets carried in a hydrophobic carrier fluid, or singulation within a polymerized alginate scaffold (for this embodiment of singulation, also see U.S. Ser. No. 62/769,805, entitled "Improved Detection of Nuclease Edited Sequences in Automated Modules and Instruments via Bulk Cell Culture", filed 20 Nov. 2018.

Figure 8F:
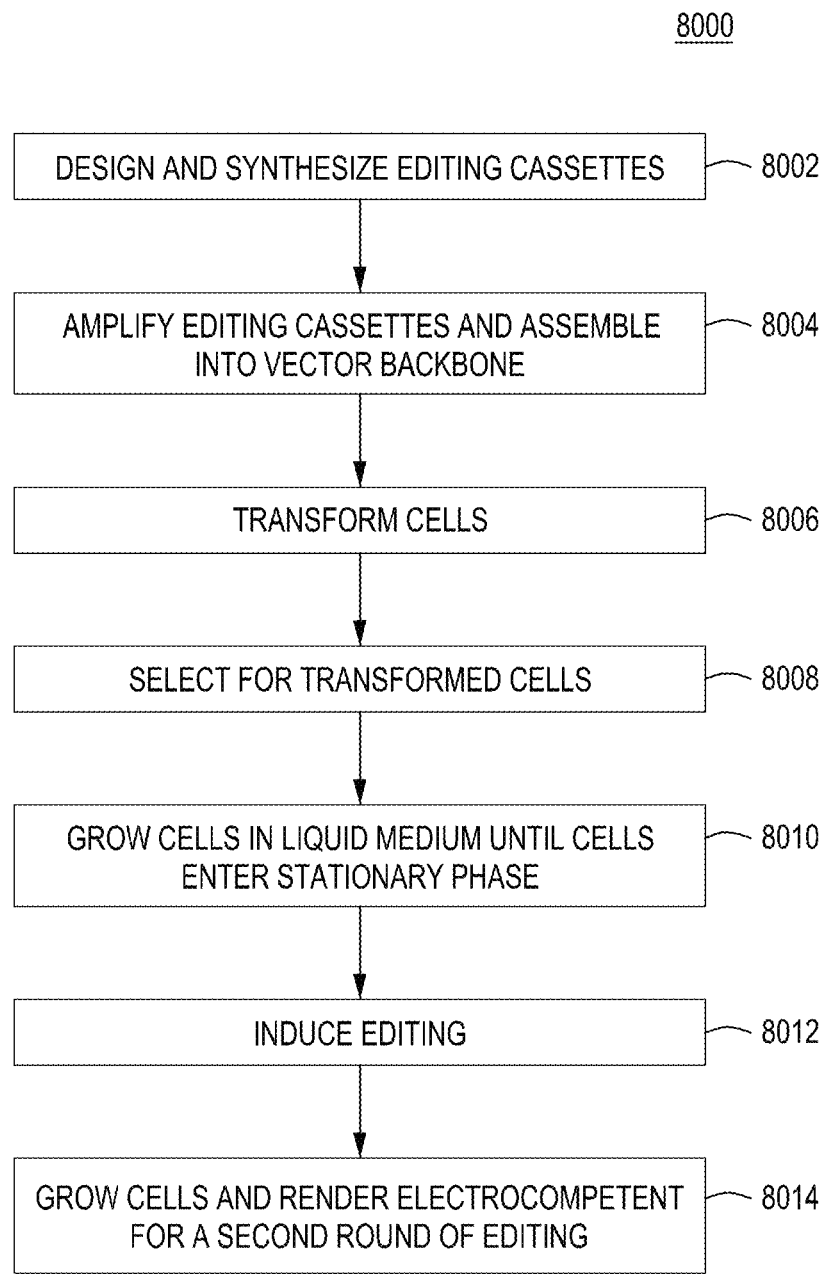
FIG. 8F is a simplified block diagram of methods for enriching for live cells that have been edited via nucleic acid-guided nuclease editing that do not involve singulation or a singulation device and instead utilize cell growth in liquid and induction of editing.

As an alternative to singulation, inducing editing via an inducible promoter driving one or both of the gRNA and the nuclease at a specific time in the cell growth cycle may be employed. FIG. 8F shows a simplified flow chart for exemplary methods 8000 for enriching for edited cells. Looking at FIG. 8F, method 8000 begins by designing and synthesizing editing cassettes 8002. As described in relation to nucleic acid-guided editing above, each editing cassette typically comprises a gRNA, a donor DNA, and a PAM or spacer mutation. Once the individual editing cassettes have been synthesized, the individual editing cassettes may be "linked" or "assembled" together and are amplified and assembled into editing vector backbones 8004. The editing vectors comprising the editing cassettes are then used to transform cells 8006 thereby creating a library of transformed cells. In addition to the vectors comprising the assembled editing cassettes, the cells may be transformed simultaneously with a separate engine vector comprising a coding sequence for a nuclease. Alternatively, the cells may already be expressing the nuclease (e.g., the cells may have already been transformed with an engine vector or the coding sequence for the nuclease may be stably integrated into the cellular genome) such that only the editing vector needs to be transformed into the cells; or the cells may be transformed with a single vector comprising all components required to perform nucleic acid-guided nuclease genome editing (e.g., all of the nuclease and an editing cassette), which is advantageous when employing curing and recursive rounds of editing.

A variety of delivery systems may be used to introduce (e.g., transform or transfect) nucleic acid-guided nuclease editing system components into a host cell 8008. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018. If the screening/selection module is one module in an automated multi-module cell editing system, the cells are likely transformed in an automated cell transformation module.

Once transformed 8006, the cells can then be subjected to selection using a selectable marker 8008. Selectable markers are employed to select for cells that have received both the engine and editing vectors, or for cells that have been transformed with a single, combined engine and editing vector. Commonly used selectable markers include drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418.

Once cells that have been properly transformed are selected 8008, the next step in method 8000 is to grow cells in liquid medium until the cells enter (or are close to entering) the stationary phase of growth. Once the cells are in stationary phase 8010 (or nearly so), editing is induced 8012 in the cells by induction of transcription of one or both of the nuclease and gRNA. Once editing is induced 8012, the cells can be grown, rendered electrocompetent, and subjected to another round of editing 8014.

Figure 8G:
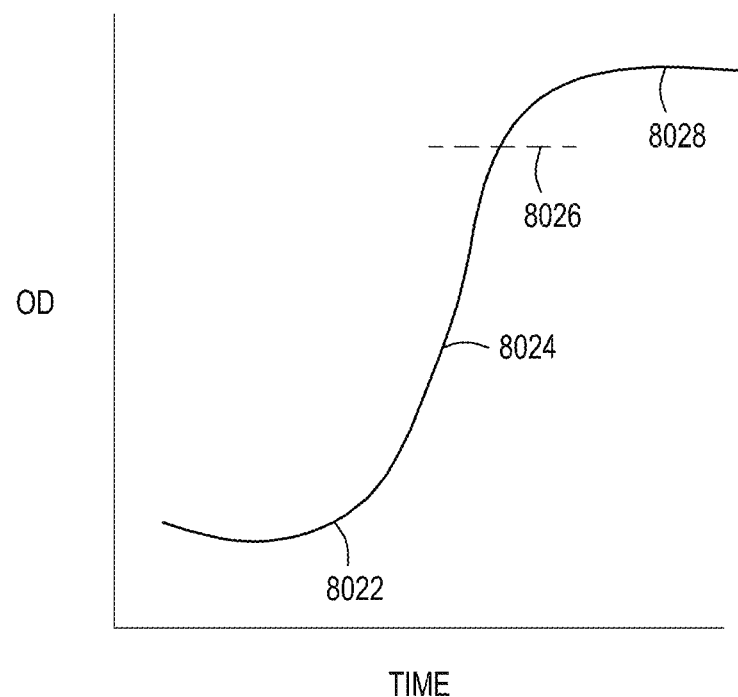
FIG. 8G depicts a typical growth curve for cells in culture.

FIG. 8G depicts a typical growth curve 8020 for cells in culture (optical density versus time). Initially there is a lag phase 8022, then the cells enter log phase 8024 where they grow quickly, and finally the cells reach stationary phase 8028 where the cells are no longer dividing. The present methods employ inducing transcription of either or both the nuclease and/or gRNA at timepoint 8026 or later when the cells are in the stationary phase of growth or nearly so; that is, the cells are induced at a timepoint at least 60% into the log phase of growth, or at least 65% into the log phase of growth, or at least 70% into the log phase of growth, or at least 71, 72, 73, 74, 75, 76, 77, 78, 79, 80, 81, 82, 83, 84, 85, 86, 87, 88, 89, 90, 91, 92, 93, 94, 95, 96, 79, 98, or 99% into the log phase of growth, and at any time during the stationary phase of growth.

Figure 8H:
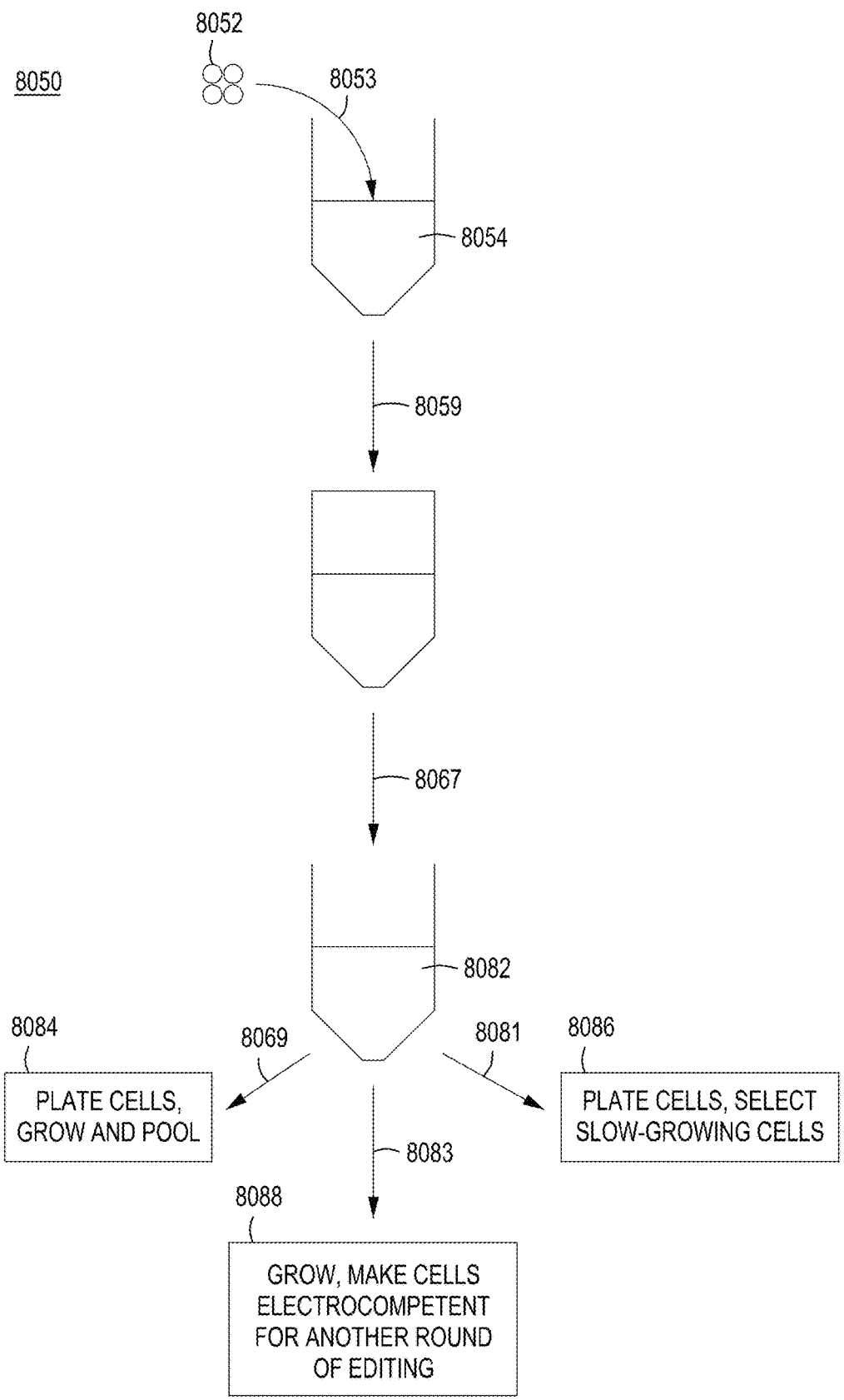
FIG. 8H is a graphic depiction of methods for growing, inducing, editing, enriching, and screening for edited cells in a population of cells.

FIG. 8H depicts an exemplary protocol 8050 for performing nucleic acid-guided nuclease genome editing. FIG. 8H depicts the protocols shown in FIG. 8F for editing cells. First, a library or collection of editing vectors 8052 (editing vectors each comprising an editing cassette) is introduced 8053 (e.g., electroporated) into cultured cells 8054 that comprise a coding sequence for a nuclease under the control of a constitutive or inducible promoter (preferably an inducible promoter), contained 1) on an "engine plasmid" (most often along with a selectable marker) that has already been transformed into the cells; 2) integrated into the genome of the cells being transformed; or 3) the coding sequence for the nuclease may be located on the editing vector. The editing vectors 8052 comprise a donor DNA, a PAM or spacer-altering sequence (most often a sequence that disables the PAM at the target site in the genome), a coding sequence for a gRNA under the control of an inducible promoter, and a selectable marker.

At step 8059, cells are grown until they reach stationary phase, or nearly so. Once the cells reach the stationary phase, editing is induced 8067 (e.g., where transcription of the nuclease, gRNA or both is induced) and the cells in the culture 8082 are edited and then allowed to recover from editing. Once recovered, the cells can be plated 8069, grown and pooled 8084. Alternatively, the cells from culture 8082 can be plated 8081, and slow-growing colonies are selected 8086 thereby cherry picking edited colonies. In yet another alternative, the cells can be retained in liquid culture, grown to an appropriate OD, rendered electrocompetent, and subjected to another round of editing 8088. This method of enrichment of edited cells is particularly desirable as may be performed in a high throughput manner and does not require plating cells and is automatable. Induction at step 8067 can take place by, e.g., using a pL promoter system where the pL promoter is induced by raising the temperature of the cells in the medium to 42° C. for, e.g., one to many hours to induce expression of the nuclease and gRNA for cutting and editing. Once editing has been induced, the temperature of the culture 8082 is returned to 30° C.

In one method 8081, the cells from the bulk liquid culture are plated and the slow-growing colonies are selected 8086. In edited cells, cell viability is compromised in the period after editing is induced. The selection method shown in FIG. 8H (e.g., selecting slow growing colonies 8081) takes advantage of the growth lag in colonies of edited cells to identify edited cells. In some embodiments, the colony size of the edited cells is 20% smaller than colonies of non-edited cells. In some aspects the colony size of the edited cells is 30%, 40%, 50%, 60%, 70%, 80% or 90% smaller than the colonies of non-edited cells. In many embodiments, the colony size of the edited cells is 30-80% smaller than colonies of non-edited cells, and in some embodiments, the colony size of the edited cells is 40-70% smaller than colonies of non-edited cells.

The Reagent Cartridge

Figure 9A:
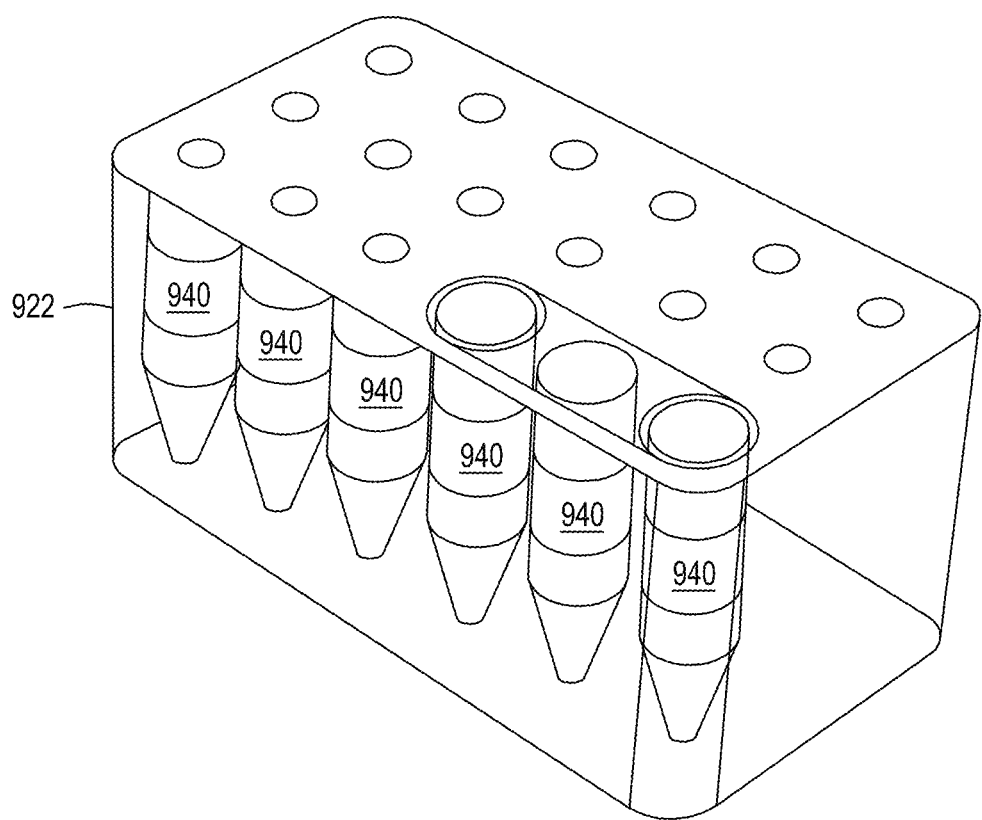
FIGS. 9A and 9B depict an example reagent cartridge for use in an automated multi-module cell editing instrument.

FIG. 9A depicts a reagent cartridge 922 including a set of eighteen tubes or vials 940. One or more of the tubes or vials 940, in some embodiments, is sealed with pierceable foil for access by an automated liquid handling system, such as a sipper or pipettor. In other embodiments, one or more of the tubes or vials may include a sealable access gasket. The top of each of the small tubes or vials, in some embodiments, is marked with machine-readable indicia (not illustrated) for automated identification of the contents. The machine-readable indicia may include a bar code, QR code, or other machine-readable coding. Other automated means for identifying a particular container can include color coding, symbol recognition (e.g., text, image, icon, etc.), and/or shape recognition (e.g., a relative shape of the container). Rather than being marked upon the vessel itself, in some embodiments, an upper surface of the cartridge body and/or the cartridge cover may contain machine-readable indicia for identifying contents. The small tubes or vials may each be of a same size. Alternatively, multiple volumes of tubes or vials may be provided in the reagent cartridge 922. In an illustrative example, each tube or vial may be designed to hold between 2 and 20 mL, between 4 and 10 mL, or about 5 mL. In some embodiments where only small volumes of some reagents are required, tube inserts may be used to accommodate small (e.g., microfuge) tubes in a larger receptacle (not shown).

In an illustrative example, the tubes or vials may each hold one the following materials: a vector backbone, oligonucleotides, reagents for nucleic acid assembly, a user-supplied cell sample, an inducer agent, magnetic beads in buffer, ethanol, an antibiotic for cell selection, reagents for eluting cells and nucleic acids, an oil overlay, other reagents, and cell growth and/or recovery media. In addition, the cell transformation module such as the flow-through electroporation device described above optionally may be part of the reagent cartridge.

Figure 9B:
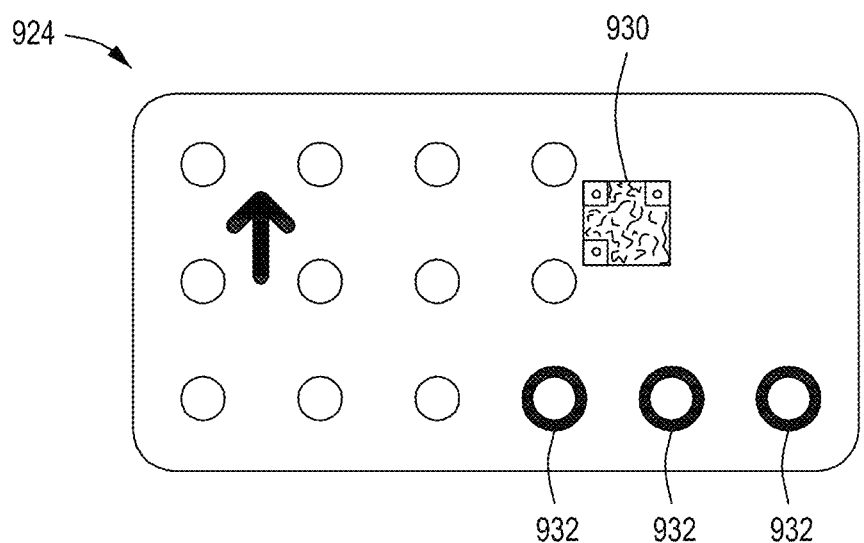

In some implementations, a cover 924 as seen in FIG. 9B secures the tubes or vials 940 within the cartridge body 922 of FIG. 9A. Turning to FIG. 9B, the cover 924 may include apertures for access to each of the small tubes or vials 940. Three large apertures 932 are outlined in a bold band to indicate positions to add user-supplied materials. The user-supplied materials, for example, may include a vector backbone, oligonucleotides, and a cell sample. Further, the cover 924 may include machine-readable indicia 930 for identifying the type of cartridge (e.g., accessing a map of the cartridge contents). Alternatively, each aperture may be marked separately with the individual contents. In some implementations, to ensure positioning of user-supplied materials, the vials or tubes provided for filling in the lab environment may have unique shapes or sizes such that the cell sample vial or tube only fits in the cell sample aperture, the oligonucleotides vial or tube only fits in the oligonucleotides aperture, and so on.

Use of the Cell Growth Device

Figure 10:
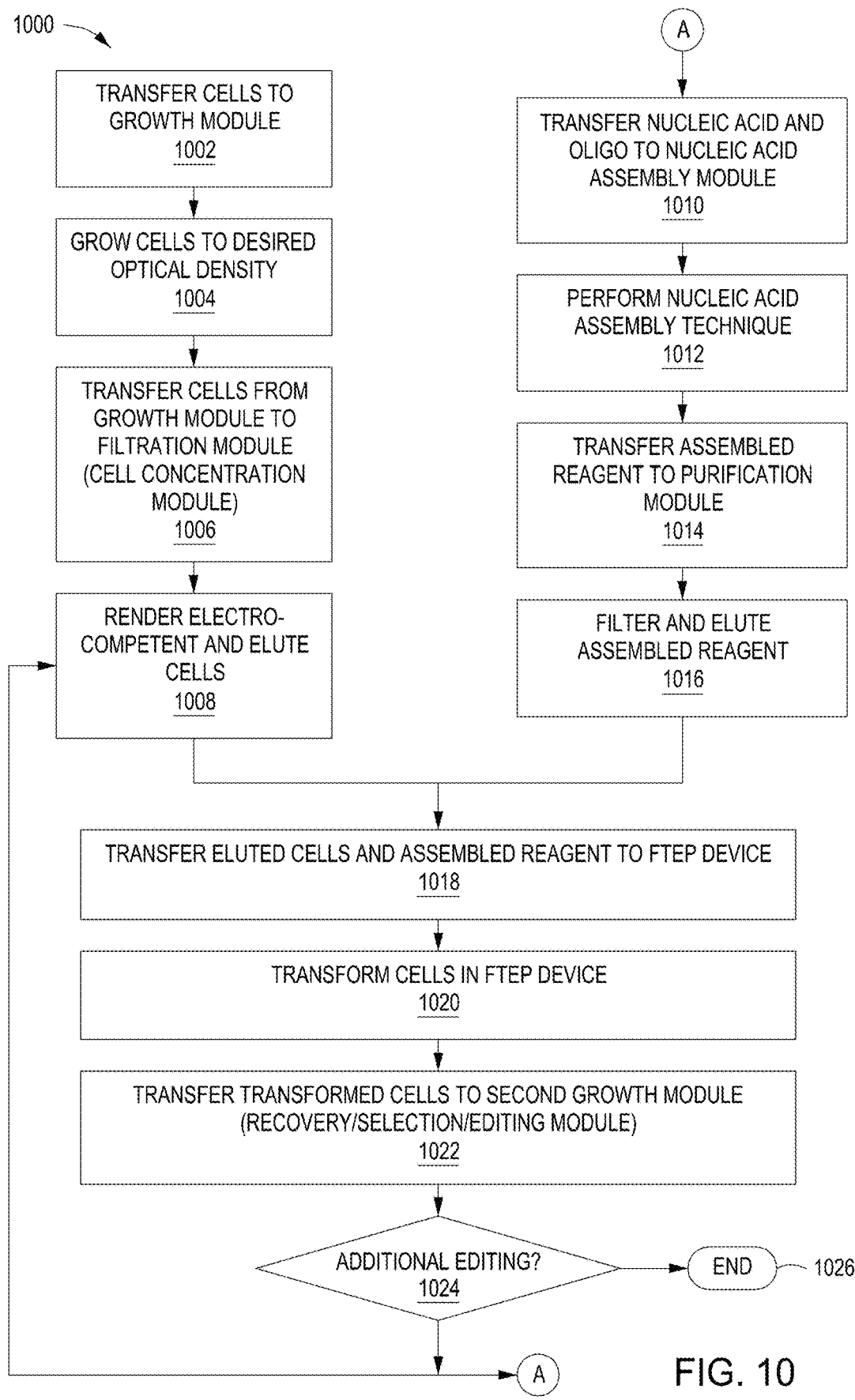
FIG. 10 is a flow chart of an example method for automated multi-module cell editing to produce the cell libraries as described herein.

FIG. 10 is a flow chart of an example method 1000 for using an automated multi-module cell editing instrument such as the systems illustrated in FIGS. 4A-4D. A processing system, for example, directs the processing stage of the method 1000. For example, a software script may identify settings for each processing stage and instructions for movement of a robotic handling system to perform the actions of the method 1000. In some embodiments, a software instruction script may be identified by a cartridge supplied to the automated multi-module cell editing instrument. For example, the cartridge may include machine-readable indicia, such as a bar code or QR code, including identification of a script stored in a memory of the automated multi-module cell editing instrument. In another example, the cartridge may contain a downloadable script embedded in machine-readable indicia such as a radio frequency (RF) tag. In other embodiments, the user may identify a script, for example through downloading the script via a wired or wireless connection to the processing system of the automated multi-module cell editing instrument or through selecting a stored script through a user interface of the automated multi-module cell editing instrument. In a particular example, the automated multi-module cell editing instrument may include a touch screen interface for submitting user settings and activating cell processing.

In some implementations, the method 1000 begins with transferring cells to a cell growth module (1002). The growth module may be any growth module amendable to automation such as, for example, the cell growth module 550 described in relation to FIGS. 5B-5D. In a particular example, the processing system may direct the robotic handling system to transfer cells to the growth module. In another example, the cells may be transferred from one a reagent cartridge to the growth module by the robotic handling system. In some embodiments, the growth vial may contain growth media and be supplied, e.g., as part of a kit. In other embodiments, the growth vial may be filled with medium transferred, e.g., via the liquid handling device, from a reagent container.

In some embodiments, prior to transferring the cells (e.g., from the reagent cartridge or from a vial added to the instrument), machine-readable indicia may be scanned upon the vial or other container situated in a position designated for cells to confirm that the vial or container is marked as containing cells. Further, the machine-readable indicia may indicate a type of cells provided to the instrument. The type of cells, in some embodiments, may cause the instrument to select a particular processing script (e.g., series of instructions for the robotic handling system and settings and activation of the various modules).

In some implementations, the cells are grown in the growth module to a desired optical density (1004). For example, the processing system may manage a temperature setting of the growth module for incubating the cells during the growth cycle. The processing system may further receive sensor signals from the growth module indicative of optical density and analyze the sensor signals to monitor growth of the cells. In some embodiments, a user may set growth parameters for managing growth of the cells. For example, temperature, and the degree of agitation of the cells. Further, in some embodiments, the user may be updated regarding growth process. The updates, in some examples, may include a message presented on a user interface of the automated multi-module cell editing instrument, a text message to a user's cell phone number, an email message to an email account, or a message transmitted to an app executing upon a portable electronic device (e.g., cell phone, tablet, etc.). Responsive to the messages, in some embodiments, the user may modify parameters, such as temperature, to adjust cell growth. For example, the user may submit updated parameters through a user interface of the automated multi-module cell editing instrument or through a portable computing device application in communication with the automated multi-module cell editing instrument, such as a user interface (see element 450 of FIG. 4B).

Although described in relation to optical density, in other implementations cell growth within the growth module may be monitored using a different measure of cell density and physiological state such as, in some examples, pH, dissolved oxygen, released enzymes, acoustic properties, and electrical properties.

In some implementations, upon reaching the desired optical density (1004), the cells are transferred from the growth module to a filtration module or cell wash and concentration module (1006). The robotic handling system, for example, may transfer the cells from the growth module to the cell concentration module. The cell concentration module, for example, may be (and typically is) designed to render the cells electrocompetent. See FIG. 6A-6I in relation to the TFF device, above. The cells are rendered electrocompetent and eluted in the filtration module or cell wash and concentration module (1008). The cells may be eluted using a wash solution. For example, the cells may be eluted using reagents from a reagent supply.

Once the cells have been rendered electrocompetent and suspended in an appropriate volume such as 50 µL to 10 mL, or 100 µL to 80 mL, or 150 µL to 8 mL, or 250 µL to 7 mL, or 500 µL to 6 mL, or 750 µL to 5 mL for transformation (1006), the cells are transferred to, e.g., an FTEP module (1018). The robotic handling system, for example, may transfer the cells from the filtration module to the FTEP. The filtration module may be physically coupled to the FTEP device, or these modules may be separate.

In some implementations, nucleic acids are prepared outside of the automated multi-module cell editing instrument. For example, an assembled vector or other nucleic acid assembly may be included as a reagent by a user prior to running the transformation process and other processes in the method 1000.

However, in other implementations, nucleic acids are prepared by the automated multi-module cell editing instrument. A portion of the following steps 1010 through 1016, in some embodiments, are performed in parallel with a portion of steps 1002 through 1008. At least a portion of the following steps, in some embodiments, are performed before and/or after steps 1002 through 1008.

In some implementations, nucleic acids such as an editing oligonucleotide and a vector backbone, as well as in some examples, enzymes and other reaction components are transferred to a nucleic acid assembly module (1010). The nucleic acid assembly module may be configured to perform one or more of a wide variety of different nucleic acid assembly techniques in an automated fashion. Nucleic acid assembly techniques that can be performed in the nucleic acid assembly module may include, but are not limited to, those assembly methods that use restriction endonucleases, including PCR, BioBrick assembly, Type IIS cloning, GoldenGate assembly, and Ligase Cycling Reaction. In other examples, the nucleic acid assembly module may perform an assembly technique based on overlaps between adjacent parts of the nucleic acids, such as Gibson Assembly®, CPEC, SLIC, Ligase Cycling, etc., as described above. Additional example assembly methods that may be performed by the nucleic acid assembly module include gap repair in yeast, gateway cloning and topoisomerase-mediated cloning. In a particular example, the processing system may direct the robotic handling system to transfer nucleic acids to the nucleic acid assembly module. In another example, the nucleic acids may be transferred from a reagent cartridge to a nucleic acid assembly module by the robotic handling system.

In some embodiments—prior to transferring each of the nucleic acid samples, the enzymes, and other reaction components—machine-readable indicia may be scanned upon the vials or other containers situated in positions designated for these materials to confirm that the vials or containers are marked as containing the anticipated material. Further, the machine-readable indicia may indicate a type of one or more of the nucleic acid samples, the enzymes, and other reaction components provided to the instrument. The type(s) of materials, in some embodiments, may cause the instrument to select a particular processing script (e.g., series of instructions for the robotic handling system to identify further materials and/or settings and activation of the nucleic acid assembly module).

In some embodiments, the nucleic acid assembly module is temperature controlled depending upon the type of nucleic acid assembly used. For example, when PCR is utilized in the nucleic acid assembly module, the module can have a thermocycling capability allowing the temperatures to cycle between denaturation, annealing and extension steps. When single temperature assembly methods are utilized in the nucleic acid assembly module, the module can have the ability to reach and hold at the temperature that optimizes the specific assembly process being performed.

Temperature control, in some embodiments, is managed by a processing system of the automated multi-module cell editing instrument, such as the processing system. These temperatures and the duration of maintaining the temperatures can be determined by a preprogrammed set of parameters (e.g., identified within the processing script or in another memory space accessible by the processing system), or manually controlled by the user through interfacing with the processing system.

Once sufficient time has elapsed for the assembly reaction to take place, in some implementations, the nucleic acid assembly may be transferred to a purification module (1014). The processing system, for example, may monitor timing of the assembly reaction based upon one or more of the type of reaction, the type of materials, and user settings provided to the automated multi-module cell editing instrument. The robotic handling system, for example, may transfer the nucleic acid assembly to the purification module through a sipper or pipettor interface. In another example, the robotic handling system may transfer a vial containing the nucleic acid assembly from a chamber of the nucleic acid assembly module to a chamber of the de-salt/purification module.

In some implementations, the nucleic acid assembly is de-salted and eluted at the purification module (1016). The purification module, for example, may remove unwanted components of the nucleic acid assembly mixture (e.g., salts, minerals, etc.). In some embodiments, the purification module concentrates the assembled nucleic acids into a smaller volume that the nucleic acid assembly volume. Examples of methods for exchanging liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc. For example, one or more micro-concentrators fitted with anisotropic, hydrophilic-generated cellulose membranes of varying porosities may be used. In another example, the de-salt/purification module may process a liquid sample including a nucleic acid and an ionic salt by contacting the mixture with an ion exchanger including an insoluble phosphate salt, removing the liquid, and eluting nucleic acid from the ion exchanger.

In an illustrative embodiment, the nucleic acid assembly may be combined with magnetic beads, such as SPRI beads, in a chamber of a purification module. The nucleic acid assembly may be incubated at a set temperature for sufficient time for the assembled nucleic acids to bind to the magnetic beads. After incubation, a magnet may be engaged proximate to the chamber so that the nucleic acid assembly can be washed and eluted. Once the nucleic acid assembly has been eluted, the nucleic acid assembly is transferred to the transformation module (1018). The robotic handling system, for example, may transfer the assembled nucleic acids to the transformation module through a sipper or pipettor interface to the FTEP as described above. For example, the de-salted assembled nucleic acids, during the transfer, may be combined with the electrocompetent cells from step 108. In other embodiments, the transformation module may accept each of the electrocompetent cells and the nucleic acid assembly separately and enable the mixing (e.g., open one or more channels to combine the materials in a shared chamber).

The cells are transformed in the FTEP module (1020). A buffer or medium may be transferred to the transformation module and added to the cells so that the cells may be suspended in a buffer or medium that is favorable for cell survival during electroporation. Prior to transferring the buffer or medium, machine-readable indicia may be scanned upon the vial or other container or reservoir situated in the position designated for the buffer or medium to confirm the contents of the vial, container, or reservoir. Further, the machine-readable indicia may indicate a type of buffer or medium provided to the instrument. The type of buffer or medium, in some embodiments, may cause the instrument to select a particular processing script (e.g., settings and activation of the transformation module appropriate for the particular buffer or medium). For bacterial cell electroporation, low conductance mediums, such as water or glycerol solutions, may be used to reduce the heat production by transient high current. For yeast cells a sorbitol solution may be used. For mammalian cell electroporation, cells may be suspended in a highly conductive medium or buffer, such as MEM, DMEM, IMDM, RPMI, Hanks', PBS, HBSS, HeBS and Ringer's solution. In a particular example, the robotic handling system may transfer a buffer solution to FTEP module from the reagent cartridge. As described in relation to FIGS. 7A-7E, the FTEP device may be a disposable FTEP device and/or the FTEP device may be provided as part of the reagent cartridge. Alternatively, as shown in FIG. 4A, the FTEP device may a separate module.

Once transformed, the cells are transferred to a second growth/recovery/editing module (1022) such as the cell growth module described in relation to FIGS. 5A-5D. The robotic handling system, for example, may transfer the transformed cells to the second growth module through a sipper or pipettor interface. In another example, the robotic handling system may transfer a vial containing the transformed cells from a chamber of the transformation module to a chamber of the second growth module.

The second growth module, in some embodiments, acts as a recovery module, allowing the cells to recover from the transformation process. In other embodiments, the cells may be provided to a separate recovery module prior to being transported to the second growth module. During recovery, the second growth module allows the transformed cells to uptake and, in certain aspects, integrate the introduced nucleic acids into the genome of the cell. The second growth module may be configured to incubate the cells at any user-defined temperature optimal for cell growth, preferably 25°, 30°, or 37° C.

In some embodiments, the second growth module behaves as a selection module, selecting the transformed cells based on an antibiotic or other reagent. In one example, the RNA-guided nuclease (RGN) protein system is used for selection to cleave the genomes of cells that have not received the desired edit. In the example of an antibiotic selection agent, the antibiotic may be added to the second growth module to enact selection. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, or chloramphenicol-resistance gene. The robotic handling system, for example, may transfer the antibiotic to the second growth module through a sipper or pipettor interface. In some embodiments, removing dead cell background is aided using lytic enhancers such as detergents, osmotic stress by hyponic wash, temperature, enzymes, proteases, bacteriophage, reducing agents, or chaotropes. The processing system, for example, may alter environmental variables, such as temperature, to induce selection, while the robotic handling system may deliver additional materials (e.g., detergents, enzymes, reducing agents, etc.) to aid in selection. In other embodiments, cell removal and/or media exchange by filtration is used to reduce dead cell background.

In further embodiments, in addition to or as an alternative to applying selection, the second growth module serves as an editing module, allowing for genome editing in the transformed cells. Alternatively, in other embodiments the cells post-recovery and selection (if performed) are transferred to a separate editing module. As an editing module, the second growth module induces editing of the cells' genomes, e.g., through facilitating expression of the introduced nucleic acids. Expression of the nuclease and/or editing cassette nucleic acids may involve one or more of chemical, light, viral, or temperature induction methods. The second growth module, for example, may be configured to heat or cool the cells during a temperature induction process. In a particular illustration, the cells may be induced by heating at 42° C.-50° C. Further to the illustration, the cells may then be are cooled to 0-10° C. after induction. In the example of chemical or viral induction, an inducing agent may be transferred to the second growth module to induce editing. If an inducible nuclease and/or editing cassette was introduced to the cells during editing, it can be induced through introduction of an inducer molecule. The inducing agent or inducer molecule, in some implementations, is transferred to the second growth module by the robotic handling system, e.g., through a pipettor or sipper interface.

In some implementations, if no additional cell editing is desired (1024), the cells may be transferred from the cell growth module to a storage unit for later removal from the automated multi-module cell editing instrument (1026). The robotic handling system, for example, may transfer the cells to a storage unit through a sipper or pipettor interface. In another example, the robotic handling system may transfer a vial containing the cells from a chamber of the second growth module to a vial or tube within the storage unit.

In some implementations, if additional cell editing is desired (1024), the cells may be transferred to the same or a different filtration module and rendered electrocompetent (1008). Further, in some embodiments, a new assembled nucleic acid sample may be prepared by the nucleic acid assembly module at this time, or, alternatively, a second fully assembled nucleic acid may be directly introduced to the cells. Prior to recursive editing, in some embodiments, the automated multi-module cell editing instrument may require additional materials be supplied by the user, e.g., through the introduction of one or more separate reagents vials or cartridge.

The steps may be the same or different during the second round of editing. For example, in some embodiments, upon a subsequent execution of step 1004, a selective growth medium is transferred to the growth module to enable selection of edited cells from the first round of editing. The robotic handling system may transfer the selective growth medium from a vial or container in a reagent cartridge situated in a position designated for selective growth medium. Prior to transferring the selective growth medium, machine-readable indicia may be scanned upon the vial or other container or reservoir situated in the position designated for the selective growth medium to confirm the contents of the vial, container, or reservoir. Further, the machine-readable indicia may indicate a type of selective growth medium provided to the instrument. The type of selective growth medium, in some embodiments, may cause the instrument to select a particular processing script (e.g., settings and activation of the growth module appropriate for the particular selective growth medium). Particular examples of recursive editing workflows are described in relation to FIG. 13.

In some implementations, the method 1000 can be timed to introduce materials and/or complete the editing cycle or growth cycle in coordination with a user's schedule. For example, the automated multi-module cell editing instrument may provide the user the ability to schedule completion of one or more cell processing cycles (e.g., one or more recursive edits) such that the method 1000 is enacted with a goal of completion at the user's preferred time. The time scheduling, for example, may be set through a user interface. For illustration only, a user may set completion of a first cycle to 4:00 PM so that the user can supply additional cartridges of materials to the automated multi-module cell editing instrument to enable overnight processing of another round of cell editing. Thus a user may time the programs so that two or more cycles may be programmed in a specific time period, e.g., a 24-hour period.

In some implementations, throughout the method 1000, the automated multi-module cell editing instrument may alert the user to its current status. For example, the user interface may present a graphical indication of the present stage of processing. In a particular example, a front face of the automated multi-module call processing instrument may be overlaid with a user interface (e.g., touch screen) that presents an animated graphic depicting present status of the cell processing. The user interface may further present any user and/or default settings associated with the current processing stage (e.g., temperature setting, time setting, etc.). In certain implementations, the status may be communicated to a user via wireless communications controller.

Although illustrated as a particular series of operations, in other embodiments, more or fewer steps may be included in the method 1000. For example, in some embodiments, prior to engaging in each round of editing, the contents of reservoirs, cartridges, and/or vials may be screened to confirm appropriate materials are available to proceed with processing. For example, in some embodiments, one or more imaging sensors (e.g., barcode scanners, cameras, etc.) may confirm contents at various locations within the housing of the automated multi-module cell editing instrument. In one example, multiple imaging sensors may be disposed within the housing of the automated multi-module cell editing instrument, each imaging sensor configured to detect one or more materials (e.g., machine-readable indicia such as barcodes or QR codes, shapes/sizes of materials, etc.). In another example, at least one imaging sensor may be moved by the robotic handling system to multiple locations to detect one or more materials. In further embodiments, one or more weight sensors may detect presence or absence of disposable or replaceable materials. In an illustrative example, the transfer tip supply holder may include a weight sensor to detect whether or not tips have been loaded into the region. In another illustrative example, an optical sensor may detect that a level of liquid waste has reached a threshold level, requiring disposal prior to continuation of cell processing or addition of liquid if the minimum level has not been reached to proceed. Requests for additional materials, removal of waste supplies, or other user interventions (e.g., manual cleaning of one or more elements, etc.), in some implementations, are presented on a graphical user interface of the automated multi-module cell editing instrument. The automated multi-module cell editing instrument, in some implementations, contacts the user with requests for new materials or other manual interventions, for example through a software app, email, or text message.

Figure 11:
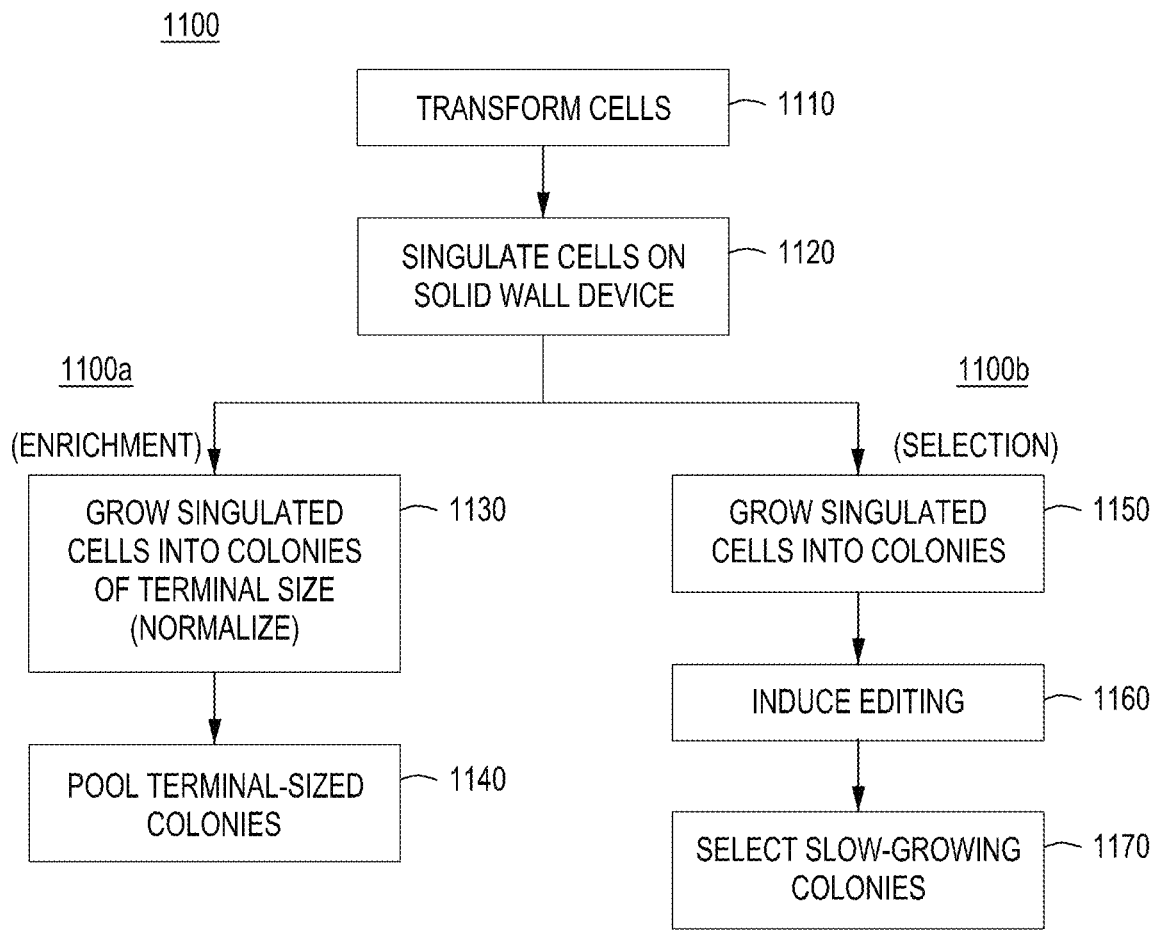
FIG. 11 is a simplified flow chart of two exemplary methods (1100a and 1100b) that may be performed by an automated multi-module cell editing instrument comprising a singulation device.

FIG. 11 shows simplified flow charts for two alternative exemplary methods 1100a and 1100b for singulating cells for enrichment (1100a) and for cherry picking (1100b). Looking at FIG. 11, method 1100a begins by transforming cells 1110 with the components necessary to perform nucleic acid-guided nuclease editing. For example, the cells may be transformed simultaneously with separate engine and editing vectors; the cells may already be expressing the nuclease (e.g., the cells may have already been transformed with an engine vector or the coding sequence for the nuclease may be stably integrated into the cellular genome) such that only the editing vector needs to be transformed into the cells; or the cells may be transformed with a single vector comprising all components required to perform nucleic acid-guided nuclease genome editing.

As described above, a variety of delivery systems can be used to introduce (e.g., transform or transfect) nucleic acid-guided nuclease editing system components into a host cell 1110. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of interest, particularly in the context of a multi-module cell editing instrument is the use of electroporation, particularly flow-through electroporation (either as a stand-alone instrument or as a module in an automated multi-module system) as described in, e.g., U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/147,871, filed 30 Sep. 2018. If the solid wall singulation/growth/editing/normalization module is one module in an automated multi-module cell editing instrument, the cells are likely transformed in an automated cell transformation module.

After the cells are transformed with the components necessary to perform nucleic acid-guided nuclease editing, the cells are singulated in microwells in a, e.g., solid wall device 1120; that is, the cells are diluted (if necessary) in a liquid culture medium (in some embodiments, including Tween, at a concentration of 0.1% or less to effect a good distribution) so that the cells, when delivered to the solid wall device, fill the microwells of the solid wall device in a Poisson or substantial Poisson distribution. Singulation is accomplished when an average of ½ cell is delivered to each microwell; that is, where some microwells contain one cell and other microwells contain no cells.

Once the cells in this embodiment have been singulated in 1100*a*, the cells are actively editing, as the editing "machinery" is under the control of a constitutive promoter. As the cells are editing, they are grown into colonies of terminal size 1130; that is, the colonies arising from the singulated cells are grown into colonies to a point where cell growth has peaked and is normalized or saturated for both edited and unedited cells. Normalization occurs as the nutrients in the medium around a growing cell colony are depleted and/or cell growth fills the microwells and further growth is constrained. Again, in the embodiment 1100*a* shown in FIG. 11, the editing components are under the control of a constitutive promoter; thus, editing begins immediately (or almost immediately) upon transformation. However, in other embodiments such as the embodiment shown in 1100*b* described below, one or both of the nuclease and the guide nucleic acid (as well as, e.g., the X red recombination system components in bacterial systems) may be under the control of an inducible promoter, in which case editing may be induced after, e.g., a desired number of cell doublings. Turning back to method 1100*a*, the terminal-size colonies are pooled 1140 by flushing the clonal cell colonies from the microwells to mix the cells from the normalized cell colonies. Again, because singulation overcomes growth bias from unedited cells or cells exhibiting fitness effects as the result of edits made, singulation/normalization alone enriches the total population of cells with cells that have been edited; that is, singulation combined with normalization (e.g., growing colonies to terminal size) allows for high-throughput enrichment of edited cells.

The method 1100*b* shown in FIG. 11 is similar to the method 1100*a* in that cells of interest are transformed 1110 with the components necessary to perform nucleic acid-guided nuclease editing. As described above, the cells may be transformed simultaneously with both the engine and editing vectors, the cells may already be expressing the nuclease (e.g., the cells may have already been transformed with an engine vector or the coding sequence for the nuclease may be stably integrated into the cellular genome) such that only the editing vector needs to be transformed into the cells, or the cells may be transformed with a single vector comprising all components required to perform nucleic acid-guided nuclease genome editing. Further, if the singulation/growth/editing/normalization solid wall module is one module in an automated multi-module cell editing instrument, cell transformation may be performed in an automated transformation module as described above.

After the cells are transformed with the components necessary to perform nucleic acid-guided nuclease editing, the cells are diluted (if necessary) in liquid medium so that the cells, when delivered to the solid wall device, fill the microwells of the solid wall device in a Poisson or substantial Poisson distribution.

Once the cells have been singulated in the microwells of the solid wall device 1120, the cells are allowed to grow to, e.g., between 2 and 150, or between 5 and 120, or between 10 and 100 doublings, establishing clonal colonies 1150. After colonies are established, in this embodiment 1100*b* editing is induced 1160 by, e.g., activating inducible promoters that control transcription of one or more of the components needed for nucleic acid-guided nuclease editing, such as, e.g., transcription of the gRNA, nuclease, or, in the case of bacteria, a recombineering system. Once editing is induced 1160, many of the edited cells in the clonal colonies die due to the double-strand DNA breaks that occur during the editing process; however, in a percentage of edited cells, the genome is edited and the double strand break is properly repaired. These edited cells then start growing and re-establish colonies; however, the growth of edited colonies tends to lag behind the growth of clonal colonies where an edit has not taken place. The small or slow-growing colonies (edited cells) are cherry picked 1170.

Figure 12:
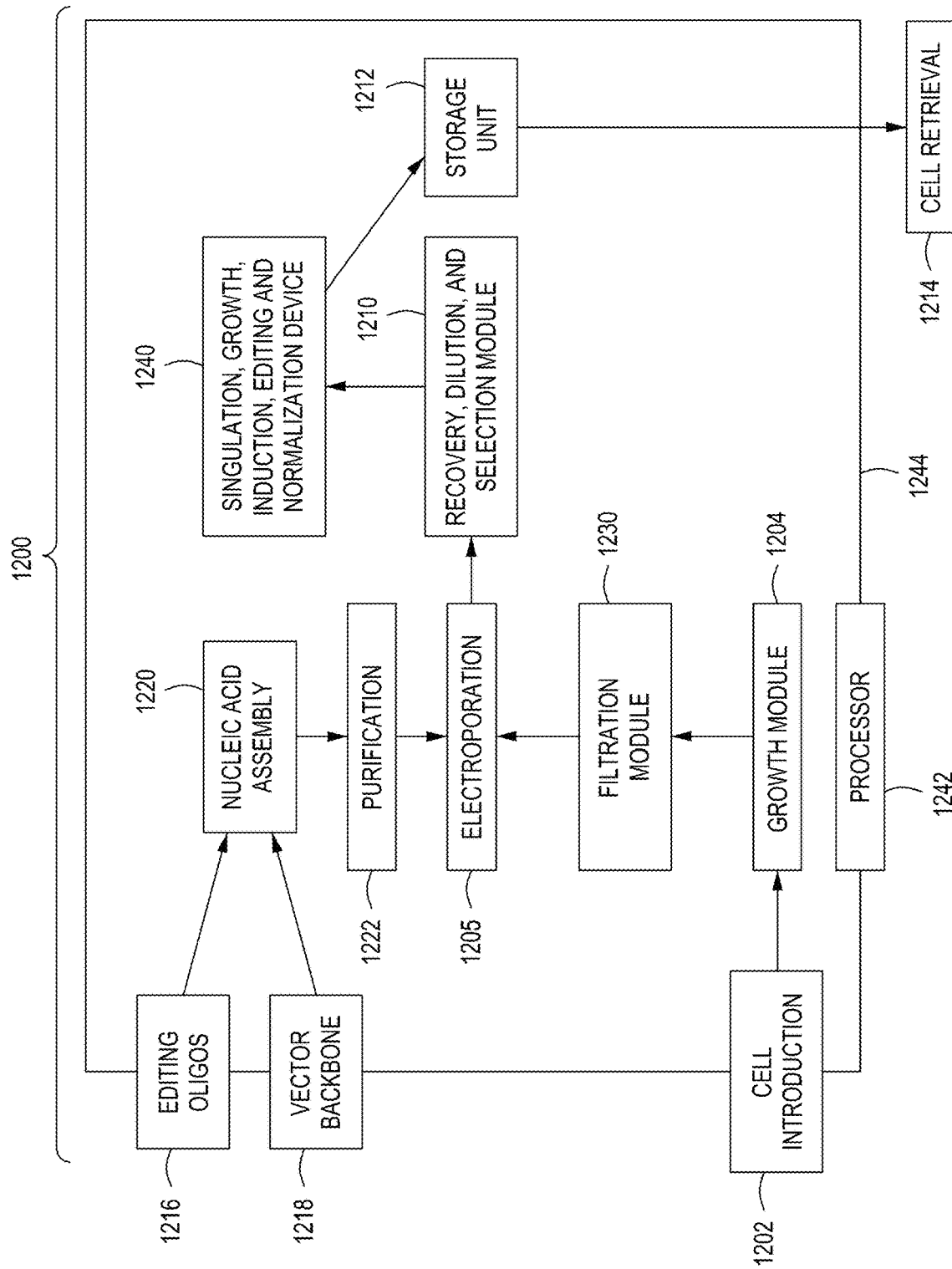
FIG. 12 is a simplified block diagram of an embodiment of an exemplary automated multi-module cell processing instrument comprising a solid wall singulation/growth/editing/normalization module.

FIG. 12 is a simplified block diagram of an embodiment of an exemplary automated multi-module cell processing instrument comprising a solid wall singulation/growth/editing/normalization module for enrichment for edited cells. The cell processing instrument 1200 may include a housing 1244, a reservoir of cells to be transformed or transfected 1202, and a growth module (a cell growth device) 1204. The cells to be transformed are transferred from a reservoir to the growth module to be cultured until the cells hit a target OD. Once the cells hit the target OD, the growth module may cool or freeze the cells for later processing, or the cells may be transferred to a filtration module 1230 where the cells are rendered electrocompetent and concentrated to a volume optimal for cell transformation. Once concentrated, the cells are then transferred to the electroporation device 1208 (e.g., transformation/transfection module). Exemplary electroporation devices of use in the automated multi-module cell processing instruments for use in the multi-module cell processing instrument include flow-through electroporation devices such as those described in U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/147,871, filed 30 Sep. 2018 all of which are herein incorporated by reference in their entirety.

In addition to the reservoir for storing the cells, the system 1200 may include a reservoir for storing editing oligonucleotide cassettes 1216 and a reservoir for storing an expression vector backbone 1218. Both the editing oligonucleotide cassettes and the expression vector backbone are transferred from the reagent cartridge to a nucleic acid assembly module 1220, where the editing oligonucleotide cassettes are inserted into the expression vector backbone. The assembled nucleic acids may be transferred into an optional purification module 1222 for desalting and/or other purification and/or concentration procedures needed to prepare the assembled nucleic acids for transformation. Alternatively, pre-assembled nucleic acids, e.g., an editing vector, may be stored within reservoir 1216 or 1218. Once the processes carried out by the purification module 1222 are complete, the assembled nucleic acids are transferred to, e.g., an electroporation device 1205, which already contains the cell culture grown to a target OD and rendered electrocompetent via filtration module 1230. In electroporation device 1208, the assembled nucleic acids are introduced into the cells. Following electroporation, the cells are transferred into a combined recovery/selection module 1210.

Following recovery, and, optionally, selection, the cells are transferred to a singulation, editing, and growth module 1240, where the cells are diluted and compartmentalized such that there is an average of one cell per compartment. Once singulated, the cells are allowed to grow for a predetermined number of doublings. Once these initial colonies are established, editing is induced and the edited cells are allowed to establish colonies, which are grown to terminal size (e.g., the colonies are normalized). In some embodiments, editing is induced by one or more of the editing components being under the control of an inducible promoter. In some embodiments, the inducible promoter is activated by a rise in temperature and "deactivated" by lowering the temperature. Alternatively, in embodiments where the singulation device is a solid wall device comprising a filter forming the bottom of the microwell, the solid wall device can be transferred to a plate (e.g., agar plate or even to liquid medium) comprising a medium with a component that activates or induced editing, then transferred to a medium that deactivates editing. Once the colonies are grown to terminal size, the colonies are pooled. Again, singulation overcomes growth bias from unedited cells and growth bias resulting from fitness effects of different edits.

The recovery, selection, singulation, induction, editing and growth modules may all be separate, may be arranged and combined as shown in FIG. 12, or may be arranged or combined in other configurations. In certain embodiments, all of recovery, selection, singulation, growth, editing, and normalization are performed in a solid wall device. Alternatively, recovery, selection, and dilution, if necessary, are performed in liquid medium in a separate vessel (module), then transferred to the solid wall singulation/growth/induction/editing/normalization module.

Once the normalized cell colonies are pooled, the cells may be stored, e.g., in a storage module 1212, where the cells can be kept at, e.g., 4° C. until the cells are retrieved for further study. Alternatively, the cells may be used in another round of editing. The multi-module cell processing instrument is controlled by a processor 1242 configured to operate the instrument based on user input, as directed by one or more scripts, or as a combination of user input or a script. The processor 1242 may control the timing, duration, temperature, and operations of the various modules of the system 500 and the dispensing of reagents. For example, the processor 1242 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

The automated multi-module cell processing instrument 1200 is a nuclease-directed genome editing system and can be used in single editing systems (e.g., introducing one or more edits to a cellular genome in a single editing process). The system of FIG. 13, described below, is configured to perform sequential editing, e.g., using different nuclease-directed systems sequentially to provide two or more genome edits in a cell; and/or recursive editing, e.g. utilizing a single nuclease-directed system to introduce sequentially two or more genome edits in a cell.

Figure 13:
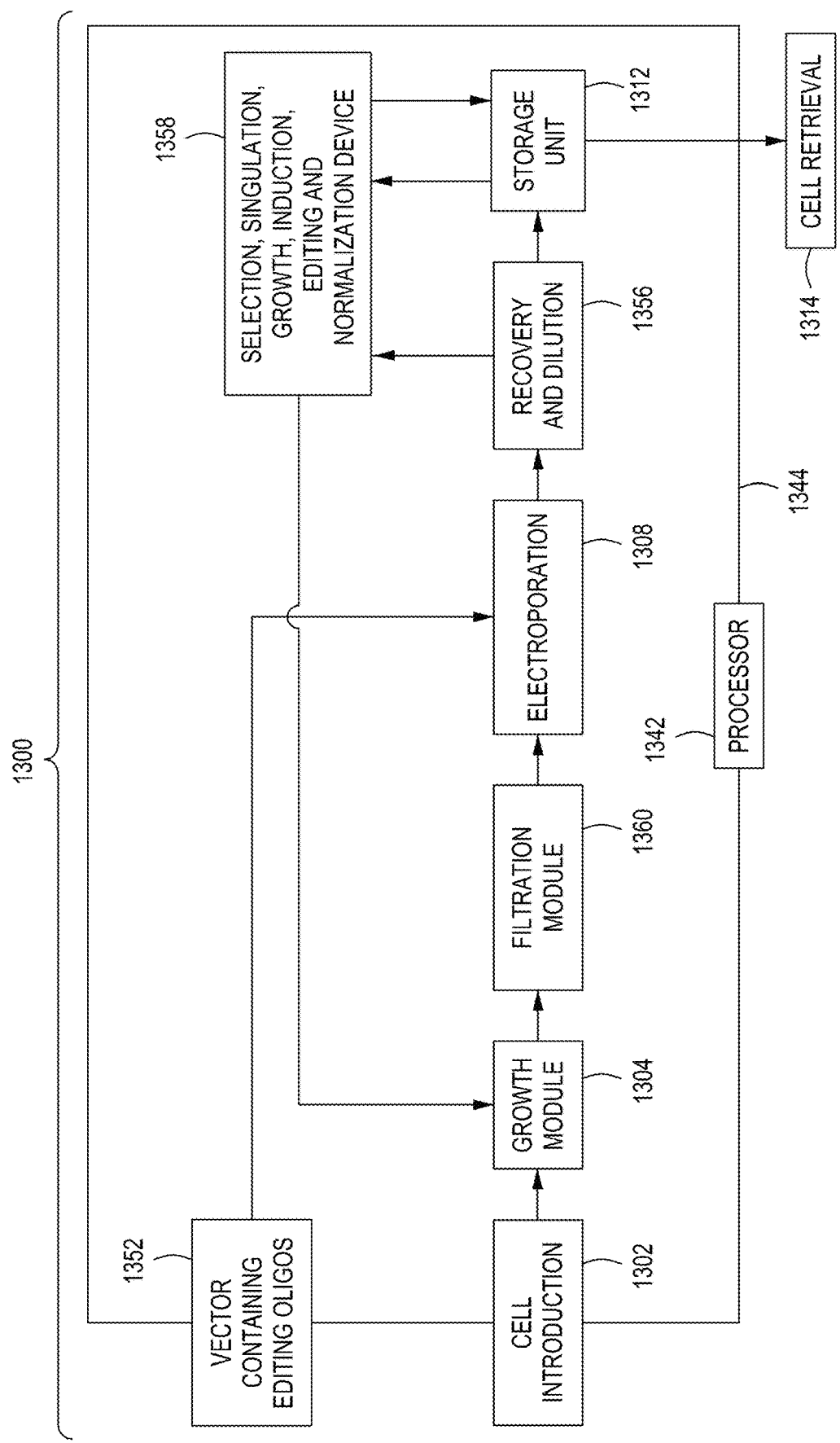
FIG. 13 is a simplified block diagram of an alternative embodiment of an exemplary automated multi-module cell processing instrument comprising a solid wall singulation/growth/editing/normalization module.

FIG. 13 illustrates another embodiment of a multi-module cell processing instrument. This embodiment depicts an exemplary system that performs recursive gene editing on a cell population. As with the embodiment shown in FIG. 12, the cell processing instrument 1300 may include a housing 1344, a reservoir for storing cells to be transformed or transfected 1302, and a cell growth module (comprising, e.g., a rotating growth vial) 1304. The cells to be transformed are transferred from a reservoir to the cell growth module to be cultured until the cells hit a target OD. Once the cells hit the target OD, the growth module may cool or freeze the cells for later processing or transfer the cells to a filtration module 1360 where the cells are subjected to buffer exchange and rendered electrocompetent, and the volume of the cells may be reduced substantially. Once the cells have been concentrated to an appropriate volume, the cells are transferred to electroporation device 1308. In addition to the reservoir for storing cells, the multi-module cell processing instrument includes a reservoir for storing the vector pre-assembled with editing oligonucleotide cassettes 1352. The pre-assembled nucleic acid vectors are transferred to the electroporation device 1308, which already contains the cell culture grown to a target OD. In the electroporation device 1308, the nucleic acids are electroporated into the cells. Following electroporation, the cells are transferred into an optional recovery module 1356, where the cells are allowed to recover briefly post-transformation.

After recovery, the cells may be transferred to a storage module 1312, where the cells can be stored at, e.g., 4° C. for later processing, or the cells may be diluted and transferred to a selection/singulation/growth/induction/editing/normalization module 1358. In the singulation/edit/growth module 1358, the cells are arrayed such that there is an average of one cell per microwell. The arrayed cells may be in selection medium to select for cells that have been transformed or transfected with the editing vector(s). Once singulated, the cells grow through 2-50 doublings and establish colonies. Once colonies are established, editing is induced by providing conditions (e.g., temperature, addition of an inducing or repressing chemical) to induce editing. Once editing is initiated and allowed to proceed, the cells are allowed to grow to terminal size (e.g., normalization of the colonies) in the microwells and then can be flushed out of the microwells and pooled, then transferred to the storage (or recovery) unit 1314 or can be transferred to a growth module 1304 for another round of editing. In between pooling and transfer to a growth module, there may be one or more additional steps, such as cell recovery, medium exchange, cells concentration, etc., by, e.g., filtration. Note that the selection/singulation/growth/induction/editing and normalization modules may be the same module, where all processes are performed in the solid wall device, or selection and/or dilution may take place in a separate vessel before the cells are transferred to the solid wall singulation/growth/induction/editing/normalization module (solid wall device). As an alternative to singulation in, e.g., a solid wall device, the transformed cells may be grown in—and editing can be induced in—bulk liquid as described above in relation to FIGS. 8F-8H above. Once the putatively-edited cells are pooled, they may be subjected to another round of editing, beginning with growth, cell concentration and treatment to render electrocompetent, and transformation by yet another donor nucleic acid in another editing cassette via the electroporation module 1308.

In electroporation device 1308, the cells selected from the first round of editing are transformed by a second set of editing oligos (or other type of oligos) and the cycle is repeated until the cells have been transformed and edited by a desired number of, e.g., editing cassettes. The multi-module cell processing instrument exemplified in FIG. 13 is controlled by a processor 1342 configured to operate the instrument based on user input or is controlled by one or more scripts including at least one script associated with the reagent cartridge. The processor 1342 may control the timing, duration, and temperature of various processes, the dispensing of reagents, and other operations of the various modules of the instrument 1300. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 13, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine plasmid.

Figure 14:
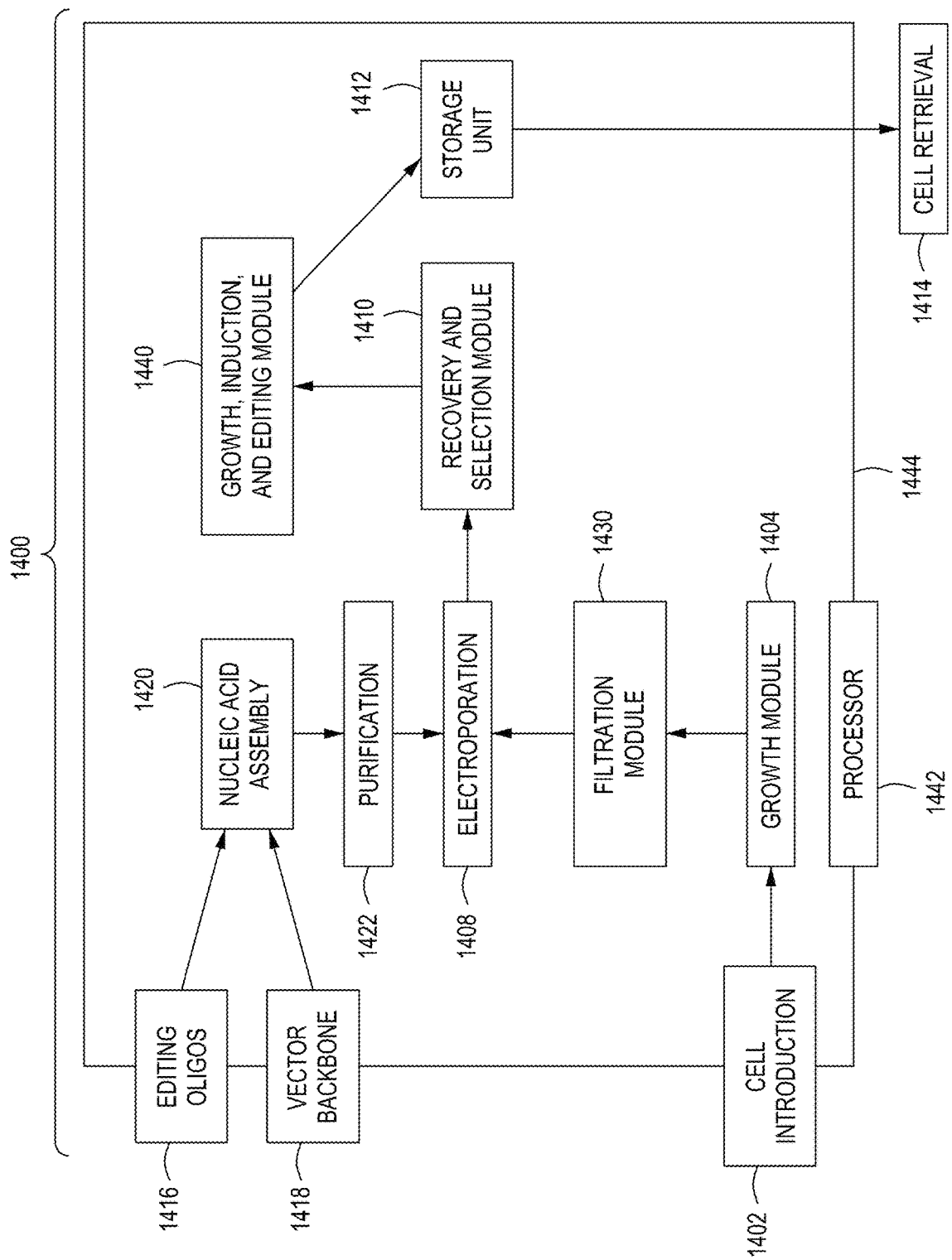
FIG. 14 is a simplified process diagram of an embodiment of an exemplary automated multi-module cell processing instrument.

FIG. 14 is a simplified block diagram of an embodiment of an exemplary automated multi-module cell processing instrument comprising a bulk liquid growth module for induced editing and enrichment for edited cells as described above in relation to FIGS. 8H-8F. The cell processing instrument 1400 may include a housing 1444, a reservoir of cells to be transformed or transfected 1402, and a growth module (a cell growth device) 1404. The cells to be transformed are transferred from a reservoir to the growth module to be cultured until the cells hit a target OD. Once the cells hit the target OD, the growth module may cool or freeze the cells for later processing, or the cells may be transferred to a filtration module 1430 where the cells are rendered electrocompetent and concentrated to a volume optimal for cell transformation. Once concentrated, the cells are then transferred to an electroporation device 1408 (e.g., transformation/transfection module). Exemplary electroporation devices of use in the automated multi-module cell processing instruments for use in the multi-module cell processing instrument include flow-through electroporation devices such as those described in U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/147,871, filed 30 Sep. 2018 all of which are herein incorporated by reference in their entirety.

In addition to the reservoir for storing the cells, the system 1400 may include a reservoir for storing editing cassettes 1416 and a reservoir for storing an expression vector backbone 1418. Both the editing oligonucleotide cassettes and the expression vector backbone are transferred from the reagent cartridge to a nucleic acid assembly module 1420, where the editing oligonucleotide cassettes are inserted into the expression vector backbone. The assembled nucleic acids may be transferred into an optional purification module 1422 for desalting and/or other purification and/or concentration procedures needed to prepare the assembled nucleic acids for transformation. Alternatively, pre-assembled nucleic acids, e.g., an editing vector, may be stored within reservoir 1416 or 1418. Once the processes carried out by the purification module 1422 are complete, the assembled nucleic acids are transferred to, e.g., an electroporation device 1408, which already contains the cell culture grown to a target OD and rendered electrocompetent via filtration module 1430. In electroporation device 1408, the assembled nucleic acids are introduced into the cells. Following electroporation, the cells are transferred into a combined recovery/selection module 1410. For examples of multi-module cell editing instruments, see U.S. Ser. Nos. 16/024,816 and 16/024,831, filed 30 Jun. 2018, both of which are herein incorporated by reference in their entirety.

Following recovery, and, optionally, selection, the cells are transferred to a growth, induction, and editing module (bulk liquid culture) 1440. The cells are allowed to grow until the cells reach the stationary growth phase (or nearly so), then editing is induced by induction of transcription of one or both of the nuclease and gRNA. In some embodiments, editing is induced by transcription of one or both of the nuclease and the gRNA being under the control of an inducible promoter. In some embodiments, the inducible promoter is a pL promoter where the promoter is activated by a rise in temperature and "deactivated" by lowering the temperature.

The recovery, selection, growth, induction, editing and storage modules may all be separate, may be arranged and combined as shown in FIG. 14, or may be arranged or combined in other configurations. In certain embodiments, recovery and selection are performed in one module, and growth, editing, and re-growth are performed in a separate module. Alternatively, recovery, selection, growth, editing, and re-growth are performed in a single module.

Once the cells are edited and re-grown (e.g., recovered from editing), the cells may be stored, e.g., in a storage module 1412, where the cells can be kept at, e.g., 4° C. until the cells are retrieved for further study. Alternatively, the cells may be used in another round of editing. The multi-module cell processing instrument is controlled by a processor 1442 configured to operate the instrument based on user input, as directed by one or more scripts, or as a combination of user input or a script. The processor 1442 may control the timing, duration, temperature, and operations of the various modules of the system 1400 and the dispensing of reagents. For example, the processor 1442 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Growth in the Cell Growth Module

One embodiment of the cell growth device as described herein was tested against a conventional cell shaker shaking a 5 ml tube and an orbital shaker shaking a 125 ml baffled flask to evaluate cell growth in bacterial and yeast cells. Additionally, growth of a bacterial cell culture and a yeast cell culture was monitored in real time using an embodiment of the cell growth device described herein.

Figure 15:
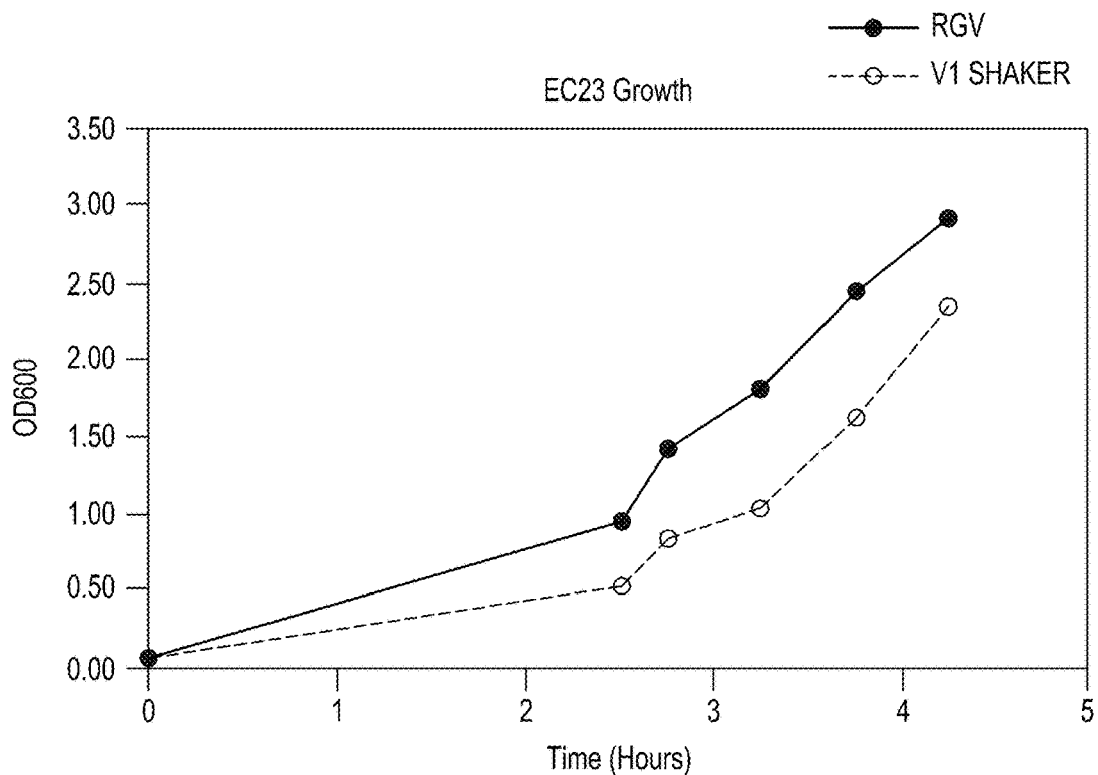
FIG. 15 is a graph demonstrating the effectiveness of a 2-paddle rotating growth vial and cell growth device as described herein for growing an EC23 cell culture vs. a conventional cell shaker.
Figure 16:
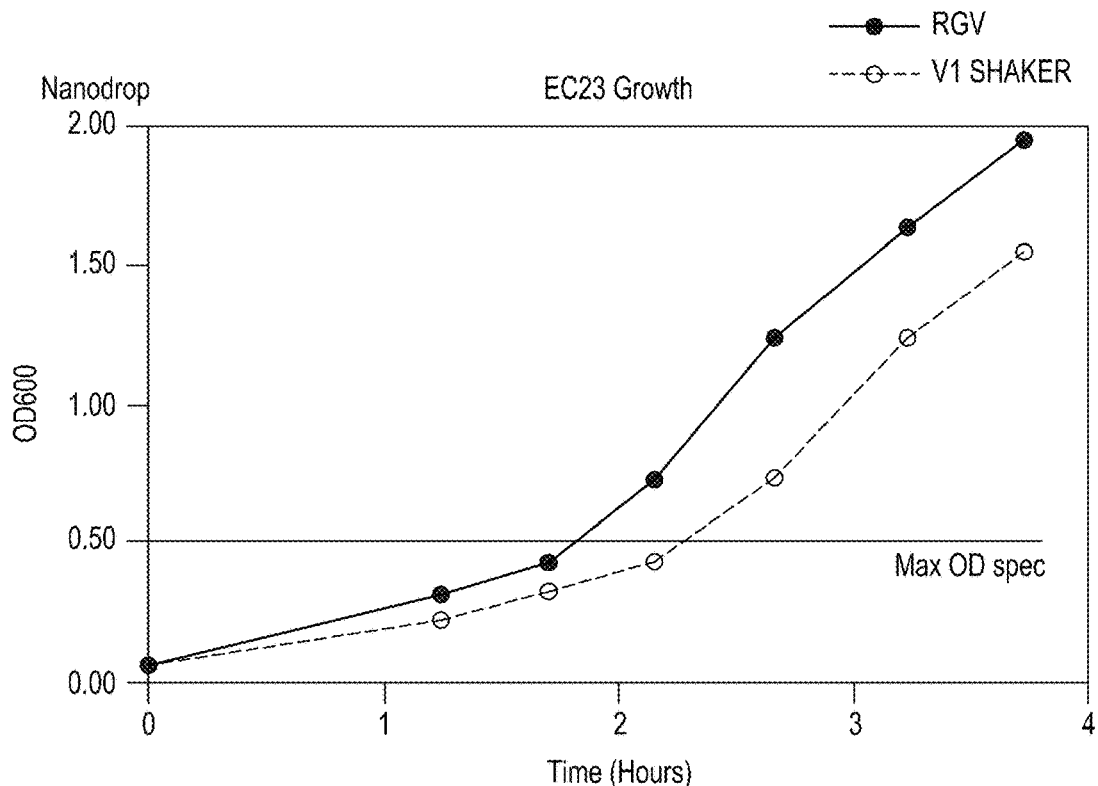
FIG. 16 is a graph demonstrating the effectiveness of a 3-paddle rotating growth vial and cell growth device as described herein for growing an EC23 cell culture vs. a conventional cell shaker.

In a first example, 20 ml EC23 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 5 ml EC23 cells in LB were grown in a 5 ml tube at 30° C. and were shaken at 750 rpm. $OD_{600}$ was measured at intervals using a NanoDrop™ spectrophotometer (Thermo Fisher Scientific). The results are shown in FIG. 15. The rotating growth vial/cell growth device performed better than the cell shaker in growing the cells to $OD_{600}$ 2.6 in slightly over 4 hours. Another experiment was performed with the same conditions (volumes, cells, oscillation) the only difference being a 3-paddle rotating growth vial was employed with the cell growth device, and the results are shown in FIG. 16. Again, the rotating growth vial/cell growth device performed better than the cell shaker in growing the cells to $OD_{600}$ 1.9.

Figure 17:
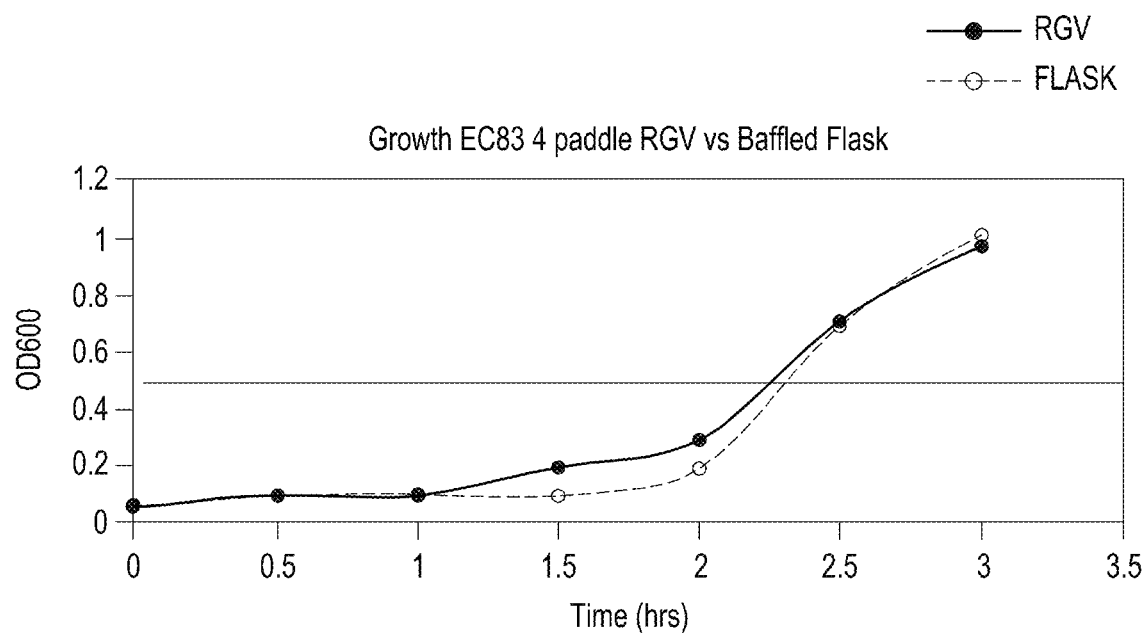
FIG. 17 is a graph demonstrating the effectiveness of a 4-paddle rotating growth vial and cell growth device as described herein for growing an EC138 cell culture vs. a conventional orbital cell shaker.
Figure 18:
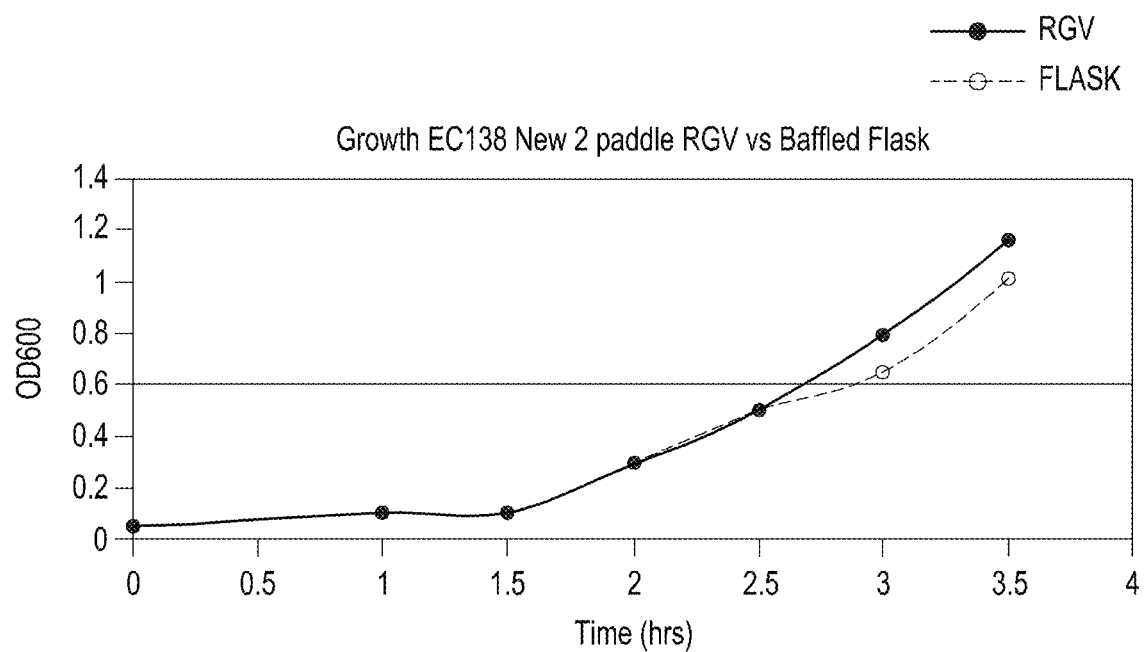
FIG. 18 is a graph demonstrating the effectiveness of a 2-paddle rotating growth vial and cell growth device as described herein for growing an EC138 cell culture vs. a conventional orbital cell shaker.

Two additional experiments were performed, this time comparing the rotating growth vial/cell growth device to a baffled flask and an orbital shaker. In one experiment, 20 ml EC138 cells (*E. coli* cells) in LB were grown in a 35 ml rotating growth vial with a 4-paddle configuration at 30° C. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results are shown in FIG. 17, demonstrating that the rotating growth vial/cell growth device performed as well as the orbital shaker in growing the cells to $OD_{600}$ 1.0. In a second experiment 20 ml EC138 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results are shown in FIG. 18, demonstrating that the rotating growth vial/cell growth device performed as well—or better—as the orbital shaker in growing the cells to $OD_{600}$ 1.2.

Figure 19:
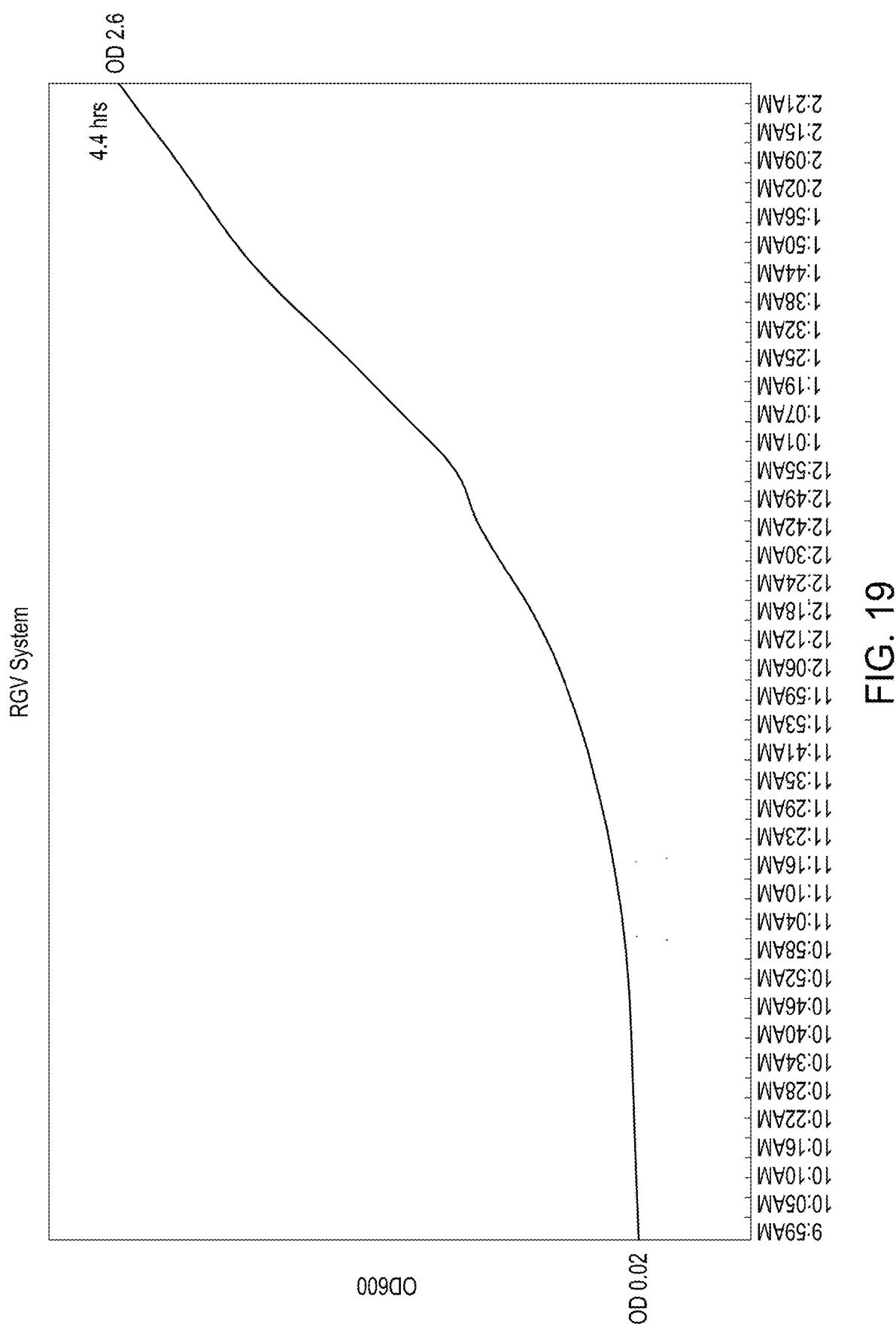
FIG. 19 is a graph demonstrating real-time monitoring of growth of an EC138 cell culture to $OD_{600}$ employing the cell growth device as described herein where a 2-paddle rotating growth vial was used.

In yet another experiment, the rotating growth vial/cell growth device was used to measure $OD_{600}$ in real time. FIG. 19 is a graph showing the results of real time measurement of growth of an EC138 cell culture at 30° C. using oscillating rotation and employing a 2-paddle rotating growth vial. Note that $OD_{600}$ 2.6 was reached in 4.4 hours.

Figure 20:
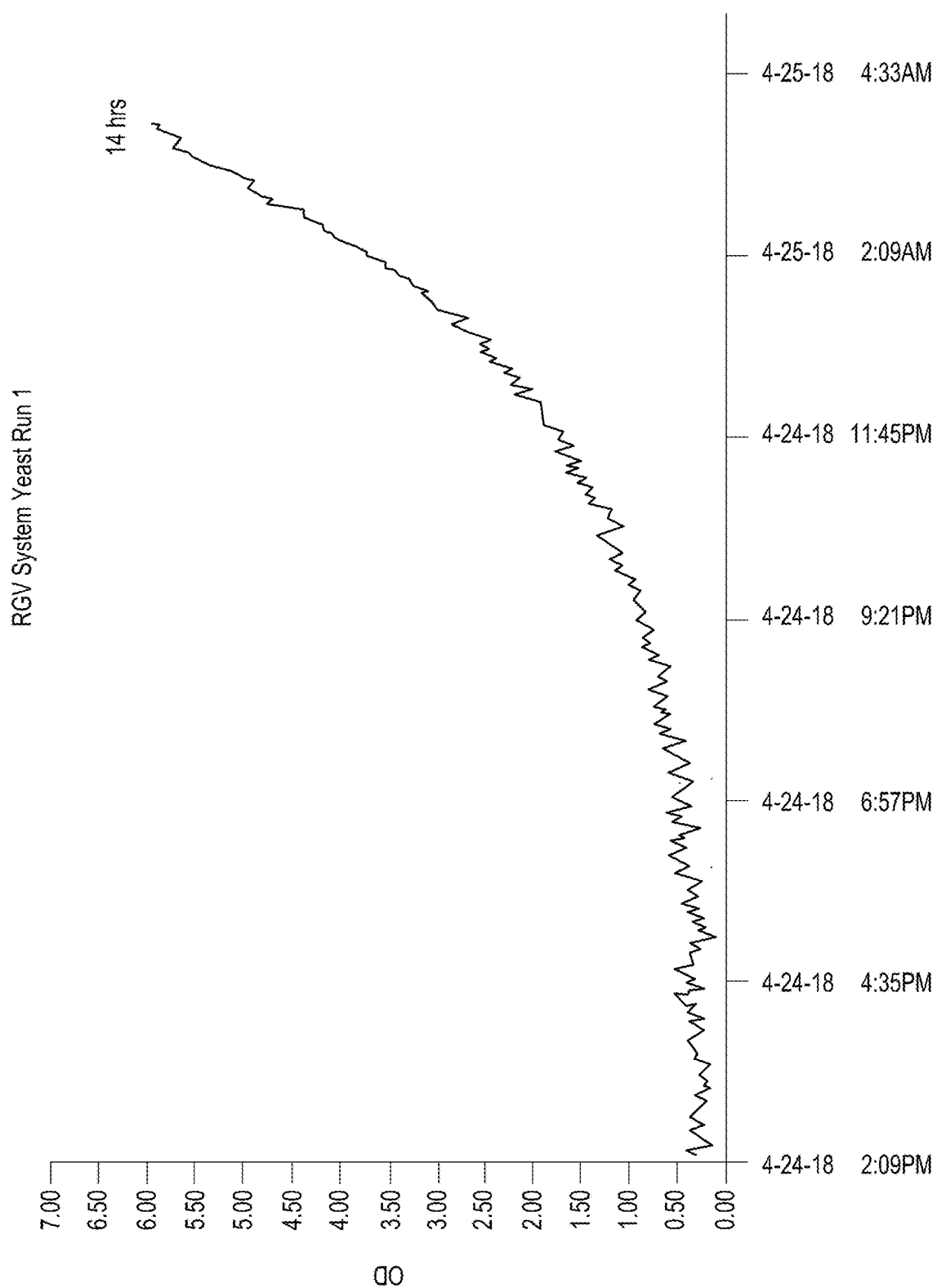
FIG. 20 is a graph demonstrating real-time monitoring of growth of s288c yeast cell culture $OD_{600}$ employing the cell growth device as described herein where a 2-paddle rotating growth vial was used.

In another experiment, the rotating growth vial/cell growth device was used to measure $OD_{600}$ in real time of yeast s288c cells in YPAD. The cells were grown at 30° C. using oscillating rotation and employing a 2-paddle rotating growth vial. FIG. 20 is a graph showing the results. Note that $OD_{600}$ 6.0 was reached in 14 hours.

Example 2: Cell Concentration

The TFF module as described above in relation to FIGS. 6A-6I has been used successfully to process and perform buffer exchange on both *E. coli* and yeast cultures. In concentrating an *E. coli* culture, the following steps were performed:

First, a 20 ml culture of *E. coli* in LB grown to OD 0.5-0.62 was passed through the TFF device in one direction, then passed through the TFF device in the opposite direction. At this point the cells were concentrated to a volume of approximately 5 ml. Next, 50 ml of 10% glycerol was added to the concentrated cells, and the cells were passed through the TFF device in one direction, in the opposite direction, and back in the first direction for a total of three passes. Again the cells were concentrated to a volume of approximately 5 ml. Again, 50 ml of 10% glycerol was added to the 5 ml of cells and the cells were passed through the TFF device for three passes. This process was repeated; that is, again 50 ml 10% glycerol was added to cells concentrated to 5 ml, and the cells were passed three times through the TFF device. At the end of the third pass of the three 50 ml 10% glycerol washes, the cells were again concentrated to approximately 5 ml of 10% glycerol. The cells were then passed in alternating directions through the TFF device three more times, wherein the cells were concentrated into a volume of approximately 400 µl.

Figure 21A:
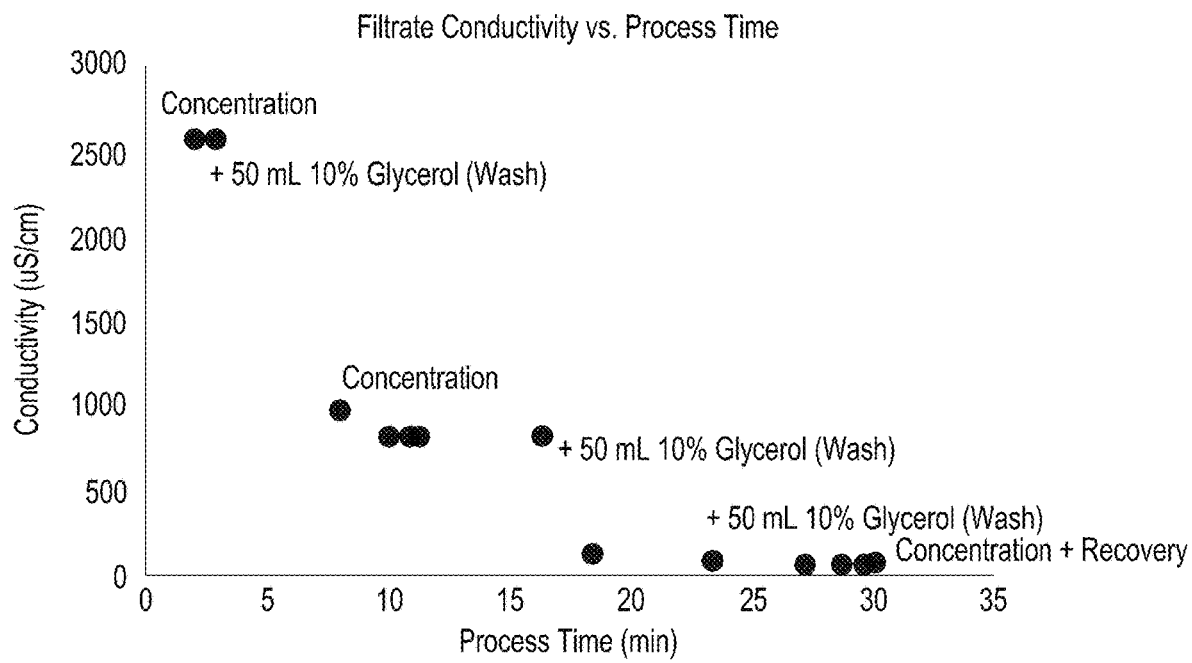
FIG. 21A is a graph plotting filtrate conductivity against filter processing time for an *E. coli* culture processed in the cell concentration device/module described herein.

Filtrate conductivity and filter processing time was measured for *E. coli* with the results shown in FIG. 21A. Filter performance was quantified by measuring the time and number of filter passes required to obtain a target solution electrical conductivity. Cell retention was determined by comparing the optical density (OD600) of the cell culture both before and after filtration. Filter health was monitored by measuring the transmembrane flow rate during each filter pass. Target conductivity (~16 µS/cm) was achieved in approximately 30 minutes utilizing three 50 ml 10% glycerol washes and three passes of the cells through the device for each wash. The volume of the cells was reduced from 20 ml to 400 µl, and recovery of approximately 90% of the cells has been achieved.

Figure 21B:
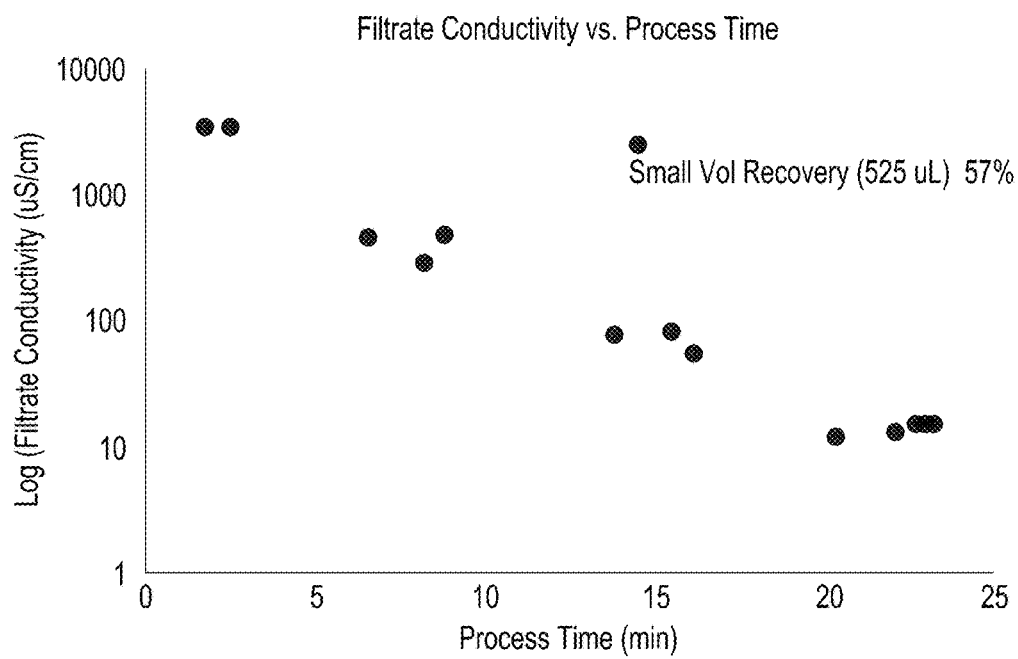
FIG. 21B is a graph plotting filtrate conductivity against filter processing time for a yeast culture processed in the cell concentration device/module described herein.

The same process was repeated with yeast cell cultures. A yeast culture was initially concentrated to approximately 5 ml using two passes through the TFF device in opposite directions. The cells were washed with 50 ml of 1M sorbitol three times, with three passes through the TFF device after each wash. After the third pass of the cells following the last wash with 1M sorbitol, the cells were passed through the TFF device two times, wherein the yeast cell culture was concentrated to approximately 525 µl. FIG. 21B presents the filter buffer exchange performance for yeast cells determined by measuring filtrate conductivity and filter processing time. Target conductivity (~10 µS/cm) was achieved in approximately 23 minutes utilizing three 50 ml 1M sorbitol washes and three passes through the TFF device for each wash. The volume of the cells was reduced from 20 ml to 525 µl. Recovery of approximately 90% of the cells has been achieved.

Example 3: Production and Transformation of Electrocompetent *E. coli* and *S. cerevisiae*

For testing transformation of the FTEP device, electrocompetent *E. coli* cells were created. To create a starter culture, 6 ml volumes of LB chlor-25 (LB with 25 µg/ml chloramphenicol) were transferred to 14 ml culture tubes. A 25 µl aliquot of *E. coli* was used to inoculate the LB chlor-25 tubes. Following inoculation, the tubes were placed at a 45° angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hr. When the OD600 of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells are aliquoted in 1:100 dilutions of cell suspension and ice-cold glycerol.

The comparative electroporation experiment was performed to determine the efficiency of transformation of the electrocompetent *E. coli* using the FTEP device described. The flow rate was controlled with a pressure control system. The suspension of cells with DNA was loaded into the FTEP inlet reservoir. The transformed cells flowed directly from the inlet and inlet channel, through the flow channel, through the outlet channel, and into the outlet containing recovery medium. The cells were transferred into a tube containing additional recovery medium, placed in an incubator shaker at 30° C. shaking at 250 rpm for 3 hours. The cells were plated to determine the colony forming units (CFUs) that survived electroporation and failed to take up a plasmid and the CFUs that survived electroporation and took up a plasmid. Plates were incubated at 30° C.; *E. coli* colonies were counted after 24 hrs.

Figure 22A:
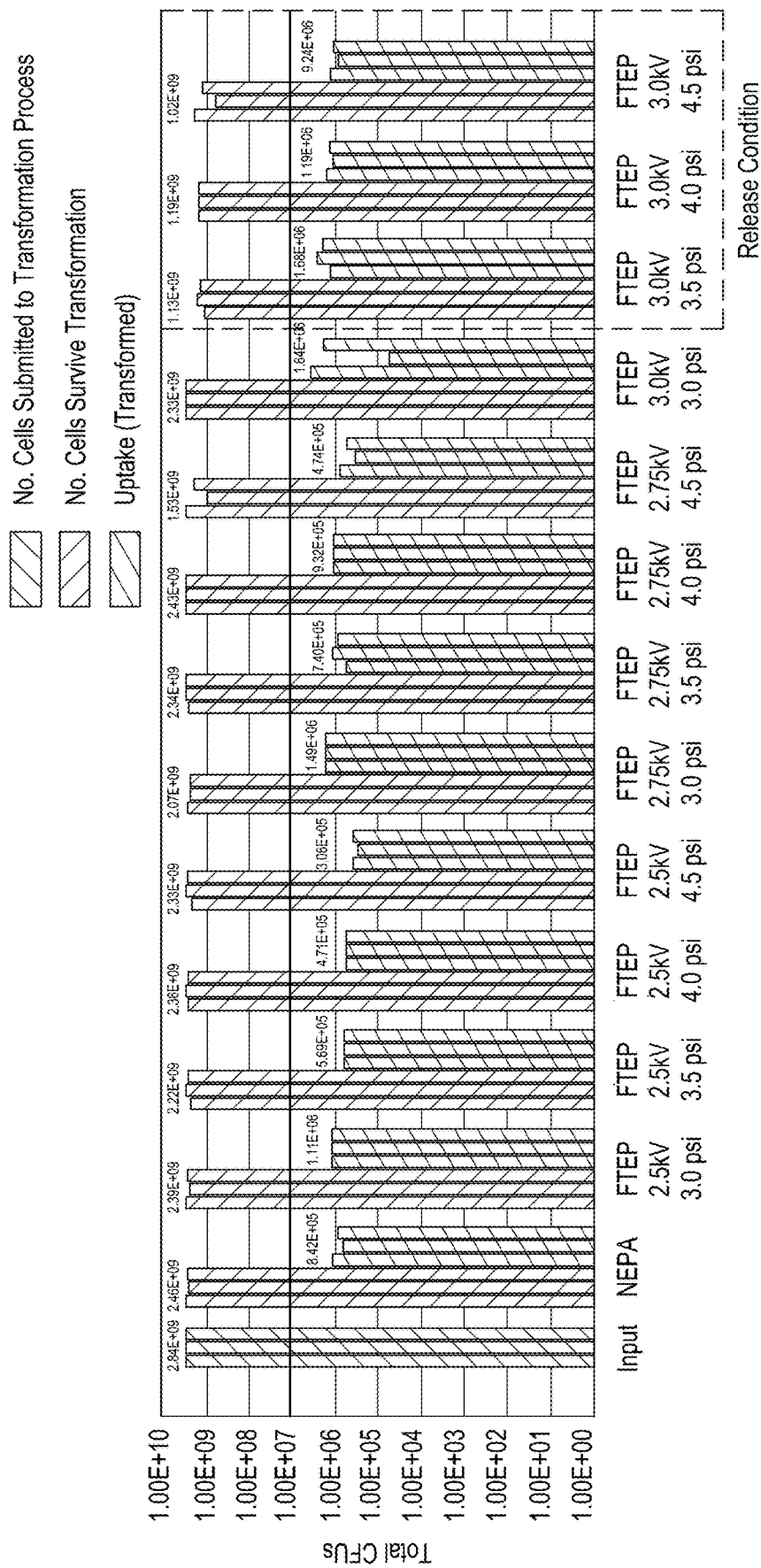
FIG. 22A is a bar graph showing the results of electroporation of *E. coli* using a device of the disclosure and a comparator electroporation device.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 22A. In FIG. 22A, the left-most bars hatched /// denote cell input, the bars to the left bars hatched \\\ denote the number of cells that survived transformation, and the right bars hatched /// denote the number of cells that were actually transformed. The FTEP device showed equivalent transformation of electrocompetent *E. coli* cells at various voltages as compared to the NEPAGENE™ electroporator. As can be seen, the transformation survival rate is at least 90% and in some embodiments is at least 95%, 96%, 97%, 98%, or 99%. The recovery ratio (the fraction of introduced cells which are successfully transformed and recovered) is in certain embodiments at least 0.001 and preferably between 0.00001 and 0.01. In FIG. 25A the recovery ratio is approximately 0.0001.

Figure 22B:
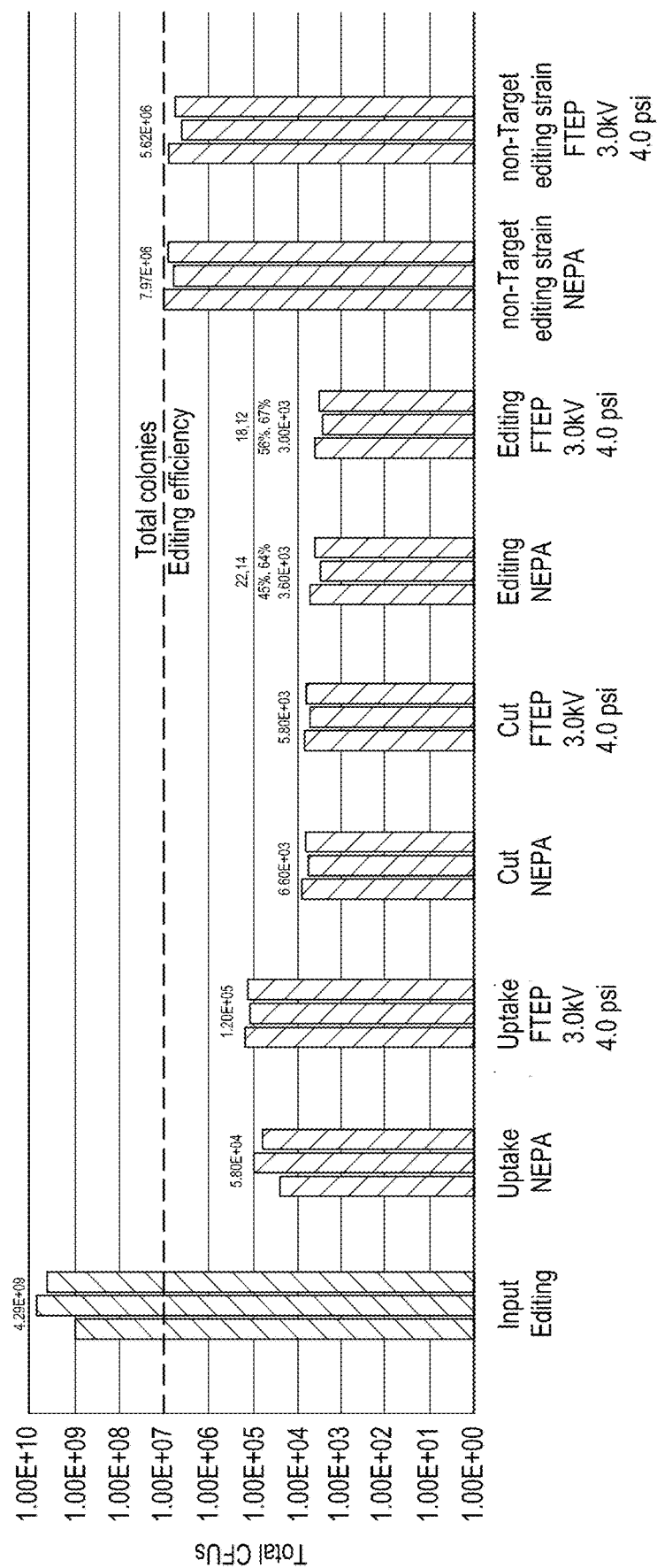
FIG. 22B is a bar graph showing uptake, cutting, and editing efficiencies of *E. coli* cells transformed via an FTEP as described herein benchmarked against a comparator electroporation device.

Additionally, a comparison of the NEPAGENE™ ELEPO21 and the FTEP device was made for efficiencies of transformation (uptake), cutting, and editing. In FIG. 22B, triplicate experiments were performed where the bars hatched /// denote the number of cells input for transformation, and the bars hatched \\\ denote the number of cells that were transformed (uptake), the number of cells where the genome of the cells was cut by a nuclease transcribed and translated from a vector transformed into the cells (cutting), and the number of cells where editing was effected (cutting and repair using a nuclease transcribed and translated from a vector transformed into the cells, and using a guide RNA and a donor DNA sequence both of which were transcribed from a vector transformed into the cells). Again, it can be seen that the FTEP showed equivalent transformation, cutting, and editing efficiencies as the NEPAGENE™ electroporator. The recovery rate in FIG. 22B for the FTEP is greater than 0.001.

For testing transformation of the FTEP device in yeast, *S. cerevisiae* cells were created using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent *S. cerevisiae* using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 23:
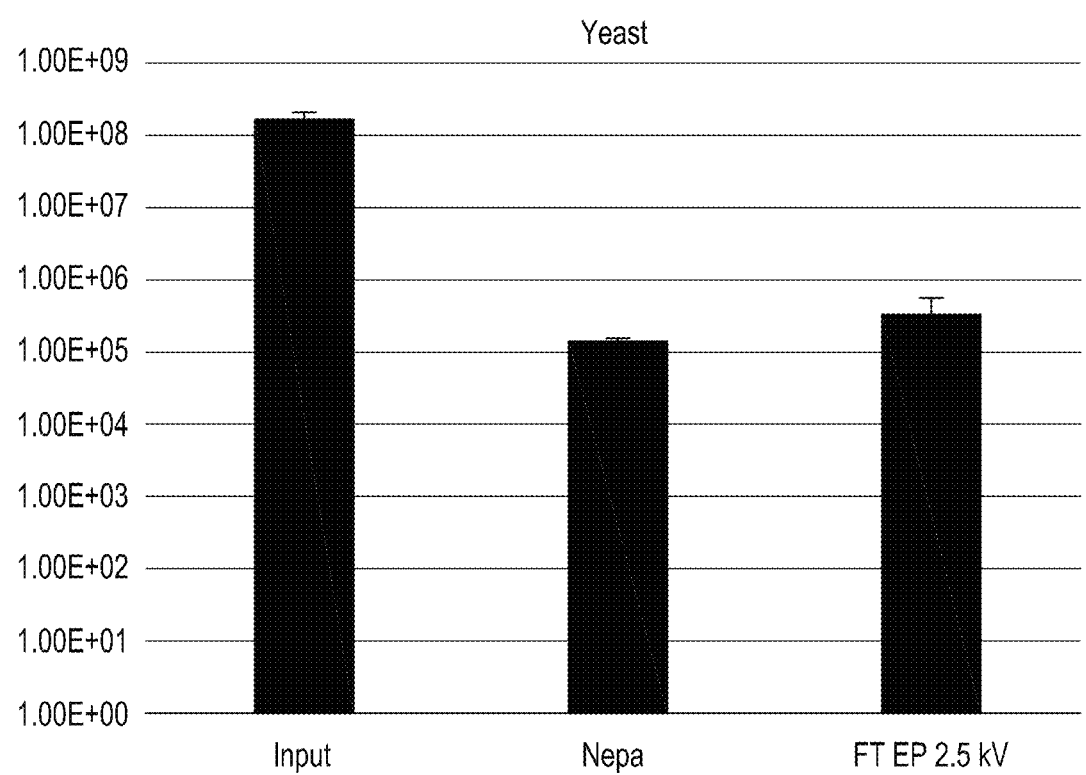
FIG. 23 is a bar graph showing the results of electroporation of *S. cerevisiae* using an FTEP device of the disclosure and a comparator electroporation method.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 23. The device showed better transformation and survival of electrocompetent *S. cerevisiae* at 2.5 kV voltages as compared to the NEPAGENE™ method. Input is total number of cells that were processed.

Example 4: Fully-Automated Singleplex RGN-Directed Editing Run

Singleplex automated genomic editing using MAD7 nuclease was successfully performed with an automated multi-module instrument of the disclosure. See U.S. Pat. No. 9,982,279; and U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example 5: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

Example 6: Design and Creation of a Yeast Display Library of Putative TCR Antigens The binding motifs for peptides presented by human MHC allele HLA-A*02 have been well characterized (Falk, K., et al., Nature, 1991. 351(6324): p. 290-296; Glanville, J., et al., Nature, 2017. 547(7661): p. 94-98) and a number of restricted clinically relevant TCRs identified (Johnson, L. A., et al., Blood, 2009. 114(3): p. 535-546). A yeast-display library for screening potential HLA-A*02:01 restricted TCRs is created as follows. A library of approximately 10,000 oligonucleotide editing cassettes for introduction of synthetic pMHC (Glanville, J, supra) peptides of different sequence into the genome of S. cerevisiae are designed and ordered from Agilent (Santa Clara, Calif.).

Briefly, the structural elements of each of the oligo cassettes is as follows: a promoter region, a CRISPR guide RNA region, an optional spacer region, a homology arm and optionally other sequences (e.g., barcodes) helpful for further analysis based on the functional assay to be used in the selection and/or confirmation of the specific edits. The cassettes range in length from 180 nt to 230 nt, depending on the edit to be introduced and the overall design of the oligos. The design of the homology arm includes a synonymous codon change (if necessary) to generate a restriction site which is used to insert constant regions of the cassette. These constant regions include the HLA-A*02:01 heavy chain and the AGA2P cell surface display conferring protein. The constant region may also contain an epitope tag for ease of downstream use in selections.

Briefly, the structural elements of each of the oligo cassettes is as follows: a promoter region, a CRISPR guide RNA region, an optional spacer region, a homology arm and optionally other sequences (e.g., barcodes) helpful for further analysis based on the functional assay to be used in the selection and/or confirmation of the specific edits. The cassettes range in length from 180 nt to 230 nt, depending on the edit to be introduced and the overall design of the oligos. The design of the homology arm includes a synonymous codon change (if necessary) to generate a restriction site which is used to insert constant regions of the cassette. These constant regions include the HLA-A*02:01 heavy chain and the AGA2P cell surface display conferring protein. The constant region may also contain an epitope tag or barcode "handle" for ease of downstream use in selections and further analysis. In addition or alternatively, the cassette design may include the addition of a "landing. pad" for the future addition of sequences. The CRISPR guide RNA region may also be targeted to a high efficiency cut and integration site.

Optionally, the oligonucleotide editing cassettes can be further processed with degenerate PCR reactions to generate $10^7$-$10^8$ permutations of the original TCR antigen sequence. Such degenerate PCR can be performed either before or after introduction into the genome of the cells. Degenerate PCR reactions are performed with primers positioned over the portions of the intended edit representing the peptide displayed on the pMHC construct (See, e.g., Boder, E. T. and K. D. Wittrup, Nature Biotechnology, 1997. 15(6): p. 553-557; McMahon, C., et al., Nature Structual & Molecular Biology, 2018. 25(3): p. 289-296).

Importantly, combinatorial sequence diversity could be created anywhere along the heavy chain construct representing the HLA-A allele as well as in the peptide region. Individual yeast then express a random peptide tethered to the constant HLA molecule. HLA-A*02:01 typically presents peptides 8 to 11 amino acids in length (Hassan, C., et al., The Journal of Biological Chemistry, 2015. 290(5): p. 2593-2603 and peptide length libraries are generated using peptides of lengths within these ranges. The library has a theoretical nucleotide diversity dictated by the library composition and length but is designed to result in one or more libraries representing millions of unique peptides ranging from 8 to 11 amino acids. After incubating the cells and going through the editing process, a pool of edited cells exists with the pMHC complex displayed on the surface of the cell attached to the AGA2P protein. An optional initial selection for edited cells displaying the pMHC complex can be performed via the displayed epitope tag.

Example 7: Validation of the Proper Identification of TCR Antigens Using a Yeast Display Library A validation study is performed to determine whether the HLA-A*02:01 complex on the surface of the cells in the library of Example 1 is properly folded to present peptides. The validation uses the identification of cells displaying target antigens of TCRs with known specificities. Briefly, a system is designed using the libraries generated as in Example 1 to validate the libraries for proper expression of the antigens. In this system, yeast cells displaying the pMHC conjugates are exposed to a population of expanded T-cells from a single T-cell with known TCR. Using this system, a user can correctly match TCRs to a known predicted antigen target. Selections are performed using TCRs with known antigen sequences. Following selection, the selected samples are determined, e.g. using sequencing of barcodes associated with the selected antigens in the cells of the library. The top peptide antigens identified using the system of the disclosure are able to stimulate TCR-transduced T cells, despite sequence differences from the actual epitope.

Example 8: Identification of New TCR Antigens Using a Yeast Display Library

To test whether the automated system would work to identify novel antigen targets, known TCRs and/or orphan TCRs are used to identify antigens using the methods of the disclosure. These identified antigens can then be used by bioinformatic methods to query the universe of expected or potential peptide antigens. These bioinformatics methods will attempt to determine common peptides derived from known protein sequences that will also bind the representative TCRs. These predicted peptide sequences can then be designed into one of the libraries of Example 1 or directly tested with other assays. These libraries which are then displaying the predicted peptide pMHC molecules can then be exposed to one or more orphan TCRs to find antigens that specifically bind to the orphan TCRs. These peptides are then identified as probable antigen targets for the TCRs.

Example 9: Identification of Genome-Wide Protein-Protein Interactions

Protein-protein interactions have been traditionally studied in high-throughput using yeast two hybrid (Y2H) based approaches (Rolland, T., et al, Cell, 2014. 159(5): p. 1212-1226; Huttlin, E. L., et al., 2017. 545(7655): p. 505-509) or mass-spectrometry based assays (Hein, Marco Y., et al., Cell, 2015. 163(3): p. 712-723. Flow cytometry has also been used heavily to enable yeast surface display applications and has been extended to facilitate studies of protein-protein interactions and enzymatic properties (Lim, S., et al., Biotechnology Journal, 2017. 12(5): p. 10; Cherf, G. M. and J. R. Cochran, Methods in molecular biology (Clifton, N.J.), 2015. 1319: p. 155-175.

CREATE display can be used to facilitate rapid screening of one vs. all or all vs. all protein-protein interactions. First, a genome-wide CREATE display library is generated by ordering a set of approximately 6,000 oligonucleotide editing cassettes from Agilent (Santa Clara, Calif.). These oligonucleotide editing cassettes are configured as described in previous examples with a crRNA, spacer region, and homology arm. These particular oligonucleotide cassettes can also optionally contain optimally positioned restriction enzyme sites if they contain repetitive sequence to aid in the addition of a surface display conferring tag via standard cloning methods. Many surface display conferring tags exist. McMahon, C., et al., supra; Cherf, G. M. and J. R. Cochran, Methods in molecular biology (Clifton, N.J.), 2015. 1319: p. 155-175; Uchañski, T., et al., Scientific Reports, 2019. 9(1): p. 382. These may include and extend upon the original method of using the yeast AGA2P mating protein that is typically fused to the N-terminus of the displayed protein or peptide of interest (Boder, E. T. and K. D. Wittrup, supra). To facilitate display of essential proteins critical to cellular function a non-optimal cleavage site could optionally be designed in-between the surface display conferring tag and the protein of interest. Many cleavage conferring sequences exist but one exemplar is tobacco etch virus (TEV) cleavage site which could be modified to result in sub-optimal cleavage (Ioannou, M., et al., *Mammalian expression vectors for metabolic biotinylation tandem affinity tagging by co-expression in cis of a mammalian codon-optimized BirA biotin ligase*. BMC research notes, 2018. 11(1): p. 390-390) and hence simultaneous surface display of the desired protein while maintaining a viable intracellular concentration of the native protein. Once oligonucleotide cassettes have been designed, ordered, and subsequently modified to include the standard parts conferring display to the surface of the cell, the CREATE process can proceed. Briefly, as described previously, a population of cells is transformed with the oligonucleotide cassettes and incubated using an automated machine that results in a population of edited cells. This population of cells is such that each individual cell contains one or more edits that have resulted in insertion of the cell surface display conferring tag at a designed location of interest around the genome. To create a genome-wide library displaying all proteins in the yeast genome approximately 6,572 edits would be made to insert surface display conferring tags at the N-terminus of all 6,572 annotated proteins in the yeast genome (https://www.yeastgenome.org/genomesnapshot). This would result in a library of 6,572 distinct cells each displaying one of the 6,572 proteins on its surface. This library of cells could then be split into two populations and one of the populations transformed with a construct expressing green-fluorescent-protein (GFP). The two populations could then be incubated together and run through a flow-cytometer to detect doublet formation (Wersto, R. P., et al., Cytometry, 2001. 46(5): p. 296-306) indicative of a positive protein-protein interaction. Doublets can then be placed into individual partitions of a standard 96 or 384 well plate and the DNA sequence barcodes read off of the cassettes present in each cell of the doublet to determine a protein-protein interaction. Notably, this technique can be performed in an all-by-all manner in which all 6,572 GFP expressing surface displayed proteins are incubated with all 6,572 non-GFP expressing surface displayed proteins. However, it can also be performed in a one-vs-all or many-vs-all configuration in which isolates of a protein of specific interest are incubated and sorted using flow cytometry as described above. This one-vs-all or many-vs-all could offer additional specificity or clarity to determination of an individual proteins binary interaction partners. It should also be noted that this same procedure can be done throughout multiple rounds of screening as is traditionally done in phage or yeast display (Bradbury, A. R. M., et al., Nature Biotechnology, 2011. 29: p. 245) to selectively enrich for the highest affinity binding partners and to lower false positive rates. It can also be used on a previously edited genome containing pathogenic or other variants of interest edited into the cell population before introduction of the cell surface display conferring tags. The previously edited genomes could also contain sets of variants specifically designed to disrupt protein-protein interactions. Notably, CREATE display can also be used to display more than one protein on the surface of a single cell via introduction of multiple tags at multiple loci throughout a cell.

Example 10: Identifying Druggable Targets

Identifying targets of drugs and subsequent mechanism of action remains a challenging endeavor. Schenone, M., et al., Nature Chemical Biology, 2013. 9: p. 232; Stockwell, B. R., *Exploring biology with small organic molecules*. Nature, 2004. 432(7019): p. 846-854; Xie, L., L. Xie, and P. E. Bourne, *Structure-based systems biology for analyzing off-target binding*. Current opinion in structural biology, 2011. 21(2): p. 189-199.

Reverse genetic screens tend to use computational or other rational methods to pre-select a list of likely disease related targets. Biochemical screens are then performed using a library of chemical compounds against one or more of these disease related targets. However, biochemical assays are often costly or time consuming and subsequently are generally limited to a small number of potential targets. 17. Wyatt, P. G., et al., *Target validation: linking target and chemical properties to desired product profile*. Current topics in medicinal chemistry, 2011. 11(10): p. 1275-1283.

The small number of feasible targets in biochemical screens often translates into an inability to identify potential off-targets which can then result in difficult to understand side effects and a necessary "deconvolution" step whilst determining mechanism of action. Knight, Z. A., H. Lin, and K. M. Shokat, Nature reviews. Cancer, 2010. 10(2): p. 130-137.

In contrast, forward genetic screens generally start with a phenotype of interest and then screen a large number of molecules against the model system to see if the phenotype can be disrupted. Stockwell, B. R., *Exploring biology with small organic molecules*. Nature, 2004. 432(7019): p. 846-854.

This however can often result in not knowing what protein or pathway the molecule is targeting and can also lead to unintended side-effects when administered in further studies or in patients. Xie, L., et. Al., supra.

Both forward and reverse genetic screens could greatly benefit from the ability to uniformly assess the binding of a drug to all intracellular proteins in a simple cost-effective assay. For forward screens it can identify the actual targets and for reverse screens it can identify off-targets. Using the CREATE display methods described here, one can efficiently generate a library displaying all possible cellular proteins on the surface of a population of cells and then expose that population to a small molecule with an attached fluorophore or other detection handle to determine all protein-drug binding events. First a CREATE display library is generated as described in Example 5. This display library can optionally display all proteins in a genome or a subset of proteins particular to a pathway or computationally determined set of interest. This display library can also be created in a population of cells that already harbors one or more pathogenic variants identified a priori and programmed into the cell population via previous rounds of CREATE. This library can then be exposed to a single molecule of interest with an attached organic fluorophore. Incubation of the CREATE display library with the small molecule of interest results in complexes of small molecule bound to the cells displaying a protein in the case in which the small molecule can bind that protein. Using flow cytometry, the cells displaying protein with bound ligand can be sorted and barcodes on the CREATE cassettes used to determine which proteins are bound by a given small molecule. This results in a binary mapping of small molecule to protein and can uniquely identify all possible binding partners of a given small molecule. Optionally, using a DNA encoded chemical library or other combinatorial screening approaches (Zimmermann, G. and D. Neri, Drug discovery today, 2016. 21(11): p. 1828-1834; Szymański, P., M. Markowicz, and E. Mikiciuk-Olasik, International journal of molecular sciences, 2011. 13(1): p. 427-452) one could perform an all-by-all screen of a library of chemical compounds against a CREATE display library of surface displayed proteins.

Example 11: Affinity Maturation of Biological Binders to a Pathway of Interest

Traditional antibody drug development has focused on cell surface or other extracellular targets that can be readily accessed by an antibody. However, of the approximately 700 protein molecular targets approved for drugs, more than half are intracellular proteins. See, e.g., Carter, P. J. and G. A. Lazar, Nature Reviews Drug Discovery, 2017. 17: p. 197; Santos, R., et al., Drug discovery, 2017. 16(1): p. 19-34; Wang, X., et al., Genome biology and evolution, 2013. 5(7): p. 1291-1297.

Significant efforts are underway to develop delivery systems for antibodies or small peptide therapeutic molecules. Stewart, M. P., et al., Nature, 2016. 538: p. 183. If the promise of intracellular antibody or peptide delivery comes to fruition, then a method to systematically affinity mature antibodies that bind to one or more intracellular proteins would be of tremendous value. Using CREATE display, a large library of intracellular proteins can be displayed on the surface of a population of cells and systematically exposed to yeast or phage display libraries to select for mono, bi, or poly-specific binders to a set of targets. First, a yeast display library would be created via the methods described here or as described elsewhere (McMahon, C., et al., supra; Lim S. et al., supra; Cherf, G. M. and J. R. Cochran, supra) in which many combinatorically encoded proteins are encoded into a population of yeast cells for display on the surface. At this point, the workflow would proceed in the same fashion as laid out in Example 5. In particular, the library of cells with combinatorically encoded peptides displayed on the surface would also be transformed with DNA sequences conferring expression of green-fluorescent-protein. This library of cells with up $10^{\wedge}10$ distinct displayed antibodies, nanobodies, or peptide fragments would then be incubated with the CREATE displayed library of all intracellular proteins. Using flow cytometry and selecting for doublets would then enable determination of any pairwise binding interaction between the engineered peptide(s) and one or more surface displayed cellular proteins. This procedure could also be carried out iteratively in the same manner that traditional affinity maturation of antibodies is done via yeast display (Cherf, G. M. and J. R. Cochran, supra). Carrying it out iteratively on a library of surface displayed cellular proteins that represented a given pathway or subset of genomic proteins would result in identification of high-affinity binders to an entire pathway of proteins. In this manner poly-specific binders could be determined to inhibit or identify the mechanism of action for entire pathways. Importantly, in a genome-wide CREATE display library there is a built-in negative control for off-target affects via the presence in solution of all other intracellular proteins. Thus while selecting for binders to only a subset of proteins in a pathway, one can find the pareto optimum between strong binding to one or more desired intracellular proteins while simultaneously minimizing binding to non-desired intracellular proteins. Thus, throughout successive rounds of CREATE display one can affinity mature antibodies for binding to specific targets while also selecting for minimization of off-target binding to other intracellular proteins.

While this invention is satisfied by embodiments in many different forms, as described in detail in connection with embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. An automated method of creating a cell library co-expressing engineered peptides and MHC molecules using instrumentation, the method comprising:
providing a population of cells;
processing the population of cells using an instrument for multiplexed nuclease-directed genome editing using introduced nucleic acids and a nucleic acid-directed nuclease to create cells, wherein the introduced nucleic acids comprise nucleic acids that encode engineered peptides and MHC molecules configured to be displayed on a surface of the cells;
incubating the processed cells to facilitate nucleic acid editing in the cells, wherein the edited cells co-express the engineered peptide antigens and MHC molecules in the cells; and
allowing the cells to display the engineered peptides and MHC molecules on the surface of the cells.

2. The method of claim 1, wherein the engineered peptides are putative TCR binding antigens.

3. The method of claim 1, wherein the engineered peptides comprise predicted TCR binding regions.

4. The method of claim 1, wherein the population of cells are yeast cells.

5. The method of claim 1, wherein the nuclease is an RNA-directed nuclease.

6. An automated method of creating a cell library co-expressing engineered putative T-cell receptor (TCR) antigens and MHC molecules on a surface of cells, the method comprising:
providing a population of cells;
processing the population of cells using an instrument for multiplexed nuclease-directed genome editing using introduced nucleic acids and a nuclease to create cells, wherein the introduced nucleic acids comprise nucleic acids that encode engineered putative T-cell receptor (TCR) antigens and MHC molecules configured to be displayed on the surface of the cells;
incubating the processed cells to facilitate nucleic acid editing in the cells, wherein the edited cells co-express the engineered putative T-cell receptor (TCR) antigens and MHC molecules in the cells; and
allowing the cells to display the engineered putative T-cell receptor (TCR) antigens and MHC molecules on the surface of the cells.

7. The method of claim 6, wherein the population of cells are yeast cells.

8. The method of claim 6, wherein the population of cells are mammalian cells.

9. The method of claim 6, wherein the cells display the putative T-cell receptor (TCR) antigens and MHC molecules on the cells as part of a ligand.

10. The method of claim 6, wherein the nuclease is a nucleic acid-directed nuclease.

11. The method of claim 6, wherein the nuclease is an RNA-directed nuclease.

12. The method of claim 11, wherein the RNA-directed nuclease is MAD7.

13. The method of claim 6, wherein one or more of the engineered putative T-cell receptor (TCR) antigens are putative antigens of one or more orphan TCRs.

14. The method of claim 6, wherein one or more of the engineered putative T-cell receptor (TCR) antigens are known antigens of one or more TCRs.

15. An automated method of creating a cell library co-expressing engineered putative T-cell receptor (TCR) antigens and MHC molecules on the surface of the cells, the method comprising:
providing a population of cells;
processing the population of cells using an instrument for multiplexed nucleic acid-guided nuclease genome editing using introduced nucleic acids comprising a guide RNA and a donor DNA and nucleic acid-guided nuclease to create cells comprising nucleic acids that encode engineered putative T-cell receptor (TCR) antigens and MHC molecules configured to be displayed on a surface of the cells;
incubating the processed cells to facilitate nucleic acid editing in the cells, wherein the edited cells co-express the engineered putative T-cell receptor (TCR) antigens and MHC molecules in the cells; and
allowing the cells to display the engineered putative T-cell receptor (TCR) antigens and MHC molecules on the surface of the cells.

16. The method of claim 15, wherein the population of cells are yeast cells.

17. The method of claim 15, wherein the population of cells are mammalian cells.

* * * * *